(12) United States Patent
Bowcock et al.

(10) Patent No.: US 9,133,523 B2
(45) Date of Patent: Sep. 15, 2015

(54) COMPOSITIONS AND METHODS FOR DETECTING CANCER METASTASIS

(75) Inventors: Anne M. Bowcock, St. Louis, MO (US); J. William Harbour, St. Louis, MO (US)

(73) Assignee: Washington University, St. Louis, MO (US)

( * ) Notice: Subject to any disclaimer, the term of this patent is extended or adjusted under 35 U.S.C. 154(b) by 612 days.

(21) Appl. No.: 13/243,572

(22) Filed: Sep. 23, 2011

(65) Prior Publication Data

US 2012/0077682 A1    Mar. 29, 2012

Related U.S. Application Data

(60) Provisional application No. 61/385,696, filed on Sep. 23, 2010.

(51) Int. Cl.
*C12Q 1/68* (2006.01)
*G01N 33/574* (2006.01)

(52) U.S. Cl.
CPC .......... *C12Q 1/6886* (2013.01); *G01N 33/5743* (2013.01); *G01N 33/57496* (2013.01); *C12Q 2600/112* (2013.01); *C12Q 2600/118* (2013.01); *C12Q 2600/154* (2013.01); *C12Q 2600/156* (2013.01); *C12Q 2600/178* (2013.01); *G01N 2333/916* (2013.01)

(58) Field of Classification Search
None
See application file for complete search history.

(56) References Cited

U.S. PATENT DOCUMENTS

| | | |
|---|---|---|
| 6,194,557 B1 | 2/2001 | Li |
| 6,307,035 B1 | 10/2001 | Rauscher |
| 6,566,495 B1 | 5/2003 | Fodor et al. |
| 8,642,279 B2 | 2/2014 | Harbour et al. |
| 2006/0275844 A1 | 12/2006 | Linke et al. |
| 2007/0105133 A1 | 5/2007 | Clarke et al. |
| 2007/0207479 A1 | 9/2007 | Wong et al. |
| 2009/0275633 A1 | 11/2009 | Esteller |
| 2011/0124525 A1 | 5/2011 | Harbour |
| 2014/0141441 A1 | 5/2014 | Harbour et al. |

FOREIGN PATENT DOCUMENTS

| | | |
|---|---|---|
| GB | 2484003 | 3/2012 |
| WO | 2009132126 A2 | 10/2009 |
| WO | 2012/040614 A1 | 3/2012 |

OTHER PUBLICATIONS

Altschul, S. et al., "Basic Local Alignment Search Tool," J. Mol. Biol., Oct. 5, 1990, pp. 403-410, vol. 215, No. 3.
Char, D. et al., "Cytomorphometry of Uveal Melanoma. Comparison of Fine Needle Aspiration Biopsy Samples with Histologic Sections," Anal. Quant. Cytol. Histol., 1991, pp. 293-299, vol. 13, No. 4.
Edge, S. et al., Eds., "Malignant Melanoma of the Uvea," The AJCC Cancer Staging Manual, 7th edition, 2009, Springer, New York, pp. 547-553.
Efferth, T. et al., "Pharmacogenetics for individualized cancer chemotherapy," Pharmacol. Ther., 2005, pp. 155-176, vol. 107, No. 2.
Fang, Y. et al., "The potential role of ubiquitin c-terminal hydrolases in oncogenesis," Biochim. Biophys. Acta, Aug. 2010, ePub Mar. 17, 2010, pp. 1-6, vol. 1806, No. 1.
Harbour, J., "Clinical Overview of Uveal Melanoma: Introduction to Tumors of the Eye," Ocular Oncology, Albert DM, Polans A, eds., Marcel Dekker, New York, 2003, pp. 1-18.
Horsman, D. et al., "Monosomy 3 and Isochromosome 8q in a Uveal Melanoma," Cancer Genet. Cytogenet ., 1990, pp. 249-253, vol. 45, No. 2.
Lang, D. et al., "Pax3 functions at a nodal point in melanocyte stem cell differentiation," Nature, Feb. 24, 2005, pp. 884-887, vol. 433.
McNamara, M. et al., "Assessment of Chromosome Copy Number in Ocular Melanoma Using Fluorescence In Situ Hybridization," Cancer Genet. Cytogenet., 1997, pp. 4-8, vol. 98.
Naus, N. et al., "Characterization of Complex Chromosomal Abnormalities in Uveal Melanoma by Fluorescence In Situ Hybridization, Spectral Karyotyping, and Comparative Genomic Hybridization," Genes, Chromosomes and Cancer, Mar. 2001, pp. 267-273, vol. 30, No. 3.
Ng, S. et al., "Targeted capture and massively parallel sequencing of 12 human exomes," Nature, Sep. 10, 2009, pp. 272-276, vol. 461.
Office Action dated Oct. 15, 2012 for related British Patent Application No. 1116471.2; 2 pages.
Peng, H. et al., "Feature Selection Based on Mutual Information: Criteria of Max-Dependency, Max-Relevance, and Min-Redundancy," IEEE Trans. Pattern. Anal. Mach. Intell., Aug. 2005, pp. 1226-1238, vol. 27, No. 8.
Pinkel, D. et al., "High resolution analysis of DNA copy number variation using comparative genomic hybridization to microarrays," Nat. Genet., Oct. 1998, pp. 207-211, vol. 20.
Prescher, G. et al., "Nonrandom Chromosomal Abnormalities in Primary Uveal Melanoma," J. Natl. Cancer Inst., Nov. 21, 1990, pp. 1765-1769, vol. 82, No. 22.
Sisley, K. et al., "Cytogenetic Findings in Six Posterior Uveal Melanomas: Involvement of Chromosomes 3, 6, and 8," Genes, Chromosomes & Cancer, Sep. 1990, pp. 205-209, vol. 2, No. 3.
Wackerly, D. et al., "Mathematical Statistics with Applications," Belmont, CA, Duxbury Press, 1996, p. 107.
White, V. et al., "Acquired Homozygosity (Isodisomy) of Chromosome During Clonal Evolution of Uveal Melanoma: Association with Morphologic Heterogeneity," Genes, Chromosomes & Cancer, Feb. 1996, pp. 138-143, vol. 15, No. 2.
Zhang, D. et al., "Ramification Amplification: A novel Isothermal DNA Amplification Method," Mol. Diagnosis, Jun. 2001, pp. 141-150, vol. 6, No. 2.
Coupier, BAP1 and Breast Cancer Risk, Familial Cancer, 2005, pp. 273-277, vol. 4.
Aalto, Concomitant Loss of Chromosome 3, IOVS, 2001, pp. 313-317, vol. 42.

(Continued)

*Primary Examiner* — Jim Ketter
(74) *Attorney, Agent, or Firm* — Polsinelli PC

(57) ABSTRACT

The present invention encompasses compositions and methods for detecting cancer metastasis.

9 Claims, 44 Drawing Sheets
(27 of 44 Drawing Sheet(s) Filed in Color)

(56) References Cited

OTHER PUBLICATIONS

Watanabe, Gene Expression Signature and the Prediction of Lymph Node Metastasis in Colorectal Cancer by DNA Microarray, Dis Colon Return, Dec. 2009, pp. 1941-1948, vol. 52.
Harbour, Frequent Mutation of BAP1 in Metastasizing Uveal Melanomas, Science, Dec. 3, 2010, pp. 1410-1413, vol. 330.
International Search Report from related PCT application No. PCT/US2011/053058 dated Jan. 20, 2012.
Search Report from related UK application No. GB1116471.2 dated Oct. 3, 2011.
Preliminary examination from related UK application No. GB1116471.2 dated Sep. 27, 2011.
Landreville S. et al., "Emerging insights into the molecular pathogenesis of uveal melanoma," Future Oncol., Oct. 2008, p. 629-636, vol. 4, No. 5 (abstract only).
Midena, E. et al., "In vivo detection of monosomy in eyes with medium-sized uveal melanoma using transscleral fine needle aspiration biopsy," Eur. Ophthalmol., 2006, pp. 422-425, vol. 16, No. 3 (abstract only).
Office Action dated Sep. 25, 2012 for related U.S. Appl. No. 12/989,272; 7 pages.
Prescher, G. et al., "Prognostic implications of monosomy 3 in uveal melanoma," Lancet, May 4, 1996, pp. 1222-1225, vol. 347 (abstract only).
Russell, N. et al., "Deubiquitinating enzyme purification, assay inhibitors, and characterization," Methods Mol. Biol., 2005, pp. 207-219, vol. 301 (abstract only).
Tyagi, S. et al., "E2F activation of S phase promoters via association with HCF-1 and the MLL family of histone H3K4 methyltransferases," Mol. Cell, Jul. 6, 2007, pp. 107-119, vol. 27, No. 1 (abstract only).
Demidov et al., Eds., DNA Amplification: Current technologies and applications, 2004. Pub. Horizon Bioscience, ISBN:0-9545232-9-6.
Final Rejection dated Mar. 25, 2013 from related U.S. Appl. No. 12/989,272.
Search report and written opinion from the Dutch Intellectual Property office dated Feb. 9, 2012 from related application No. 2007467.
Guenard, Genetic sequence variations of BRCA1-interacting genes AURKA, BAP1, BARD1 and DHX9 in French Canadian Families with high risk of breast cancer, Journal of Human Genetics, Mar. 2009, pp. 152-161, vol. 54, No. 3.
Onken, Loss of heterozygosity of chromosome 3 detected with single nucleotide polymorphisms is superior to monosomy 3 for predicting metastasis in uveal melanoma, Clinical Cancer Research: An Official Journal of the American Association for Cancer Research, May 15, 2007, pp. 2923-2927, vol. 13, No. 10.
Harbour, Frequent Mutation of BAP1 in Metastasizing Uveal Melanomas, Science, Dec. 3, 2010, pp. 1410-1413, vol. 330, No. 6009.
Altschul, S. et al., "Gapped BLAST and PSI-BLAST: a new generation of protein database search programs," Nucleic Acids Res., 1997, pp. 3389-3402, vol. 25, No. 17.
Bashiardes, S. et al., "Direct genomic selection," Nat. Methods, Jan. 2005, pp. 63-69, vol. 2, No. 1.
Bauer, J. et al., "Oncogenic GNAQ mutations are not correlated with disease-free survival in uveal melanoma," Br. J. Cancer, 2009, pp. 813-815, vol. 101.
Combined Search and Examination Report dated Oct. 4, 2011 for related British Patent Application No. 1116471.2; 6 pages.
Cross, N. et al., "Multiple locations on chromosome 3 are the targets of specific deletions in uveal melanoma," Eye, Apr. 2006, pp. 476-481, vol. 20, No. 4.
European search report dated Jul. 22, 2011 for related European Patent Application No. 09735059.9; 10 pages.
Faulkner-Jones, B. et al., "Fine Needle Aspiration Biopsy with Adjunct Immunohistochemistry in Intraocular Tumor Management," Acta Cytol., May-Jun. 2005, pp. 297-308, vol. 49, No. 3.
Finger, P., "The 7th Edition AJCC Staging System for Eye Cancer," Arch. Pathol. Lab. Med., Aug. 2009, pp. 1197-1198, vol. 133, No. 8.
Garraway, L. et al., "Integrative genomic analyses identify MITF as a lineage survival oncogene amplified malignant melanoma," Nature, Jul. 7, 2005, pp. 117-122, vol. 436.
Gaytan De Ayala Alonso, A. et al., "A Genetic Screen Identifies Novel Polycomb Group Genes in *Drosophilia*," Genetics, Aug. 2007, pp. 2099-2108, vol. 176.
Golub, T. et al., "Molecular Classification of Cancer: Class Discovery and Class Prediction by Gene Expression Monitoring," Science, Oct. 15, 1999, pp. 531-537, vol. 286.
Gordon, K. et al., "Comparative Genomic Hybridization in the Detection of DNA Copy Number Abnormalities in Uveal Melanoma," Cancer Res., Sep. 1, 1994, pp. 4764-4768, vol. 54.
International Search Report and Written Opinion dated Aug. 13, 2009 for related International Patent Application No. PCT/US2009/041436; 9 pages.
Jensen, D. et al., "BAP1: a novel ubiquitin hydrolase which binds to the BRCA1 Ring finger and enhances BRCA1-mediated cell growth suppression," Oncogene, Mar. 5, 1998, pp. 1097-1112, vol. 16, No. 9.
Karlin, S. et al., "Methods for assessing the statistical significance of molecular sequence features by using general scoring schemes," Proc. Natl. Acad. Sci. USA, Mar. 1990, pp. 2264-2268, vol. 87, No. 6.
Kilic, E. et al., "Clinical and Cytogenetic Analyses in Uveal Melanoma," Invest. Ophthalmol. Vis. Sci., Sep. 2006, pp. 3703-3707, vol. 47, No. 9.
Machida, Y. et al., "The Deubiquitinating Enzyme BAP1 Regulates Cell Growth via Interaction with HCF-1," J. Biol. Chem., Dec. 4, 2009, pp. 34179-34188, vol. 284, No. 49.
Misaghi, S. et al., "Structure of the Ubiquitin Hydrolase UCH-L3 Complexed with a Suicide Substrate," J. Biol. Chem., Jan. 14, 2005, pp. 1512-1520, vol. 280, No. 2.
Misaghi, S. et al., "Association of C-Terminal Ubiquitin Hydrolase BRCA1-Associated Protein 1 with Cell Cycle Regulator Host Cell Factor 1," Mol. Cell. Biol., Apr. 2009, pp. 2181-2192, vol. 29, No. 8.
Ng, S. et al., "Exome sequencing identifies the cause of a mendelian disorder," Nat. Genet., Jan. 2010, pp. 30-36, vol. 42, No. 1.
Nishikawa, H. et al., "BRCA1-Associated Protein 1 Interferes with BRCA1/BARD1 RING Heterodimer Activity," Cancer Res., Jan. 1, 2009, pp. 111-119, vol. 69, No. 1.
Office Action dated Mar. 26, 2012 for related British Patent Application No. 1116471.2; 4 pages.
Onken, M. et al., "Functional Gene Expression Analysis Uncovers Phenotypic Switch in Aggressive Uveal Melanomas," Cancer Res., May 1, 2006, pp. 4602-4609, vol. 66, No. 9.
Onken, M. et al., "Oncogenic mutations in GNAQ occur early in uveal melanoma," Invest. Ophthalmol. Vis. Sci., Dec. 2008, pp. 5230-5234, vol. 49, No. 12 (with Author Manuscript, 12 pages).
Onken, M. et al., "An Accurate, Clinically Feasible Multi-Gene Expression Assay for Predicting Metastasis in Uveal Melanoma," J. Mol. Diagnostics, Jul. 2010, pp. 461-468, vol. 12, No. 4.
Onken, M. et al., "Gene Expression Profiling in Uveal Melanoma Reveals Two Molecular Classes and Predicts Metastatic Death," Cancer Res., Oct. 15, 2004, pp. 7205-7209, vol. 64.
Onken, M. et al., "Prognostic Testing in Uveal Melanoma by Transcriptomic Profiling of Fine Needle Biopsy Specimens," J. Mol. Diagnostics, Nov. 2006, pp. 567-573, vol. 8, No. 5.
Onken, M. et al., "Association Between Microarray Gene Expression Signature and Extravascular Matrix Patterns in Primary Uveal Melanomas," Am. J. Ophthalmol., Oct. 2005, pp. 748-749, vol. 140, No. 4.
Patel, K. et al., "Prediction of prognosis in patients with uveal melanoma using fluorescence in situ hybridization," Br. Ophthalmol., 2001, pp. 1440-1444, vol. 85.
Perry, A. et al., "NF1 Deletions in S-100 Protein-Positive and Negative Cells of Sporadic and Neurofibromatosis 1 (NF1)-Associated Plexiform Neurofibromas and Malignant Peripheral Nerve Sheath Tumors," Am. J. Pathol., Jul. 2001, pp. 57-61, vol. 159, No. 1.
Petrausch, U. et al., "Significance of gene expression analysis in uveal melanoma in comparison to standard risk factors for risk assessment of subsequent metastases," Eye, 2007, pp. 1-11.
Pusztai L. et al., "Clinical trial design for microarray predictive marker discovery and assessment," Ann. Oncol., 2004, pp. 1731-1737, vol. 15.

(56) References Cited

OTHER PUBLICATIONS

Rockett, J. et al., "DNA arrays: technology, options and toxicological applications," Xenobiotica, 2000, pp. 155-177, vol. 30, No. 2.

Sandinha, M. et al., "Monosomy 3 Predicts Death but Not Time Until Death in Choroidal Melanoma," Invest. Ophthalmol. Vis. Sci., Oct. 2005, pp. 3497-3501, vol. 46, No. 10.

Scharer, C., "Identification of the Transformational Properties and Transcriptional Targets of the Oncogenic SRY Transcription Factor SOX4," Emory University, Award No. W81XWH-07-1-0044, Annual Summary, prepared for U. S. Army Medical Research and Material Command, Jan. 10, 2008; 14 pages.

Scheuermann, J. et al., "Histone H2A deubiquitinase activity of the Polycomb repressive complex PR-DUB," Nature, May 13, 2010, pp. 243-247, vol. 465, No. 7295.

Schouten, J. et al., "Relative quantification of 40 nucleic acid sequences by multiplex ligation-dependent probe amplification," Nucl. Acid Res., 2002, pp. 1-13, vol. 30, No. 12, e57.

Sima, C. et al., "Superior feature-set ranking for small samples using bolstered error estimation," Bioinformatics, 2005, pp. 1046-1054, vol. 21, No. 7.

Taylor, J. et al., "Individualized Predictions of Disease Progression Following Radiation Therapy for Prostate Cancer," J. Clin. Oncol., Feb. 1, 2005, pp. 816-825, vol. 23, No. 4.

Tschentscher, F. et al., "Tumor Classification Based on Gene Expression Profiling Shows That Uveal Melanomas with and without Monosomy 3 Represent Two Distinct Entities," Cancer Res., May 15, 2003, vol. 63, p. 2578-2584.

Tse, W. et al., "Genome-wide loss-of-function analysis of deubiquitylating enzymes for zebrafish development," BMC Genomics, Dec. 30, 2009, vol. 10, No. 637.

Van Raamsdonk, C. et al., "Frequent somatic mutations of GNAQ in uveal melanoma and blue nevi," Nature, Jan. 29, 2009, pp. 599-602, vol. 457, No. 7229.

Ventii, K. et al., "BAP1 is a tumor suppressor that requires deubiquitinating activity and nuclear localization," Cancer Res., Sep. 1, 2008, pp. 6953-6962, vol. 68, No. 17.

Van Gils, W., Thesis entitled "Molecular Prognostic Markers in Unveal Melanoma: Expression Profiling and Genomic Studies," PrintPartners IpsKamp, Enschede, 2007, Erasmus MC, Rotterdam, Chapters 1-10, pp. 1-144 (128 total pages).

Wang, Y. et al., "MMDB: annotating protein sequences with Entrez's 3D-structure database," Nucleic Acids Res., Jan. 2007, pp. D298-D300, vol. 35, Database issue.

Wood, L. et al., "The Genomic Landscapes of Human Breast and Colorectal Cancers," Science, Nov. 16, 2007, pp. 1108-1113, vol. 318.

Worley, L. et al., "Transcriptomic versus Chromosomal Prognostic Markers and Clinical Outcome in Uveal Melanoma," Clin. Cancer Res., Mar. 1, 2007, pp. 1466-1471, vol. 13, No. 5.

Ye, H. et al., "Genomic assessments of the frequent loss of heterozygosity region on 8p21.3-~p22 in head and neck squamous cell carcinoma," Cancer Genetics and Cytogenetics, 2007, pp. 100-106, vol. 176.

Chang, S. et al., "Prognostic biomarkers in uveal melanoma: evidence for a stem cell-like phenotype associated with metastasis," Melanoma Res., Jun. 2008, pp. 191-200, vol. 18, No. 3 (abstract only).

Hemesath, T. et al., "MAP kinase links the transcription factor Microphthalmia to c-Kit signalling in melanocytes," Nature, Jan. 15, 1998, pp. 298-301, vol. 391 (abstract only).

Notice of Allowance dated Sep. 6, 2013 for related U.S. Appl. No. 12/989,272; 10 pages.

Office Action dated Jul. 21, 2014 for related European Patent Application No. 09735059.9; 8 pages.

FIG. 1D shGFP shBAP1

```
   1 ccgttcgccg ccccgccccg tccctcctct cccaccatcc gcgcccagcc ccgcccatcc
  61 ccgccttttc ccctagcctg ccccgcccct cctctcgccc cacctgcgcc cagcacttcc
 121 cggccccgcc ttttcccctc gcccgctccg cccctcccct cgcagcaccc gggcctagta
 181 ctgccgtcc cgcccctcct ctcgagcctc agcgctcagc atcgcccgga cccctcttc
 241 ccttcgcccg cctcgtcccg accctcccct tcgccccgt cccgcccgc ccctccctt
 301 cgccccgtc ccgtcccgcc ccgcccctcc ccttcgcccc cgtccctccc cttgccccc
 361 gtccctccgc gcgtgcgcgt tcgccttcga gcgcatgccc gcatctgctg tccgacaggc
 421 ggaagacgag cccagaggcg gagcagggcc gtcgcgcctt ggtgacgtct gccgccggcg
 481 cgggcgggtg acgcgactgg gcccgttgtc tgtgtgtggg actgaggggc ccgggggcg
 541 gtgggggctc ccggtggggg cagcggtggg gagggagggc ctggacatgg cgctgagggg
 601 ccgccccgcg ggaagatgaa taagggctgg ctggagctgg agagcgaccc aggtgaggag
 661 gggaccggga gggccagggg ctgggaggc cggatgggcc cgggacgcgc ctgcctgacc
 721 atcacccccct cctcttgtcg ccccacccag gcctcttcac cctgctcgtg gaagatttcg
 781 gtaagagcct tttctccctg ccggaccggg gctgtggcgg cccaccctg cgccctcact
 841 catcagggc tgtccttccc tactgctttc ctttcctcat cgcaggtgtc aaggggtgc
 901 aagtggagga gatctacgac cttcagagca aatgtcaggg gtgagtggct gtacaccagg
 961 gctgcccctt acacccagag tgctggggaa ggtcccagag aacagggccc cttagggaag
1021 acagtgccag gaacccacg ttgtaaaatc tcacagaaag cagcagcctt gctctctgag
1081 tgcccgctcc tgatcaaact gatactttct tttctcccaa actttcctta gcgcttccct
1141 ttttgtagca gcccctccc caccctaag catcctttgg ttcagctgct ttcctggcct
1201 tgcagcggga agacccggt cacacaatgt cttttgtgca gttgtgtaat gtattaattt
1261 tagtgtgccc atgtgtcctt ggctttaatc ctgacacaaa gtcatcctgt attgattggt
1321 tggggtgaca aggcccctcc tgggtgccca cacttagagt cttttcccag tggtcctgca
1381 gaatagatgt gtaagagagt agcaacagta gcaaccgtga ctgaaccaag aagtctactt
1441 taatttcctg gaacaaaaga gactggtgtg ggtgttcatt tgctttcctg actgcattgg
1501 ggcccacaag tgagaaggag tgcctcagtt cctcatcaga gtttttgttc ttgtcttact
1561 ttgtgttcct accctgtccc atccttggcc ctcagttcca gcttttcttc tcttacccag
1621 aactatagac ttcataagga gactggtgg actcctggag catcacagtc agaggcttat
1681 gctttgctct gcctgtggca ggcctttggt gtgtgagggc acaaggccac ttcagacaca
1741 gtgttgggaa gaagccaggg gagaggggg atcacagcaa ggacacctga gtgatgacgc
1801 agtgcaaagg attaatggga gaaagaaggg aatgctgatt gtcttctccc ctttggctga
```

FIG. 19A

```
1861 tctggctctg ccccttactt cccccagccc tgtatatgga tttatcttcc tgttcaaatg
1921 gatcgaagag cgccggtccc ggcgaaaggt ctctaccttg gtggatgata cgtccgtgat
1981 tgatgatgat attgtgaata acatgttctt tgcccaccag gtctgctgga ctctgtgctt
2041 tgtttggagg gtgggatgct gccatgtttt tgcttgggaa gtggaaatgg aggaagacag
2101 gaggaggaga taggcagatt ctagggtgg tagctacaga aatcctctgg cagaacgaac
2161 tgaactctta attcattaaa gggaacagct ttagagtagg agggtgtctg agtccactct
2221 ctgtgtcctc agatatccag tgggtatttg gtaggtgctt gttaaatgaa taaacattag
2281 gcaaagatga aaggagctga aaggggagt tgtccagata tgactgacct gctctggatc
2341 cccattcttg atgtatatgg gcttggggct tgcagtgagg ggtgctgtgt atgggtgact
2401 attcttggtt tcacagctga tacccaactc ttgtgcaact catgccttgc tgagcgtgct
2461 cctgaactgc agcagcgtgg acctgggacc caccctgagt cgcatgaagg acttcaccaa
2521 gggtttcagc cctgaggtag gctgcagtgc cttcatcctg gctcacagcc aactgggcag
2581 atctgaccct gagggccact gggaatgcta ccacatgata ttgggtacta ttaggctgtt
2641 tcttttcaa atgattgttt atgttacatt tgactcttaa ataaattgtg taaggccatt
2701 gttttagat gcagttgcgg ggaaaggaca caggcctagg gagggaggag agtttcctta
2761 agtcagacca tgtcagaacc ttctctgtca ggacttttcc tctcaggcca tgttgcttcc
2821 tagtgtccac taattaccat gcaaggccag cacagtccat ctctttgggg ctccagagct
2881 cttttctgcc cccaccagcc ttttaagaaa gttcgtctgt gttccttccg attcctggaa
2941 tgcctccagg ctgctctctg aagctttgcc ttccaccat agtcctacct gaggagaaat
3001 tattctgata cggccttatt ttcttccccg tagagcaaag gatatgcgat tggcaatgcc
3061 ccggagttgg ccaaggccca taatagccat gccaggtgtg tgggagctgt gggagctgat
3121 gtggggtggg agtaggggga gtatcatttt ttgggccctg actctgtttt tccccaggcc
3181 cgagccacgc cacctccctg agaagcagaa tggccttagt gcagtgcgga ccatggaggc
3241 gttccacttt gtcagctatg tgcctatcac aggccggctc tttgagctgg atgggctgaa
3301 ggtctacccc attgaccatg gtaggcacca tgagctggag gccgttggg tgtctctgcc
3361 tacctcctag ggagctgggg ctcagggccc tctggtatgt ggtacccagt ggcaggggtt
3421 gtcggtaccg cacccggct ctggctgggg tttcacccta caccatattg cccgaccagc
3481 tcctgattcc ctggctcaac tgctcttctc tgtcttcctt cccactcctg gcctgcccaa
3541 actcagggtt tccttctcgc tgattccttg tcttggtctc cactagggcc ctgggggag
3601 gacgaggagt ggacagacaa ggcccggcgg gtcatcatgg agcgtatcgg cctcgccact
3661 gcagggtaag ggccctgtgc ctgccctgtt ctactctctg gagctgtacc tactttggga
```

FIG. 19B

```
3721 gggacagaga gtatccaggt gatttgtaaa ttgcaaggcc atatggtgaa tctggcaaga
3781 tcaggcttag atcatgggtt ctcaacttgt tgtcttattt cctgcctggg ctgcctgtgg
3841 cctgctcctg ggtgggctgg gggaggggca ggcctcagtg gagccttagg cagcccaggt
3901 ctgctggttc acttccagat aggcccctca tacagcttgt tggaaggtac cagctcaggt
3961 gcctggcatg tatggctagt cgctgcctgc ctgttggggt ggggcctata cctacagctg
4021 caggtgtgac tgcagggagc cctgccagga tatctgcctc aacctgatgg cggggccggg
4081 gcgggagctg ctctcacggc tgcggctgtg actgcaggga gccctaccac gacatccgct
4141 tcaacctgat ggcagtggtg cccgaccgca ggatcaagta tgaggccagg ctgcatgtgc
4201 tgaaggtgaa ccgtcagaca gtactagagg ctctgcagca ggtaggtgcc ctttcttcct
4261 ggcctctgcc cagcccaacc ctccctgcat tcctcctccc ttccccaca gcatttgtct
4321 ctgattcgtg aacatactct cttgtagatc tgggcttcag ctaaccacat cttttctttg
4381 ccccattgt gggaaggtg ggacttggag tggggaggga gaatagcttc taaaaggaag
4441 tttgggtttg ggtgttttat ttccctgtga gtgaatgggt agagccaagg ccattattcc
4501 tttaggtcct cagcccttag ctatttaagg tagaagcccg ggtctaccct ttctcctctg
4561 agccctggat tctgttgtta gctgataaga gtaacacagc cagagctgat tcagacccac
4621 aagtctcaag agtcacagct gcctgaggag tccaagtcag ccagcaacaa gtccccgctg
4681 gtgctggaag caaacagggc ccctgcagcc tctgagggca accacacagg tactgggggg
4741 tttgggacct cttgtggacc tcagagccac ccgctaatgt ctgacatggg aggcctaaac
4801 agggaaagtc ttttctggg gatgtccttg ggcagtgttc ttccccgtc agaaggtaga
4861 gggagagcag tccttccta aagaaaggca cctgtaaagg gccgctgtta ccacaggccc
4921 ctgggcctt ctctgtaatg tacactccct ttcttgttt ctctagaggc ggttttttt
4981 tttttttttt tttttttttt tcttcctgct tctttttcc catctcattc tttgccctgt
5041 ctcattgcgg gatcatgact tagagcttgc tgactcccat tgcaccagct ggctgggctg
5101 ttcttctctg ggaagtgctg gttcacaggg ccggggagac tgtgagcttt tcttggagat
5161 cctactggag gtcctgcctg tgttcttgcc ctgtctcaga tggtgcagag gaggcggctg
5221 gttcatgcgc acaagcccca tcccacagcc ctcccaacaa acccaagcta gtggtgaagc
5281 ctccaggcag cagcctcaat ggggttcacc ccaaccccac tcccattgtc cagcggctgc
5341 cggcctttct agacaatcac aattatgcca agtccccat gcaggtaagc tgggagcacc
5401 cttgcaggat tctctacttg attctcttga gaggctgcaa caggcaattt tcccatgtgg
5461 ttccttggtg ttcatccttg gcatggctgg gtcaagctgc ctgggcctgg gttgctaggt
5521 tcctctgcct gatatgaaaa ggccccaca acagcaggag cttagggagg cagggagagc
5581 tcctttgaat ttaatctagt tacgtggctg tgggattaaa tgtttaggtc acgctccttg
```

FIG. 19C

```
5641 gtacaacttc atgggttggg ttttactggc aaaataaagg catgtgtttc agggcactct
5701 gtttctctta aaacccctcc gtggggttct atccagtgta agtgggtggc agcctcccca
5761 caagccaagg acaggccatg aacagctgg aggggttccg ctgactcagt ctggaaaacc
5821 atgttggctt tctctctggc tgtgagtgtc taggctcagc ctgggccgag cagcacttgt
5881 ttgtaactgc cctggtcttt gtcccaggag gaagaagacc tggcggcagg tgtgggccgc
5941 agccgagttc cagtccgccc accccagcag tactcagatg atgaggatga ctatgaggat
6001 gacgaggagg atgacgtgca aacaccaac tctgcccta ggtcagccca gctttctaag
6061 gctaccaggt tctaggtgct tcggatccca tcctgaatat ctcagtctgt gtctgagaat
6121 gccctgcagc agataatgtt gagcacctgc ggagtttggg gcctggggg aggctggcat
6181 gatgggctg accccaggtc cccaggaagt ttttggtggg ctgggggta aggctgagca
6241 cgtaagctta tatcatgtcc tattggaagt ggccttttag ccaggccttg aaggattggt
6301 tggggcaggg atggaggaga tgtgggtggt ggggaggcag ctttgctgga acacagggca
6361 ttggcaaaag gccaggagtg ggatggctgg aatagaggaa gtgtcttttg aggacacttg
6421 gctgcagctg tcagaacttg atgccaggct tagcatggct agttcaagtt gcttggacca
6481 agtataagga gttttagggt cagcccctgg aggtcgggat gtatttaagc cattctgggt
6541 actgctgggt atggtcacct ggcccgttcc cttgcttcac atcttctcgg gccccacagg
6601 tataagggga agggaacagg gaagccaggg gcattgagcg ttctgctga tgggcaactg
6661 tcagtgctgc agcccaacac catcaacgtc ttggctgaga agctcaaaga gtcccagaag
6721 gacctctcaa ttcctctgtc catcaagact agcagcgggg ctgggagtcc ggctgtggca
6781 gtgcccacac actcgcagcc ctcacccacc cccagcaatg agagtacaga cacggcctct
6841 gagatcggca gtgctttcaa ctcgccactg cgctcgccta tccgctcagc caacccgacg
6901 cggccctcca gccctgtcac ctcccacatc tccaaggtgc ttttggaga ggatgacagc
6961 ctgctgcgtg ttgactgcat acgctacaac cgtgctgtcc gtgatctggg tcctgtcatc
7021 agcacaggcc tgctgcacct ggctgaggat ggggtgctga gtccctggc gctgacaggt
7081 gggccttgga ctggctcact ggccacttgg tgcacccagg agggaggagg gaagtggcca
7141 agtgaccaca aagtgtcctg cactctgatg attttcttgt gacctctctt cccagagggt
7201 gggaagggtt cctcgccctc catcagacca atccaaggca gccaggggtc cagcagccca
7261 gtggagaagg aggtcgtgga agccacggac agcagagaga agacggggat ggtgaggcct
7321 ggcgagccct tgagtgggga gaaatactca cccaggtga gcctccgttg tggttttctc
7381 ctttaatcct ggcagagggt aaggcctgag ctcctcctgc ccaggtgcca agttcttgat
```

FIG. 19D

```
7441 tggaactttg gtgtgaagat tggtggctgg agccatgtgc cagaagactt tctgggttgg
7501 gtggtggcag gggccttgat aggcatggac tcgctgctca tccttgcctc tagctgccta
7561 ttgctcgtgg ggctttgttg ctggcccgcc ccgatcagag gtgcaatgct gggttttggc
7621 aggagctgct ggcactgctg aagtgtgtgg aggctgagat tgcaaactat gaggcgtgcc
7681 tcaaggagga ggtagagaag aggaagaagt tcaaggtggg tgatttctcc agttgcctga
7741 tctggcctct cccgaggtcc actggtggct gctctggcaa gattggctcc agtgctctca
7801 gtcttcttct ctcctacaga ttgatgacca gagaaggacc cacaactacg atgagttcat
7861 ctgcaccttt atctccatgc tggctcagga ggtgagggg atgcgctgct gtcttaactg
7921 gaatgccctg ctgagggccg tgtccttcag ctcccctccc ctggcctctc ctgaggcttg
7981 agcagacctt ggggcacagg gagggccatg agagcctcag ctcctggcct gaggcagcca
8041 gcacctgctc aagggtctct acctcttcgc aggcatgctg gccaacctag tggagcagaa
8101 catctccgtg cggcggcgcc aaggggtcag catcggccgg ctccacaagc agcggaagcc
8161 tgaccggcgg aaacgctctc gccctacaa ggccaagcgc cagtgaggac tgctggccct
8221 gactctgcag cccactcttg ccgtgtggcc ctcaccaggg tccttccctg ccccacttcc
8281 ccttttccca gtattactga atagtcccag ctggagagtc caggccctgg gaatgggagg
8341 aaccaggcca cattccttcc atcgtgccct gaggcctgac acggcagatc agccccatag
8401 tgctcaggag gcagcatctg gagttggggc acagcgaggt actgcagctt cctccacagc
8461 cggctgtgga gcagcaggac ctggcccttc tgcctgggca gcagaatata tattttacct
8521 atcagagaca tctattttc tgggctccaa cccaacatgc caccatgttg acataagttc
8581 ctacctgact atgctttctc tcctaggagc tgtcctggtg ggcccaggtc cttgtatcat
8641 gccacggtcc caactacagg gtcctagctg ggggcctggg tgggccctgg gctctgggcc
8701 ctgctgctct agccccagcc accagcctgt ccctgttgta aggaagccag gtcttctctc
8761 ttcattcctc ttaggagagt gccaaactca gggacccagc actgggctgg gttgggagta
8821 gggtgtccca gtggggttgg ggtgagcagg ctgctgggat cccatggcct gagcagagca
8881 tgtgggaact gttcagtggc ctgtgaactg tcttccttgt tctagccagg ctgttcaaga
8941 ctgctctcca tagcaaggtt ctagggctct tcgccttcag tgttgtggcc ctagctatgg
9001 gcctaaattg ggctctaggt ctctgtccct ggcgcttgag gctcagaaga gcctctgtcc
9061 agcccctcag tattaccatg tctccctctc aggggtagca gagacagggt tgcttatagg
9121 aagctggcac cactcagctc ttcctgctac tccagtttcc tcagcctctg caaggcactc
```

FIG. 19E

```
9181  agggtggggg acagcaggat caagacaacc cgttggagcc cctgtgttcc agaggacctg
9241  atgccaaggg gtaatgggcc cagcagtgcc tctggagccc aggccccaac acagccccat
9301  ggcctctgcc agatggcttt gaaaaaggtg atccaagcag gcccctttat ctgtacatag
9361  tgactgagtg gggggtgctg gcaagtgtgg cagctgcctc tgggctgagc acagcttgac
9421  ccctctagcc cctgtaaata ctggatcaat gaatgaataa aactctccta agaatctcct
9481  gagaaatgaa ccctcctgtg gttgctggcc tgagatatgg aggctgggcc ttactagacc
9541  tcatgggcct agggccctgg gaccagaaag gtaagaagta tatgatcctt gagtgtccag
9601  ctgtcttggg ccagagatcc ttggaatcct aggcctggga tttaggacct gagctgagga
9661  gggacttcag gtggactgta gacagggtgc actttctggg gagagggcca tggctttcac
9721  caaatctgtg gctttgcagc ctggagaggt gctgggactg tgggtcaaag aggcgggct
9781  gcctctaatc taatctcgcc tggtgtgttc tccctgggag ggcgctgggc atctcttcct
9841  tgttgctttt ggacaggtaa agcaggtcaa agctgccgcc tctgtcccgc tctcctctgc
9901  cgactgcatc gtctgctgag gctgctgcag cccctcacca gcccctggc agtgagtcct
9961  gcagagggt cctcatgcaa gca
```

FIG. 19F

COMPOSITIONS AND METHODS FOR DETECTING CANCER METASTASIS

CROSS REFERENCE TO RELATED APPLICATIONS

This application claims the priority of U.S. provisional application No. 61/385,696, filed Sep. 23, 2010, which is hereby incorporated by reference in its entirety.

GOVERNMENTAL RIGHTS

This invention was made with government support under R01 CA125970 awarded by the National Cancer Institute, and under P30 EY02687c and AR007279-31A1 awarded by the National Institutes of Health. The government has certain rights in the invention.

REFERENCE TO SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821 (f).

FIELD OF THE INVENTION

The invention encompasses compositions and methods for detecting cancer metastasis.

BACKGROUND OF THE INVENTION

Once a primary tumor has metastasized and is clinically detectable by current diagnostic measures, treatment of the tumor becomes more complicated, and generally speaking, survival rates decrease. Consequently, it is advantageous to determine which tumors are more likely to metastasize and to advance the time to detection of metastasis, so that appropriate treatment may be started as soon as possible. Many different types of tumors are capable of metastasizing. Melanomas, in particular, are capable of aggressive metastasis.

Melanoma is a malignant tumor of melanocytes, and may occur in the eye (uveal melanoma), on the skin, or on mucosal tissues. Uveal melanoma is the most common intraocular malignancy. The incidence of this tumor increases with age and reaches a maximum between the $6^{th}$ and $7^{th}$ decade of life. Approximately 50% of patients die of metastases, a proportion that, despite all efforts to improve treatment, has remained constant during the last century. The average life expectancy after diagnosis of metastases is 7 months.

Around 160,000 new cases of melanoma of the skin are diagnosed worldwide each year, and according to the WHO Report about 48,000 melanoma related deaths occur worldwide per annum, which accounts for 75 percent of all deaths associated with skin cancer. Similar to uveal melanoma, when there is distant metastasis, the cancer is generally considered incurable. The five-year survival rate is less than 10%, with a median survival time of 6 to 12 months. Additionally, specific to uveal melanoma and cutaneous melanoma and generally considered for carcinoma, earlier treatment of malignancies is associated with improved progression-free and overall survival.

Due to the aggressive nature of these malignancies, there is a need in the art for methods of predicting the risk of metastasis and for earlier detection of metastatic disease, so that treatment may begin as early as possible.

SUMMARY OF THE INVENTION

One aspect of the present invention encompasses a method for determining the risk of metastasis in a subject. Generally speaking, the method comprises collecting a sample from a subject, analyzing the BAP1 nucleotide and/or BAP1 amino acid sequence from a cell in the sample, and identifying the presence of a mutation in the BAP1 nucleotide and/or BAP1 amino acid sequence. The presence of the mutation indicates an increased risk for metastasis in the subject.

Another aspect of the invention encompasses a method for determining the risk of metastasis in a subject, where the method comprises determining the level of BAP1 activity in a sample from a subject, wherein in decreased BAP1 activity indicates an increased risk for metastasis in the subject.

Still another aspect of the present invention encompasses a method for detecting the presence of metastatic cancer. Generally speaking, the method comprises collecting a sample from a subject, analyzing the BAP1 nucleotide and/or BAP1 amino acid sequence in the sample, and determining the presence of a mutation in the BAP1 nucleotide and/or BAP1 amino acid sequence. The presence of the mutation indicates the presence of metastatic melanoma.

Yet another aspect of the present invention encompasses a method for detecting the presence of metastatic cancer, the method comprising determining the level of BAP1 activity in a sample from a subject, wherein decreased BAP1 activity indicates the presence of metastatic cancer in the subject.

Still yet another aspect of the present invention encompasses a method for detecting the presence of a biomarker for metastatic cancer in a subject. The method may encompass a method for determining the risk of metastasis in a subject. Generally speaking, the method comprises analyzing the BAP1 gene nucleotide sequence and/or the BAP1 protein amino acid sequence from a tumor cell in a sample obtained from the subject, and identifying the presence of a mutation in the BAP1 nucleotide sequence and/or BAP1 protein sequence. The presence or absence of a mutation is as compared to the gene and/or protein sequence from a non-tumor cell from the same subject. For example, the gene nucleotide and/or protein amino acid sequence from a non-tumor cell may be SEQ ID NOs:3 and 1, respectively. Comparison may also be made between cDNA obtained from mRNA from a tumor cell and cDNA obtained from mRNA from a non-tumor cell, which may have BAP1 nucleotide sequence SEQ ID NO:2. The presence of a mutation, particularly an inactivating mutation as defined elsewhere herein, indicates an increased risk for metastasis in the subject.

The biomarker may be decreased BAP1 activity in a tumor cell from a subject, as compared to the activity in a non-tumor cell from the same subject. Decreased BAP1 activity may be indicative of an increased risk of metastasis in the subject and/or of the presence of metastatic cancer.

Certain aspects of the present invention encompass a method for detecting the presence of metastatic cancer. Generally speaking, the assay comprises analyzing the BAP1 gene nucleotide sequence or the BAP1 protein amino acid sequence in a tumor sample obtained from the subject, and detecting the presence of a mutation in the BAP1 nucleotide sequence or BAP1 protein sequence, as compared to the sequence in a non-tumor sample from the subject, as mentioned above. The presence of the mutation indicates the presence of metastatic melanoma.

Several aspects of the present invention encompasses a metastatic cancer biomarker, which may be detected in a tumor sample obtained from a subject. The biomarker typically comprises a BAP1 nucleotide sequence comprising at least one mutation, as compared to the BAP1 sequence in a non-tumor sample from the subject. The biomarker may also comprise a BAP1 amino acid sequence comprising at least one mutation. Such a biomarker may be detectable, for example, by use of an antibody which specifically recognizes the biomarker and such antibodies are also encompassed by the present invention. The biomarker may be detected by detecting reduced BAP1 activity in a cell from tumor sample from a subject, as compared to the activity in a cell from a non-tumor sample from the same subject.

Other aspects and iterations of the invention are described more thoroughly below.

REFERENCE TO COLOR FIGURES

The application file contains at least one photograph executed in color. Copies of this patent application publication with color photographs will be provided by the Office upon request and payment of the necessary fee.

BRIEF DESCRIPTION OF THE FIGURES

FIG. 19 panels A-F depict the genomic sequence of BAP1. Exons are bolded, and select mutations are highlighted (see Table 2).

DETAILED DESCRIPTION OF THE INVENTION

Figure 1A:
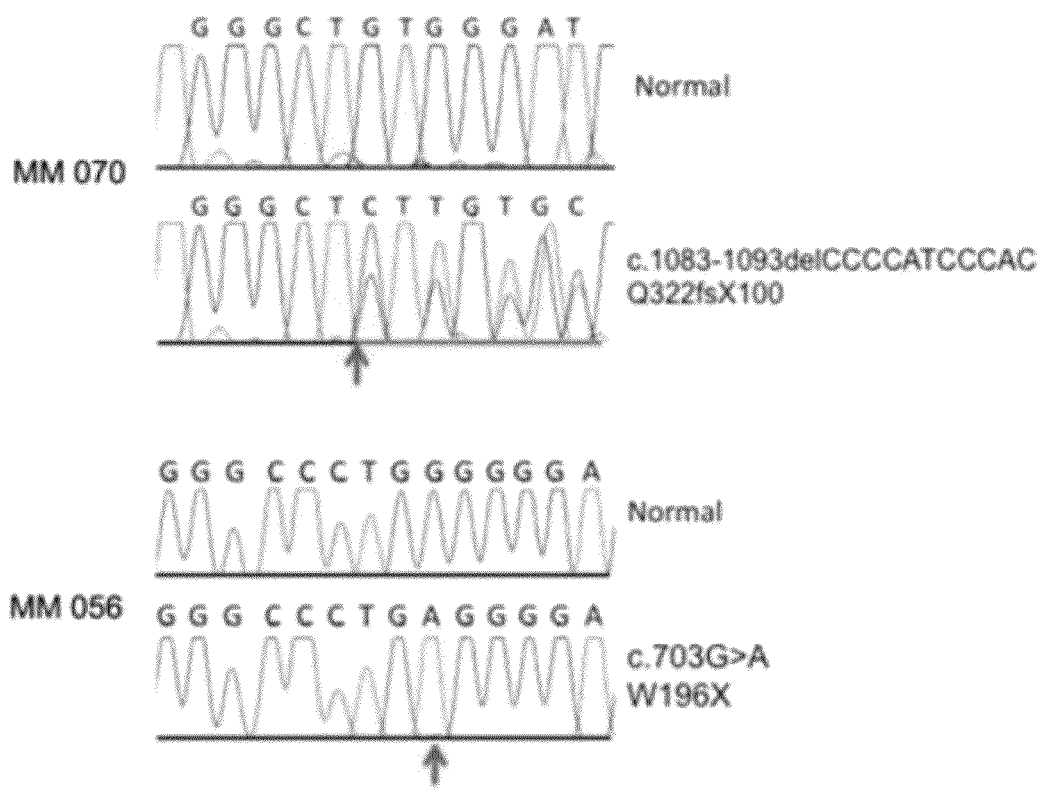
FIG. 1 depicts a series of panels illustrating that inactivating mutations in BAP1 occur frequently in uveal melanomas. (A) Sanger sequence traces of MM 056 and MM 070 at the sites of the mutations. Location of mutated base in MM 056 and the start of the deletion of MM 070 are indicated (arrows). The non-coding BAP1 strand is shown for MM 070. (SEQ ID NO:s 44-47) (B) Map of BAP1 gene and location of BAP1 mutations. BAP1 contains 17 exons (shaded boxes) that encode a 728 amino acid protein. Introns are not to scale. Mutations are shown below the gene figure as indicated. The UCH domain (aa. 1-188) and UCH37-like domain (ULD) (aa. 635-693) are indicated (12, 13). The critical Q, C, H and D residues of the active site (Gln85, Cys91, His169 and Asp184) are indicated with asterisks. The catalytic cysteine is indicated with a circle. Also shown are: the NHNY consensus sequence for interaction with HCFC1 (aa. 363-365, exon 11), nuclear localization signals (NLS) at aa. 656-661 (exon 15) and aa. 717-722 (exon 17), the BARD1 binding domain within the region bounded by aa. 182-240 (13), and the BRCA1 binding domain within aa. 598-729 (11). (C) Location of BAP1 gene missense mutations in the UCH domain aligned to the crystal structure of UCH-L3 (21). Three-dimensional structure of UCH-L3 was visualized with MMDB software (22). The small molecule near C91W, H169Q and S172R represents a suicide inhibitor, illustrating the critical location of these mutations for catalytic activity. (D) Conservation of BAP1 in regions containing mutated amino acids. Alignments of segments of BAP1 homologs harboring mutated amino acids (missense or in-frame deletions) are shown for the indicated species. (SEQ ID NO:48-60) Amino acid numbering is on the basis of human BAP1 (SEQ ID NO:1). Positions of mutated amino acids are indicated with asterisks.

The present invention provides a method for determining the risk of tumor metastasis in a subject. Additionally, the invention provides a method for detecting the presence of a tumor metastasis in a subject. The invention further provides a method for detection of a metastatic cancer biomarker in a subject, wherein detection of the biomarker comprises identifying a mutation in a BAP1 nucleotide sequence, identifying a mutation in a BAP1 protein sequence, or identifying a decrease in BAP1 activity in a sample obtained from the subject. Advantageously, such methods may allow a physician to determine the severity of an oncogenic disease in a subject and to make appropriate, timely, treatment decisions based on this information.

I. Method for Determining the Risk of Tumor Metastasis

One aspect of the present invention encompasses a method for determining the risk of tumor metastasis in a subject. In one embodiment, the method comprises collecting a sample from a subject, analyzing the BAP1 nucleotide and/or BAP1 amino acid sequence from a cell in the sample, and identifying the presence of a mutation in the BAP1 nucleotide sequence and/or the BAP1 amino acid sequence. In this context, "a mutation in the BAP1 nucleotide sequence," refers to a mutation in an exon of BAP1, an intron of BAP1, the promoter of BAP1, the 5' untranslated region of BAP1, the 3' untranslated region of BAP1, or any other regulatory region for the BAP1 gene, such that the mutation decreases the expression of BAP1 mRNA, synthesis of BAP1 protein, or enzymatic activity of BAP1 when compared to the sequence of BAP1 from a non-tumor cell of the same individual. The presence of such a BAP1 mutation indicates an increased risk for metastasis in the subject. Nucleotide and amino acid sequence mutations in tumor cells are detected by comparison with the equivalent sequences from non-tumor cells from the same subject and/or by comparison to human wild type sequences SEQ ID NO:3 (genomic nucleotide sequence) and SEQ ID NO:1 (amino acid sequence). A mutation may also be identified by comparing cDNA sequences obtained from mRNA in a tumor and non-tumor cell. "Wild type" cDNA may have the sequence SEQ ID NO:2.

In another embodiment, the method comprises collecting a sample from a subject, and analyzing the level of BAP1 activity in the sample, where a decrease in BAP1 activity indicates an increased risk for metastasis in the subject.

Each of these embodiments are discussed in more detail below.

(a) Analyzing the BAP1 Sequence to Determine Risk of Tumor Metastasis

One embodiment comprises analyzing the BAP1 nucleotide sequence and/or BAP1 amino acid sequence of a sample collected from a subject as described in section (c) below. Typically, analyzing the BAP1 nucleotide sequence may comprise identifying a mutation in the BAP1 nucleotide sequence. As detailed above, "a mutation in the BAP1 sequence," refers to a mutation in an exon of BAP1, an intron of BAP1, the promoter of BAP1, the 5' untranslated region of BAP1, the 3' untranslated region of BAP1, or any other regulatory region for the BAP1 gene (e.g. a splice acceptor site), such that the mutation decreases the expression of BAP1 mRNA, synthesis of BAP1 protein, or enzymatic activity of BAP1 when compared to the sequence of BAP1 from a non-tumor cell of the same individual. Such a mutation may be a point mutation, a deletion mutation, or an insertion mutation. The mutation may be a missense or nonsense mutation. For instance, in one embodiment, the mutation may cause a premature truncation of BAP1. Alternatively, the mutation may affect a conserved amino acid in the ubiquitin carboxy-terminal hydrolase (UCH) domain or the UCH37-like domain (ULD) (for instance, see FIG. 1B). Such a mutation may be identified using methods commonly known in the art. For instance, see the Examples. Generally speaking, all or a portion of the BAP1 nucleic acid sequence may be sequenced and compared to the wild-type genomic sequence (SEQ ID NO:3) to identify a mutation. Alternatively or additionally, all or a portion of the BAP1 amino acid sequence may be compared to the wild-type amino acid sequence (SEQ ID NO:1) to identify a mutation. Alternatively or additionally, all or a portion of cDNA obtained from BAP1 mRNA may be compared to the cDNA nucleotide sequence (RefSeq #NM_004656; SEQ ID NO:2).

However, with the knowledge of the mutations provided herein, it is a routine matter to design detection means such as primers and/or probes that would be able to detect and/or identify mutated sequences, such as mutated nucleotide sequences which differ from the wild-type SEQ ID NO:3 (or SEQ ID NO:2, if cDNA is being examined), or mutated nucleotide sequences which differ from the BAP1 nucleotide sequence from a non-tumor cell of the subject. Possible techniques which might be utilized are well-established in the prior art and their use is readily adaptable by the skilled person for the purposes of detecting the BAP1 gene and/or BAP1 protein mutations disclosed herein. For example, amplification techniques may be used. Non-limiting examples of amplification techniques may include polymerase chain reaction, ligase chain reaction, nucleic acid sequence based amplification (NASBA), strand displacement amplification (SDA), transcription mediated amplification (TMA), Loop-Mediated Isothermal Amplification (LAMP), Q-beta replicase, Rolling circle amplification, 3SR, ramification amplification (Zhang et al. (2001) Molecular Diagnosis 6 p 141-150), multiplex ligation-dependent probe amplification (Schouten et al. (2002) Nucl. Ac. Res. 30 e57). Other related techniques for detecting mutations such as SNPs may include restriction fragment length polymorphism (RFLP), single strand conformation polymorphism (SSCP) and denaturing high performance liquid chromatography (DHPLC). A summary of many of these techniques can be found in "DNA Amplification: Current technologies and applications" (Eds. Demidov & Broude (2004) Pub. Horizon Bioscience, ISBN: 0-9545232-9-6) and other current textbooks.

A mutation of BAP1 may be an inactivating mutation, i.e., expression levels of BAP1 mRNA and/or synthesis of BAP1 protein are reduced and/or BAP1 protein activity is reduced in cells from a tumor sample from a subject, compared to expression level and/or synthesis level and/or activity in cells from a non-tumor sample from the same subject. BAP1 protein activity may be, for example, ubiquitin carboxy-terminal hydrolase activity.

In one embodiment, a mutation of BAP1 may be found in exon 1, 2, 3, 4, 5, 6, 7, 8, 9, 10, 11, 12, 13, 14, 15, 16, 17, 18, 19, or 20 of the BAP1 nucleotide sequence. In another embodiment, a mutation of BAP1 may be found in the promoter of BAP1. In yet another embodiment, a mutation of BAP1 may be found in the 5' untranslated region. In still another embodiment, a mutation of BAP1 may be found in the 3' untranslated region. In a certain embodiment, a mutation of BAP1 may be found in a splice acceptor site.

In particular embodiments, a mutation may be selected from one or more of: deletion of the nucleotides equivalent to positions 3025-3074 of SEQ ID NO:3; deletion of the nucleotides equivalent to positions 2026-2028 of SEQ ID NO:2; substitution of the nucleotide cytosine with the nucleotide guanine at the position equivalent to position 622 of SEQ ID NO:2; substitution of the nucleotide guanine with the nucleotide adenine at the position equivalent to position 703 of SEQ ID NO:2; substitution of the nucleotide cytosine with the nucleotide thymine at the position equivalent to position 872 of SEQ ID NO:2; deletion of the nucleotides equivalent to positions 960-968 of SEQ ID NO:2; deletion of the nucleotides equivalent to positions 1083-1093 of SEQ ID NO:2; substitution of the nucleotide adenine with the nucleotide guanine at the position equivalent to position 2130 of SEQ ID NO:2; deletion of the nucleotides equivalent to positions 3313-3335 of SEQ ID NO:3; deletion of the nucleotides equivalent to positions 736-751 of SEQ ID NO:2; insertion of the nucleotide adenine between positions equivalent to positions 1318 and 1319 of SEQ ID NO:2; deletion of the nucleotides equivalent to positions 468-487 of SEQ ID NO:2 and insertion of the nucleotide adenine; deletion of nucleotide adenine at the position equivalent to position 874 of SEQ ID NO:2; deletion of the nucleotides equivalent to positions 726-759 of SEQ ID NO:3; substitution of the nucleotide thymine with the nucleotide adenine at the position equivalent to position 2303 of SEQ ID NO:2; deletion of the nucleotides equivalent to positions 1829-1833 of SEQ ID NO:2; deletion of nucleotide cytosine at the position equivalent to position 259 of SEQ ID NO:2; substitution of the nucleotide guanine with the nucleotide cytosine at the position equivalent to position 497 of SEQ ID NO:2; substitution of the nucleotide cytosine with the nucleotide guanine at the position equivalent to position 622 of SEQ ID NO:2; deletion of the nucleotides equivalent to positions 2112-2120 of SEQ ID NO:2; substitution of the nucleotide thymine with the nucleotide guanine at the position equivalent to position 388 of SEQ ID NO:2; deletion of the nucleotides equivalent to positions 2006-2017 of SEQ ID NO:2; deletion of the nucleotides equivalent to positions 610-634 of SEQ ID NO:2; deletion of the nucleotides equivalent to positions 739-776 of SEQ ID NO:3; substitution of the nucleotide guanine with the nucleotide thymine at the position equivalent to position 7819 of SEQ ID NO:3; substitution of the nucleotide cytosine with the nucleotide guanine at the position equivalent to position 631 of SEQ ID NO:2; deletion of the nucleotides equivalent to positions 2195-2220 of SEQ ID NO:2; substitution of the nucleotide cytosine with the nucleotide thymine at the position equivalent to position 221 of SEQ ID NO:2. As outlined above, nucleotide numbering is by reference to the human wild-type sequences, for example, as represented by SEQ ID NO:3 when comparing genomic DNA or SEQ ID NO:2 when comparing cDNA.

In a particular embodiment, a mutation may be a truncating mutation in exon 2, 3, 4, 5, 6, 7, 8, 9, 11, 13, 16 or 17 of BAP1, a missense mutation in exon 5, 6, 7 or 16, an in-frame deletion in exon 10, 15 or 16, or a termination read-through in exon 17. In another particular embodiment, a BAP1 mutation may be a nonsense mutation in a BAP1 protein encoded by the BAP1 nucleotide sequence, selected from Q36X, W196X, and Q253X. In yet another particular embodiment, a BAP1 mutation may be a missense mutation selected from C91W, G128R, H169Q, S172R or D672G. In still another particular embodiment, an in-frame deletion may be selected from the group E283-S285del, E631-A634del or R666-H669del. Amino acid numbering is by reference to the human wild type sequences, for example, as represented by SEQ ID NO:1.

(b) Analyzing the Level of BAP1 Activity

In other embodiments of the invention, the level of BAP1 activity in a sample is analyzed. The "level of BAP1 activity" may refer to the level of expression of BAP1 mRNA, the level of synthesis of BAP1 protein, or the level of enzymatic activity of BAP1 in a sample.

In one embodiment, the level of BAP1 activity may refer to the level of expression of BAP1 mRNA in a sample. Generally speaking, if a sample has a decreased level of expression of BAP1 mRNA, then the subject has an increased risk of metastasis. In certain embodiments, the level of BAP1 activity is decreased about 50% to about 100% compared to a non-tumor cell from the same individual. In other embodiments, the level of BAP1 activity is decreased from about 60% to about 100% compared to a non-tumor cell from the same individual. In still other embodiments, the level of BAP1 activity is decreased from about 70% to about 95% compared to a non-tumor cell from the same individual. In certain embodiments, the level of BAP1 activity is decreased about 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, or 50% compared to a non-tumor cell from the same individual.

Determining the level of expression of a BAP1 nucleic acid sequence, comprises, in part, measuring the level of BAP1 mRNA expression in a tumor sample. Methods of measuring the level of mRNA in a tumor sample for a particular nucleic acid sequence, or several sequences, are known in the art. For instance, in one embodiment, the level of mRNA expression may be determined using a nucleic acid microarray. Methods of using a nucleic acid microarray are well and widely known in the art. In another embodiment, the level of mRNA expression may be determined using PCR. In these embodiments, the mRNA is typically reverse transcribed into cDNA using methods known in the art. The cDNA may, for example, have nucleotide sequence SEQ ID NO:2 when derived from mRNA obtained from a non tumor cell. Methods of PCR are well and widely known in the art, and may include quantitative PCR, semi-quantitative PCR, multi-plex PCR, or any combination thereof. Other nucleic acid amplification techniques and methods are suggested above. In yet another embodiment, the level of mRNA expression may be determined using a TLDA (TaqMan low density array) card manufactured by Applied Biosciences, or a similar assay. The level of mRNA expression may be measured by measuring an entire mRNA transcript for a nucleic acid sequence, or measuring a portion of the mRNA transcript for a nucleic acid sequence. For instance, if a nucleic acid array is utilized to measure the level of mRNA expression, the array may comprise a probe for a portion of the mRNA of the nucleic acid sequence of interest, or the array may comprise a probe for the full mRNA of the nucleic acid sequence of interest. Similarly, in a PCR reaction, the primers may be designed to amplify the entire cDNA sequence of the nucleic acid sequence of interest, or a portion of the cDNA sequence. One of skill in the art will recognize that there is more than one set of primers that may be used to amplify either the entire cDNA or a portion of the cDNA for a nucleic acid sequence of interest. Methods of designing primers are known in the art.

Methods of extracting RNA from a tumor sample are known in the art. For instance, see Examples 1 and 2 of PCT/US09/041,436, herein incorporated by reference in its entirety.

The level of expression may or may not be normalized to the level of a control gene. Such a control gene should have a constant expression in a tumor sample, regardless of the risk for metastasis of the tumor. This allows comparisons between assays that are performed on different occasions.

In another embodiment, the level of BAP1 activity may refer to the level of BAP1 protein synthesis in a sample. Generally speaking, a decreased level of BAP1 synthesis in a sample indicates an increased risk of metastasis in the subject. Methods of measuring the synthesis of BAP1 are known in the art. For instance, immunofluorescence may be used, as described in the Examples.

In yet another embodiment, the level of BAP1 activity may refer to the level of BAP1 enzymatic activity in a sample. Generally speaking, a decreased level of BAP1 enzymatic activity indicates an increased risk of metastasis in a subject. BAP1 has ubiquitin carboxy-terminal hydrolase activity. Such activity may be measured using methods well known in the art. See, for instance, Scheuermann J C, et al: Histone H2A deubiquitinase activity of the Polycomb repressive complex PR-DUB, Nature 2010, 465:243-247 (the measurement of histone H2A monoubiquitination); Machida Y J, et al: The deubiquitinating enzyme BAP1 regulates cell growth via interaction with HCF-1, J Biol Chem 2009, 284:34179-34188 (the measurement of HCFC1 deubiquitination); Russell N S, Wilkinson K D. Deubiquitinating enzyme purification, assay inhibitors, and characterization. Methods Mol Biol 2005; 301:207-19 (other strategies for measurement of deubiquitinating enzymatic activity using substrates that can be monitored, such as described in Russell et al.).

(c) Collecting a Sample from a Subject

A method of the invention comprises, in part, collecting a sample from a subject. Suitable samples comprise one or more tumor cells, either from a primary tumor or a metastasis. In one embodiment, a suitable sample comprises a melanoma cell. In another embodiment, a suitable sample comprises a carcinoma cell. In yet another embodiment, a suitable sample comprises a sarcoma cell. In an exemplary embodiment, a suitable sample comprises a uveal melanoma cell. In another exemplary embodiment, a suitable sample comprises a cutaneous melanoma cell. In some embodiments, a suitable sample may be a circulating tumor cell. Circulating tumor cells may be found in a bodily fluid (e.g. plasma, sputum, urine, etc.) or other excrement (e.g. feces).

Methods of collecting tumor samples are well known in the art. For instance, a tumor sample may be obtained from a surgically resected tumor. In uveal melanoma, for example, a tumor sample may be obtained from an enucleation procedure. Alternatively, the tumor sample may be obtained from a biopsy. This is advantageous when the tumor is small enough to not require resection. In an exemplary embodiment, the tumor sample may be obtained from a fine needle biopsy, also known as a needle aspiration biopsy (NAB), a fine needle aspiration cytology (FNAC), a fine needle aspiration biopsy (FNAB) or a fine needle aspiration (FNA). A tumor sample may be fresh or otherwise stored so as to reduce nucleic acid degradation. For instance, a tumor sample may be a fresh frozen tumor sample or a formalin-fixed paraffin embedded tumor sample.

In certain embodiments, the method of the invention may be performed with a tumor sample comprising about five cells or less. In one embodiment, the tumor sample may comprise about 1, 2, 3, 4, 5, 6, 7, 8, 9, 10, 11, 12, 13, 14, 15 or more cells. In another embodiment, the tumor sample may comprise 20, 25, 30, 35, 40 or more cells.

(d) Determining the Risk of Metastasis

A method of the invention further comprises determining the risk of metastasis. The level of risk is a measure of the probability of a metastasis occurring in a given individual. If a mutation is indentified, as described in section (a) above, in a sample from a subject, then the subject is at a higher risk (i.e., there is an increased probability) of developing metastases then a subject without a mutation in a BAP1 nucleotide sequence and/or BAP1 amino acid sequence. Alternatively, if the level of BAP1 activity is decreased, as described in section (b) above, then the subject is at a higher risk of developing metastases then a subject with out a decreased level of BAP1 activity. For instance, the risk may be greater than about 20%, 25%, 30%, 35%, 40%, 45%, 50%, 55%, 60%, 65%, 70%, 75%, 80%, 85%, 90%, or 95%. In some embodiments, the risk may be greater than about 50%, 55%, 60%, 65%, 70%, 75%, 80%, 85%, 90%, or 95%. In particular embodiments, the risk may continue to increase over time. For example, the risk may be about 50% at five years after initial cancer diagnosis and 90% for ten years.

Alternatively, if a mutation in not identified (i.e. the BAP1 nucleotide and corresponding amino acid sequence is wild-type) in a sample from a subject, then the subject is at lower risk of developing metastases. Similarly, if the level of BAP1 activity is not decreased, then the subject is at a lower risk of developing metastasis. For instance, the risk may be less than about 95%, 90%, 85%, 80%, 75%, 70%, 65%, 60%, 55%, 50%, 45%, 40%, 35%, 30%, 25%, 20%, 15%, 10%, or 5%. In some embodiments, the risk may be less than about 20%, 15%, 10%, or 5%. In particular embodiments, the risk may be low, but may still increase over time. For example, the risk may be about 5% at five years and 10% at ten years.

Increased or decreased "risk" or "probability" may be determined, for example, by comparison to the average risk or probability of an individual cancer patient within a defined population developing metastasis. For example, by way of illustration, for a given cancer the overall proportion of patients who are diagnosed with a metastasis within 5 years of initial cancer diagnosis may be 50%. In this theoretical context, an increased risk for an individual will mean that they are more than 50% likely to develop a metastasis within 5 years, whereas a reduced risk will mean that they are less than 50% likely to develop a metastasis. Such comparisons may, in some circumstances, be made within patient populations limited or grouped using other factors such as age, ethnicity, and/or the presence or absence of other risk factors.

(e) Combination of Methods

In certain embodiments, a method of the invention may be used in conjunction with a method as described in PCT/US09/041,436, herein incorporated by reference in its entirety, to determine the risk of metastasis in a subject.

II. Method for Detecting a Metastasis

Another aspect of the present invention is a method for detecting the presence of a metastasis. In one embodiment, the method generally comprises collecting a sample from a subject, analyzing the BAP1 nucleotide and/or BAP1 amino acid sequence in the sample, and determining the presence of a mutation in the BAP1 sequence. The presence of the mutation indicates the presence of a metastasis. As outlined above, the presence of a mutation may be determined by comparison of a sequence from a tumor cell with a sequence from a non-tumor cell from the same subject and/or by comparison to SEQ ID NO:1 (wild type amino acid sequence) or SEQ ID NO:3 (wild type genomic DNA sequence). It may also be determined by obtaining cDNA from BAP1 mRNA in the cell and comparing the sequence to SEQ ID NO:2.

In another embodiment, the method comprises collecting a sample from a subject, and analyzing the level of BAP1 activity in the sample, where a decrease in BAP1 activity indicates the presence of a metastasis in the subject. Suitable samples, methods of analyzing a BAP1 nucleotide sequence and/or BAP1 amino acid sequence, and methods of determining the level of BAP1 activity in a sample are described in section I above.

III. Biomarker for Metastasis

Yet another aspect of the invention encompasses a biomarker for tumor metastasis. In one embodiment, a biomarker of the invention comprises a mutation in a BAP1 nucleotide sequence and/or BAP1 amino acid sequence, as described in section I(a) above. In another embodiment, a biomarker of the invention comprises a decreased level of BAP1 activity, as described in section I(b) above. This may include a decrease in BAP1 protein synthesis. Where the biomarker is a BAP1 amino acid sequence comprising a mutation, the presence of the biomarker may be detected by use of an antibody which specifically binds to the biomarker. Such antibodies are encompassed within the scope of the present invention, as well as kits comprising the antibody and methods of use thereof. In each of the above embodiments, a tumor may be a melanoma, carcinoma, or sarcoma. In an exemplary embodiment, the tumor is a melanoma. In a further exemplary embodiment, the tumor is a uveal melanoma. In yet another exemplary embodiment, the tumor is a cutaneous melanoma.

DEFINITIONS

As used herein, "carcinoma" refers to a malignant tumor derived from an epithelial cell. Non-limiting examples of carcinoma may include epithelial neoplasms, squamous cell neoplasms, squamous cell carcinoma, basal cell neoplasms, basal cell carcinoma, transitional cell carcinomas, adnexal and skin appendage neoplasms, mucoepidermoid neoplasms, cystic, mucinous and serous neoplasms, ductal, lobular and medullary neoplasms, acinar cell neoplasms, complex epithelial neoplasms, squamous cell carcinoma, adenosquamous carcinoma, anaplastic carcinoma, large cell carcinoma, small cell carcinoma, and adenocarcinomas such as adenocarcinoma, linitis plastica, vipoma, cholangiocarcinoma, hepatocellular carcinoma, adenoid cystic carcinoma, and grawitz tumor.

As used herein, "melanoma" refers to a malignant tumor of a melanocyte. In one embodiment, the melanoma may be a uveal melanoma. In another embodiment, the melanoma may be a cutaneous melanoma. In another embodiment, the melanoma may be a mucosal melanoma.

As used herein, "regulatory region" refers to a nucleic acid sequence operably linked to a nucleic acid encoding BAP1 such that the regulatory region modulates the transcription of BAP1 mRNA.

As used herein, "sarcoma" refers to a malignant tumor derived from connective tissue. Non limiting examples of a sarcoma may include Askin's Tumor, botryoid sarcoma, chondrosarcoma, Ewing's sarcoma, primitive neuroectodermal tumor (PNET), malignant hemangioendothelioma, malignant peripheral nerve sheath tumor (malignant schwannoma), osteosarcoma and soft tissue sarcomas such as alveolar soft part sarcoma, angiosarcoma, cystosarcoma phyllodes, dermatofibrosarcoma, desmoid Tumor, desmoplastic small round cell tumor, epithelioid sarcoma, extraskeletal chondrosarcoma, extraskeletal osteosarcoma, fibrosarcoma, hemangiopericytoma, hemangiosarcoma, Kaposi's sarcoma, leiomyosarcoma, liposarcoma. Lymphangiosarcoma, lymphosarcoma, malignant fibrous histiocytoma, neurofibrosarcoma, rhabdomyosarcoma, and synovial sarcoma.

As used herein, "subject" refers to a mammal capable of being afflicted with a carcinoma, melanoma, or sarcoma, and that expresses a homolog to BAP1. In addition to having a substantially similar biological function, a homolog of BAP1 will also typically share substantial sequence similarity with the nucleic acid sequence of BAP1. For example, suitable homologs preferably share at least 30% sequence homology, more preferably, 50%, and even more preferably, are greater than about 75% homologous in sequence. In determining whether a sequence is homologous to BAP1, sequence similarity may be determined by conventional algorithms, which typically allow introduction of a small number of gaps in order to achieve the best fit. In particular, "percent homology" of two polypeptides or two nucleic acid sequences may be determined using the algorithm of Karlin and Altschul [(Proc. Natl. Acad. Sci. USA 87, 2264 (1993)]. Such an algorithm is incorporated into the NBLAST and XBLAST programs of Altschul, et al. (J. Mol. Biol. 215, 403 (1990)). BLAST nucleotide searches may be performed with the NBLAST program to obtain nucleotide sequences homologous to a nucleic acid molecule of the invention. Equally, BLAST protein searches may be performed with the XBLAST program to obtain amino acid sequences that are homologous to a polypeptide of the invention. To obtain gapped alignments for comparison purposes, Gapped BLAST is utilized as described in Altschul, et al. (Nucleic Acids Res. 25, 3389 (1997)). When utilizing BLAST and Gapped BLAST programs, the default parameters of the respective programs (e.g., XBLAST and NBLAST) are employed. See www.ncbi.nlm.nih.gov for more details. In an exemplary embodiment, the subject is human. In certain embodiments, the subject may have a carcinoma, sarcoma, or melanoma. In other embodiments, the subject may be suspected of having a carcinoma, sarcoma, or melanoma.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that may changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various iterations of the invention.

Example 1

BAP1 Mutations and Uveal Melanoma Metastasis

Uveal melanoma (UM) is the most common primary cancer of the eye and has a strong propensity for fatal metastasis (1). UMs are divided into class 1 (low metastatic risk) and class 2 (high metastatic risk) based on a validated multi-gene clinical prognostic assay included in the TNM classification system (2, 3). However, the genetic basis of metastasis remains unclear. Oncogenic mutations in the $G\alpha_q$ stimulatory subunit GNAQ are common in UM (4), but these mutations occur early in tumorigenesis and are not correlated with molecular class or metastasis (5, 6). On the other hand, class 2 tumors are strongly associated with monosomy 3 (7), suggesting that loss of one copy of chromosome 3 may unmask a mutant gene on the remaining copy which promotes metastasis.

Using exome capture followed by massively parallel sequencing (8, 9), we analyzed two class 2 tumors that were monosomic for chromosome 3 (MM56 and MM70) and matching normal DNA from peripheral blood lymphocytes. Both tumors contained inactivating mutations in BAP1, located at chromosome 3p21.1 (FIG. 1A). MM56 contained a C/G to T/A transition that created a premature termination codon (p.W196X). MM70 contained a deletion of 11 bp in exon 11, leading to a frameshift and premature termination of the BAP1 protein (p.Q322fsX100). The matched normal DNA samples did not contain these mutations, indicating that they were likely to be somatic in origin. No gene on chromosome 3 other than BAP1 contained deleterious somatic mutations that were present in both tumors (Table 1).

for HCFC1, which interacts with histone-modifying complexes during cell division (11, 13, 14). BAP1 also interacts with ASXL1 to form the Polycomb group repressive deubiquitinase complex (PR-DUB), which is involved in stem cell pluripotency and other developmental processes (15, 16). BAP1 exhibits tumor suppressor activity in cancer cells (10, 12), and BAP1 mutations have been reported in a small number of breast and lung cancer samples (10, 17).

Figure 1B:
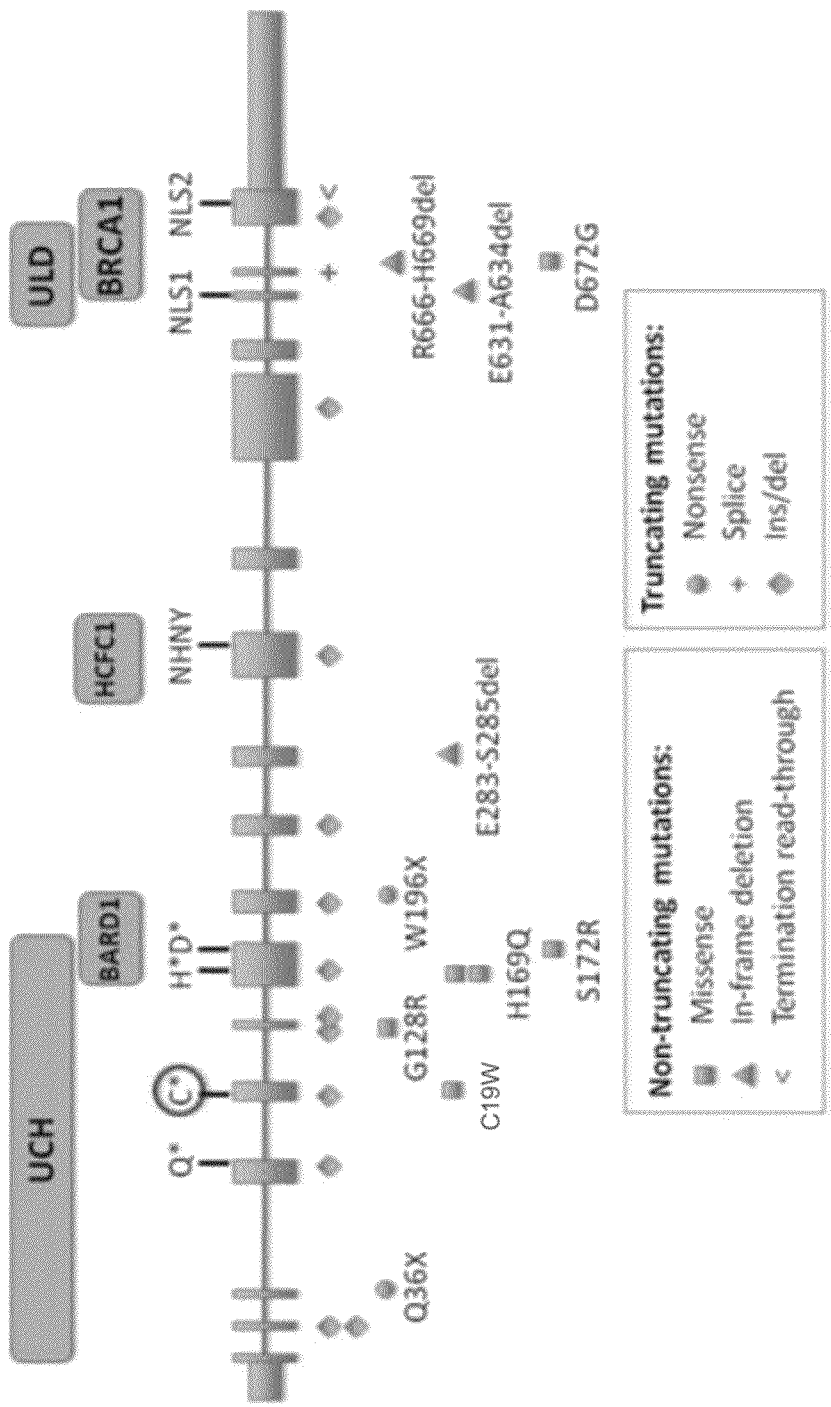
Figure 1C:
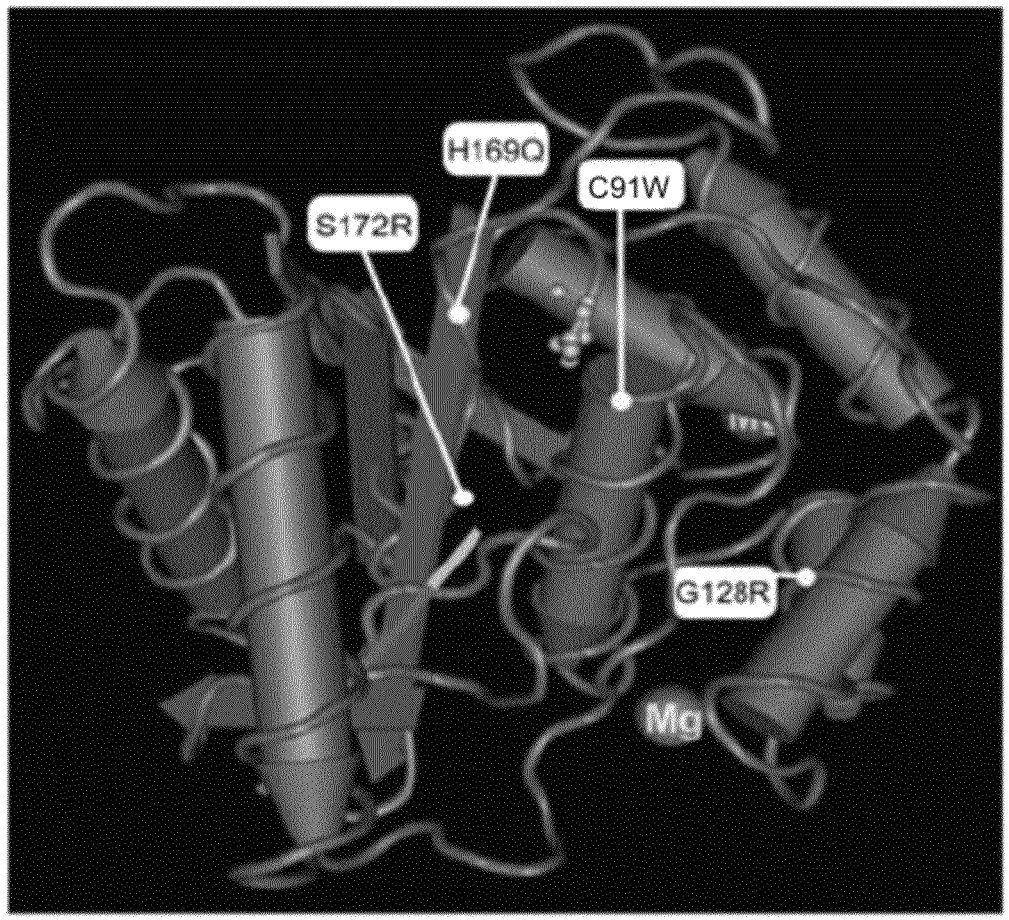

To further investigate BAP1, genomic DNA from 29 additional class 2 UMs, and 26 class 1 UMs were subjected to Sanger re-sequencing of all BAP1 exons. Altogether, BAP1 mutations were identified in 26 of 31 (84%) class 2 tumors, including 13 out-of-frame deletions and two nonsense mutation leading to premature protein termination, six missense mutations, four in-frame deletions, and one mutation predicted to produce an abnormally extended BAP1 polypeptide (FIG. 1A-C). Three of the missense mutations affected catalytic residues of the UCH active site (C91 and H169), two occurred elsewhere in the UCH domain, and one affected the ULD (FIG. 1B-C). All BAP1 missense mutations and in-

TABLE 1

Summary of DNA sequence alterations identified by exome capture and massively parallel sequencing of tumor DNA and matching normal peripheral blood lymphocyte DNA from uveal melanomas MM056 and MM070

| Chr 3 location (hg19) | Tumor | Indel End (hg19) | Gene | Reference Codon | Ref. Amino Acid | New Codon | New Amino Acid | Ref base (hg19) | Consensus | Read Depth | Present on Sanger sequence validation2 |
|---|---|---|---|---|---|---|---|---|---|---|---|
| 20,216,514 | MM56 | | SGOL1 | GGA | G | GTA | V | C | M | 16 | No |
| 43,641,970 | MM70 | | AN010 | CTA | L | CTG | L | T | Y | 77 | Not done |
| 44,488,382 | MM56 | | ZNF445 | AGC | S | AGA | R | G | K | 14 | Not done |
| 44,636,130 | MM70 | | ZNF660 | CTT | L | ATT | I | C | M | 9 | No |
| 45,715,863 | MM56 | | LIMD1 | TCC | S | TAC | Y | C | M | 53 | No |
| 46,008,495 | MM70 | | FYCO1 | CAG | Q | CAT | H | C | M | 19 | Not done |
| 48,457,135 | MM56 | | PLXNB1 | TGT | C | TGC | C | A | R | 11 | Not done |
| 48,630,022 | MM56 | | COL7A1 | GTG | V | GTT | V | C | M | 9 | Not done |
| 49,690,418 | MM56 | | BSN | CCT | P | CCA | P | T | W | 11 | No |
| 49,699,662 | MM56 | | BSN | TGG | W | GGG | G | T | K | 21 | No |
| 52,439,264 | MM70* | 52,439,274 | BAP1 | deletion | | | | CCCCATCCCAC (SEQ ID NO: 5) | deleted | 19 | Yes |
| 52,439,264 | MM70* | | BAP1 | CAC | H | CAG | Q | G | Q | 15 | Yes |
| 52,439,266 | MM70* | | BAP1 | CAC | H | AAC | N | G | N | 13 | Yes |
| 52,440,916 | MM56 | | BAP1 | TGG | W | TGA | X | C | X | 27 | Yes |
| 52,814,305 | MM56 | | ITIH1 | GAG | E | GAT | D | G | K | 15 | No |
| 56,650,054 | MM70 | | CCDC66 | TCT | S | CCT | P | T | Y | 13 | No |
| 123,695,755 | MM70 | | ROPN1 | CGG | R | TGG | W | G | R | 39 | Yes (germline) |
| 135,825,122 | MM70 | | PPP2R3A | ACG | T | ATG | M | C | Y | 33 | Yes (somatic) |
| 172,351,305 | MM56 | | NCEH1 | ACT | T | AAT | N | G | K | 20 | No |
| 180,327,975 | MM70 | | TTC14 | GGA | G | GAA | E | G | K | 22 | No |
| 183,041,104 | MM56 | | MCF2L2 | GGC | G | GGA | G | G | K | 25 | Not done |
| 194,062,926 | MM70 | | CPN2 | ACC | T | AAC | N | G | K | 24 | No |
| 194,408,437 | MM56 | | FAM43A | GAG | E | GAT | D | G | K | 9 | No |
| 195,306,227 | MM70 | | APOD | AAT | N | GAT | D | T | Y | 21 | Not done |

[1]In the case of Insertion/Deletions (InDels) that were detected with Novoalign, column 1 defines the start and column 3 defines the end. The BAP1 mutations reported in the current manuscript are asterisked and were incorrectly detected as base substitutions in the case of the InDel in MM70, in addition to being correctly detected as an InDel with Novoalign. This is why several substitutions are reported in MM70 for this gene, although they correspond to a single mutational event. We detected 20 additional putative somatic mutations in genes on chromosome 3. The predicted codon and amino acid changes for the appropriate strand are indicated where applicable, along with the base in the hg19 reference sequence and the base change reported as a consensus using IUPAC nomenclature. Reference bases and reference base changes are reported for the plus strand. Depth refers to the read depth of the altered base in the tumor sample. Sanger resequencing was performed to validate each variant detected in the tumor but not the germline.
[2]In the case of one mutation residing in ROPN1 the mutation was confirmed in the tumor and was also seen in the blood. This had been missed with exome capture. In the case of one mutation residing in PPP2R3A in tumor MM070 the mutation was confirmed to be a somatic alteration.

Figure 1D:
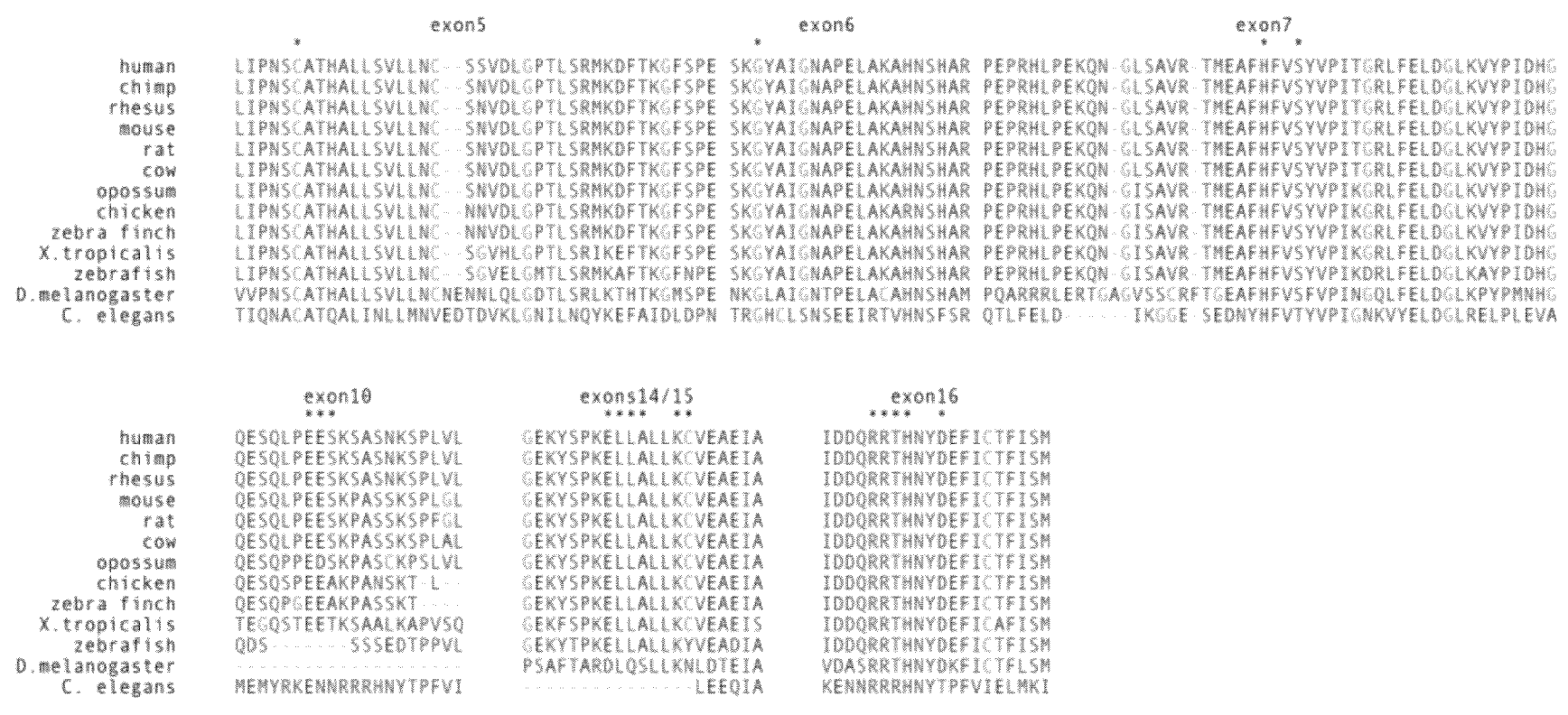

BAP1 encodes a nuclear ubiquitin carboxy-terminal hydrolase (UCH), one of several classes of deubiquitinating enzymes (10). In addition to the UCH catalytic domain, BAP1 contains a UCH37-like domain (ULD) (11), binding domains for BRCA1 and BARD1, which form a tumor suppressor heterodimeric complex (12), and a binding domain frame deletions affected phylogenetically conserved amino acids (FIG. 1D). Only one of 26 class 1 tumors contained a BAP1 mutation (NB101). This case may represent a transition state in which the tumor has sustained a BAP1 mutation but has not yet converted to class 2, suggesting that BAP1 mutations may precede the emergence of the class 2 signature. Somatic BAP1 mutations were also detected in two of three metastatic tumors. The summary of genetic data on uveal melanoma tumor samples are presented in Tables 2 and 3.

TABLE 2

Summary genetic data on uveal melanoma tumor samples in the study

| Tumor Number | Source of tumor analyzed | Gene expression class | Loss of Chr 3 | BAP1 mutation In normal DNA | BAP1 Mutation In tumor | Mutation in cDNA of gDNA (hg19) | BAP1 Exon With mutation | Protein change | Predicted effect on protein |
|---|---|---|---|---|---|---|---|---|---|
| MM 010 | Primary | Class 1 | No | No | No | | | | |
| MM 016 | Primary | Class 1 | No | No | No | | | | |
| MM 018 | Primary | Class 1 | No | No | No | | | | |
| MM 050 | Primary | Class 1 | No | No | No | | | | |
| MM 074 | Primary | Class 1 | No | No | No | | | | |
| MM 086 | Primary | Class 1 | No | No | No | | | | |
| MM 089 | Primary | Class 1 | No | No | No | | | | |
| MM 092 | Primary | Class 1 | No | No | No | | | | |
| MM 101 | Primary | Class 1 | No | No | No | | | | |
| MM 109 | Primary | Class 1 | No | No | No | | | | |
| MM 113 | Primary | Class 1 | No | No | No | | | | |
| MM 122 | Primary | Class 1 | Yes | No | No | | | | |
| NB 092 | Primary | Class 1 | Yes | No | No | | | | |
| NB 096 | Primary | Class 1 | No | No | No | | | | |
| NB 099 | Primary | Class 1 | No | No | No | | | | |
| NB 101 | Primary | Class 1 | No | No | Yes | g chr3.52,441,485-52,441,436delTCCCCGTAGAGCAAAGGATATGCGATTGGCAATGCCCCGGAGTTGGCAA (SEQ ID NO: 4) | 6 | Unknown | Loss of splice acceptor of exon 6 and potential cryptic splice leading to out of frame peptide and premature termination |
| NB 102 | Primary | Class 1 | No | No | No | | | | |
| NB 104 | Primary | Class 1 | Yes | No | No | | | | |
| NB 107 | Primary | Class 1 | No | No | No | | | | |
| NB 108 | Primary | Class 1 | No | No | No | | | | |
| NB 109 | Primary | Class 1 | No | No | No | | | | |
| NB 112 | Primary | Class 1 | No | No | No | | | | |
| NB 113 | Primary | Class 1 | No | No | No | | | | |
| NB 116 | Primary | Class 1 | Yes | No | No | | | | |
| NB 119 | Primary | Class 1 | No | No | No | | | | |
| NB 126 | Primary | Class 1 | No | No | No | | | | |
| MM 046 | Primary | Class 2 | Yes | No | Yes | C 2026-2028delGTG | 15 | P K637_C638delinsN | Deletion of K637 and C638 and substitution of N |

TABLE 2-continued

Summary genetic data on uveal melanoma tumor samples in the study

| Tumor Number | Source of tumor analyzed | Gene expression class | Loss of Chr 3 | BAP1 mutation In normal DNA | BAP1 Mutation In tumor | Mutation in cDNA of gDNA (hg19) | BAP1 Exon With mutation | Protein change | Predicted effect on protein |
|---|---|---|---|---|---|---|---|---|---|
| MM 054 | Primary | Class 2 | Yes | No | Yes | G chr3 52,441,434-52,441,483del | 6 | Unknown | Loss of splice acceptor of exon 6 and potential cryptic splice leading to out of frame peptide and premature termination |
| MM 055 | Primary | Class 2 | Yes | No | Yes | c 622C > G | 7 | pH169Q | UCH active site mutated |
| MM 056 | Primary | Class 2 | Yes | No | Yes | c 703G > A | 8 | pW196X | Premature termination |
| MM 060 | Primary | Class 2 | Yes | No | Yes | c 872C > T | 9 | pQ253X | Premature termination |
| MM 066 | Primary | Class 2 | Yes | No | Yes | c 960-968delCTGAGGAGT | 10 | P. E283-S285del | In-frame deletion between BARD1 and HCFC1 binding domains |
| MM 070 | Primary | Class 2 | Yes | No | Yes | c 1083-1093delCCCCatCCCAC (SEQ ID NO: 5) | 11 | P Q322fsx100 | Premature termination |
| MM 071 | Primary | Class 2 | Yes | No | Yes | c 2130A > G | 16 | Pd72G | AA change in ULD domain |
| MM 080 | Primary | Class 2 | Yes | No | No | | | | |
| MM 081 | Primary | Class 2 | Yes | No | Yes | g chr3.52441197-52441174delTGACCATGGTAGGCACCATGAGC (SEQ ID NO: 6) | 7 | unknown | Loss of splice acceptor of exon 7 and potential cryptic splice leading to out of frame peptide and premature termination |
| MM 083 | Primary | Class 2 | Yes | No | Yes | c 736-751delCGGGTCATCATGGAG (SEQ ID NO: 7) | 8 | pR207fsX32 | Premature termination |
| MM 087 | Primary | Class 2 | Yes | Yes | Yes | c 1318-1319insA | 12 | pE402fsX2 | Premature termination |
| MM 090 | Primary | Class 2 | Yes | No | Yes | c 468-487delinsA | 5 | p.F118X | Premature termination |
| MM 091 | Primary | Class 2 | Yes | No | Yes | c 874delG | 9 | pQ253fs | Premature termination |
| MM 100 | Primary | Class 2 | Yes | No | Yes | g chr3 52,443,784-42,443,750del | 2 | Unknown | Los of splice |

TABLE 2-continued

Summary genetic data on uveal melanoma tumor samples in the study

| Tumor Number | Source of tumor analyzed | Gene expression class | Loss of Chr 3 | BAP1 mutation In normal DNA | BAP1 Mutation In tumor | Mutation in cDNA of gDNA (hg19) | BAP1 Exon With mutation | Protein change | Predicted effect on protein |
|---|---|---|---|---|---|---|---|---|---|
| | | | | | | CCCCTCCTCTTGTCGC CCCACCCAGGCCTCTT CAC (SEQ ID NO: 8) | | | acceptor of exon 2 and potential cryptic splice leading to out of frame peptide and premature termination |
| MM 103 | Primary | Class 2 | Yes | No | Yes | c 2303T > A | 17 | pTer729R | Read through termintion codon |
| MM 110 | Primary | Class 2 | Yes | NO | Yes | c 1829-1833delCCCCT | 13 | ps571fsX25 | Premature termination |
| MM 120 | Primary | Class 2 | Yes | No | Yes | C 259delC | 4 | pF48fsX22 | Premature termination |
| MM 121 | Primary | Class 2 | Yes | No | Yes | c 497G > C | 6 | pG128R | Missense |
| MM 125 | Primary | Class 2 | Yes | No | Yes | c 622C > G | 7 | pH169Q* | UCH active site mutated |
| MM 127 | Primary | Class 2 | No | No | No | | | | |
| MM128 | Primary | Class 2 | Yes | No | Yes | c 2112-2120del 9 GAAGGACCC | 16 | R666-H669delins N | RRTH deletion in ULD domain |
| MM 133 | Primary | Class 2 | No | No | No | | | | |
| MM 134 | Primary | Class 2 | No | No | No | | | | |
| MM 135 | Primary | Class 2 | Yes | No | Yes | c 388T > G | 5 | p.C91W | UCH active site mutated (active site) |
| NB 185 | Primary | Class 2 | No | No | Yes | c 2006-2017 delGAGCTGCTGGCA (SEQ ID NO: 9) | 15 | p E631-A634del | Internal in-frame deletion in ULD domain |
| NB 191 | Primary | Class 2 | No | No | Yes | C 610-634 delGGAGGCGTTCCACT TTGTCAGCTAT (SEQ ID NO: 10) | 7 | P M166fsX12 | Premature termination |
| NB 195 | Primary | Class 2 | No | No | Yes | g chr3 52,443,771-52,443,734 delCGCCCCACCCAGGC CTCTTCACCCTGCTCG TGGAAGAT (SEQ ID NO: 11) | 2 | Unknown | Loss of splice acceptor of exon 2 and potential cryptic splice leading to out of frame peptide and premature termination |
| NB 199 | Primary | Class 2 | No | No | Yes | chr3: 52,436,691G > T Splice acceptor AG to AT | 16 | Unknown | Unknown, likely premature termination |
| NB 200 | Primary | Class 2 | No | No | Yes | c 631C > G | 7 | p S172R | Missense |
| NB 214 | Primary | Class 2 | No | No | No | | | | |

TABLE 2-continued

Summary genetic data on uveal melanoma tumor samples in the study

| Tumor Number | Source of tumor analyzed | Gene expression class | Loss of Chr 3 | BAP1 mutation In normal DNA | BAP1 Mutation In tumor | Mutation in cDNA of gDNA (hg19) | BAP1 Exon With mutation | Protein change | Predicted effect on protein |
|---|---|---|---|---|---|---|---|---|---|
| MM 152M | Metastasis | NO | NO | No | Yes | C 2195-2220 delCAGAACCATCTCCG TGCGGCGGCGCCA (SEQ ID NO: 12) | 17 | p E693fsX13 | Premature termination |
| NB 071M | Metastasis | Class 2 | Yes | No | Yes | c 221C > T | 3 | Q36* | Premature termination |
| PV L8 | Metastasis | No | No | No | No | | | | |

TABLE 3

| Tumor Number | Source of tumor analyzed | GEP class | LOH3 | BAP1 mutation normal DNA | BAP1 mutation tumor | Mutation in gDNA (hg19) | BAP1 cDNA | Mutant exon | Predicted Protein change | Predicted effect on protein |
|---|---|---|---|---|---|---|---|---|---|---|
| MM 133 | Primary/ fresh frozen | 2 | ? | NA | No | NA | | NA | NA | |
| MM 134 | Primary/ fresh frozen | 2 | ? | NA | No | NA | | NA | NA | |
| MM 137 | Primary/ fresh frozen | 2 | ? | No | Yes | g.chr3: 52443889-52443927delATTC ATCTTCCCGCGG GGCGGCCCCTC AGCGCCATGTCC (SEQ ID NO: 13) | c.82-121del | 1 | premature truncation | deletes first two aa (MN) and 33 bp from 5'UTR (ATTCATCTTCCCGCG GGGCGGCCCCTCAG CGCCATGTCC) (SEQ ID NO: 13) |
| MM 138 | Primary/ fresh frozen | 2 | ? | NA | No | NA | | NA | NA | |
| MM 144 | Primary/ fresh frozen | 2 | ? | No | Yes | c.265delC; g.chr3: 52442595delC | c.265delC | 4 | premature truncation (p.F50LfsX 22) | |
| MM 150 | Primary/ fresh frozen | 2 | ? | NA | No | NA | | NA | NA | |
| MM 151A | Primary/ fresh frozen | 2 | ? | No | Yes | g.chr3: 52440925-52440918delAGG GCCCT | | 8 | Deletion of exon 6 | delete AG splice donor of exon 8 and then deletion of 6 bp in exon 6- leaves 48 bp. Might be exon skipping. |
| Mouse 204 (MM151 A met) | | | ? | NA | Yes | g.chr3: 52440925-52440918delAGG GCCCT | | 8 | Deletion of exon 6 | |
| MM 161 | Primary/ fresh frozen | 2 | ? | ? | Yes | c.1013-1014delAG; g.chr3: 52439814-52439813delAG | | 10 | premature truncation | Premature termination |
| MM 162 | Primary/ fresh frozen | 2 | ? | ? | Yes | g.chr3: 52437431 G / C and chr3: 52437433del A | | 13 | premature truncation | Splice mutation, deletion of A |

TABLE 3-continued

| Tumor Number | Source of tumor analyzed | GEP class | LOH3 | BAP1 mutation normal DNA | BAP1 mutation tumor | Mutation in gDNA (hg19) | BAP1 cDNA | Mutant exon | Predicted Protein change | Predicted effect on protein |
|---|---|---|---|---|---|---|---|---|---|---|
| OP-11-953 (Emory) | Primary/ paraffin embedded | ? | ? | | Yes | g.chr3: 52442086-52442106delGGTA TCAGCTGTGAAA CCAAG (SEQ ID NO: 14) | | 10 | premature truncation | |
| MM 131T | Primary/ fresh frozen | 1b | ? | NA | No | NA | | | | |
| MM 159T | Primary/ fresh frozen | 2 | ? | NA | No | NA | | NA | NA | |

NA: Not applicable

Figure 2:
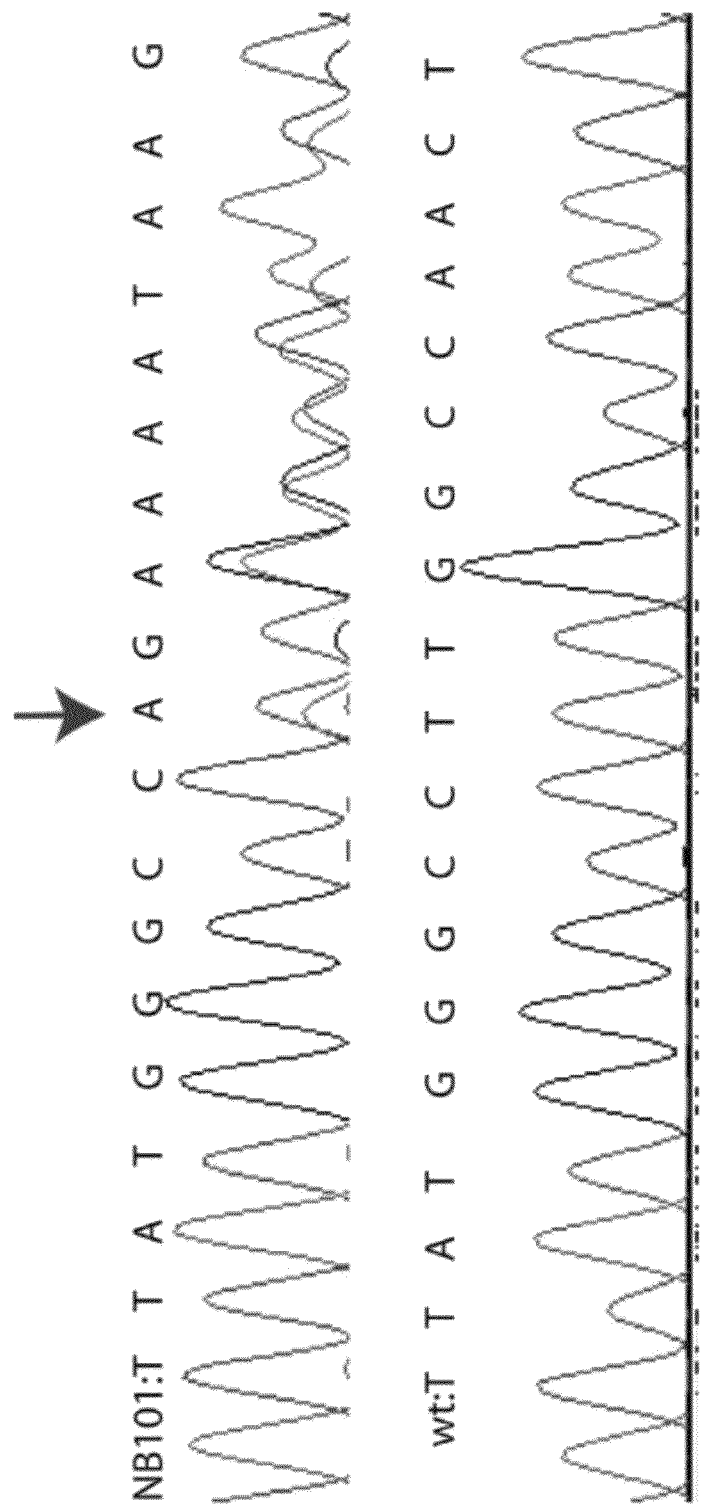
FIG. 2 depicts Sanger sequence trace of one end of the mutated region of NB101. The breakpoint at one end of the insertion/deletion is indicated with an arrow. Wild type sequence is indicated below the NB101 sequence. (SEQ ID NO:61-62)

One copy of chromosome 3 was missing in all 17 BAP1-mutant class 2 tumors for which cytogenetic data were available, consistent with chromosome 3 loss uncovering recessive BAP1 mutations. Normal DNA from 20 patients with BAP1-mutant class 2 primary tumors and the two with metastatic tumors was available and did not contain a BAP1 mutation, indicating that the mutations were somatic in origin. However, we detected one germline mutation (p.E402fsX2; c.1318-1319insA) in the patient with the class 1 tumor NB101 (Table 2), and this case was particularly interesting. Re-sequencing of this tumor revealed a deletion of a segment of exon 6 of BAP1, including its splice acceptor. This mutation is predicted to result in a premature truncation of the encoded protein (Table 2). However, the wildtype allele was present at levels similar to the mutant allele, indicating that it was disomic for chromosome 3 (FIG. 2). Hence, this case may represent a transition state in which the tumor is still class 1 but has sustained a BAP1 mutation. This might suggest that the BAP1 mutations precede loss of chromosome 3 and the emergence of the class 2 signature during tumor progression. Thus, germline alterations in BAP1 can predispose to UM.

Figure 18:
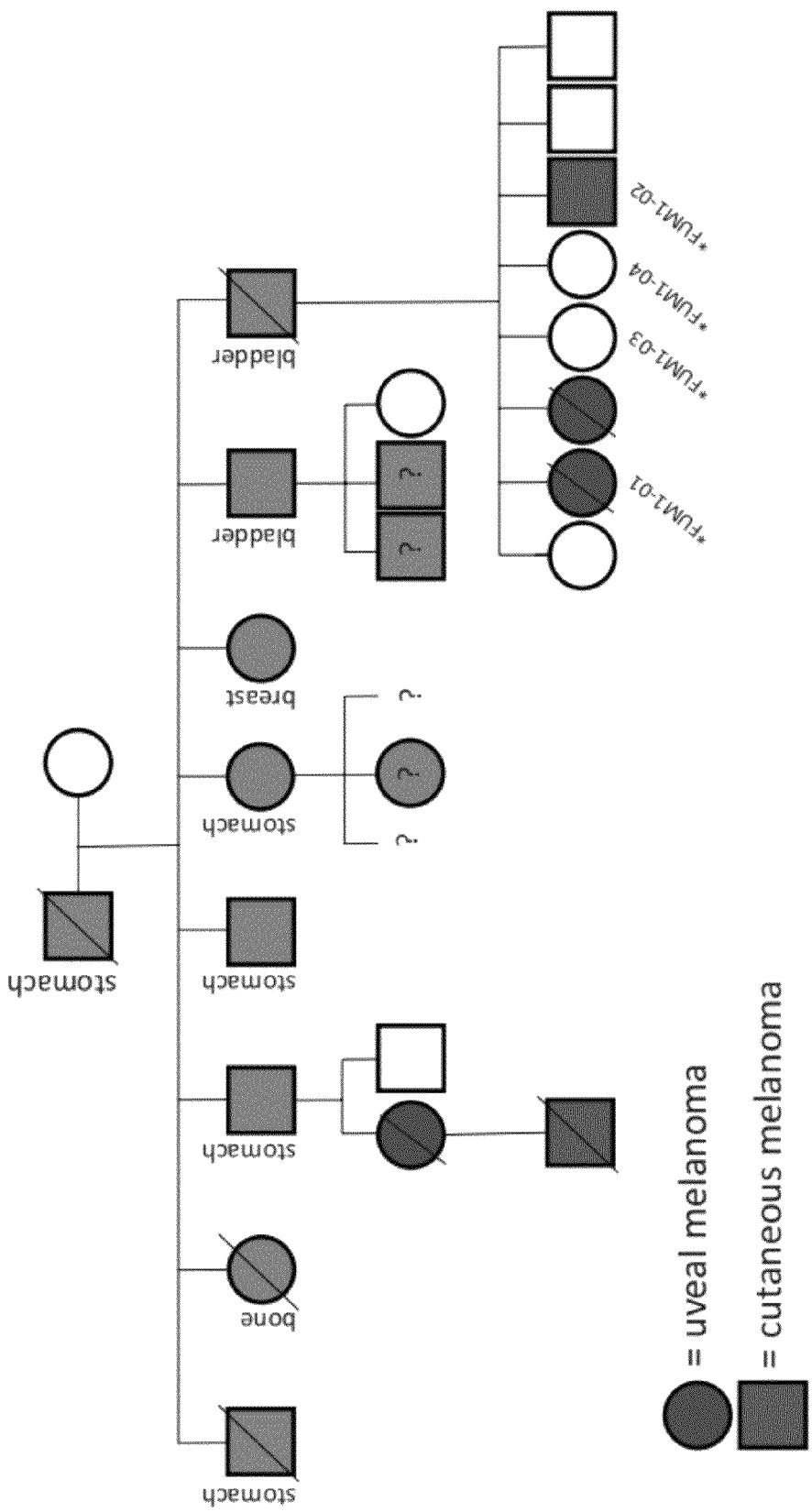
FIG. 18 depicts an illustration of a family with germline BAP1 mutations.

Other germline (blood) mutations in exon 13 (g.chr3: 52437465insT; pE566X; c.1695-1696insT leading to premature protein termination) in FUM1-01 and FUM-02 were also detected (see FIG. 18).

GNAQ mutation status was available in 15 cases. GNAQ mutations were present in 4/9 BAP1 mutant tumors and 3/6 BAP1 wildtype tumors, indicating that there was no correlation between GNAQ and BAP1 mutation status.

UM usually metastasizes to the liver, where it is difficult to obtain specimens for research. However, we were able to obtain sufficient DNA from three UM liver metastases for analysis. BAP1 mutations were detected in two of the three metastatic tumors, supporting the hypothesis that cells mutant for BAP1 are indeed the ones responsible for metastasis (Table 2). NB071M contained a nonsense mutation (Q36X), and MM152M contained an out-of-frame deletion (p.E693fsX13). Both mutations are predicted to cause premature protein truncation. Primary tumor DNA on either case was unavailable.

Figure 3:
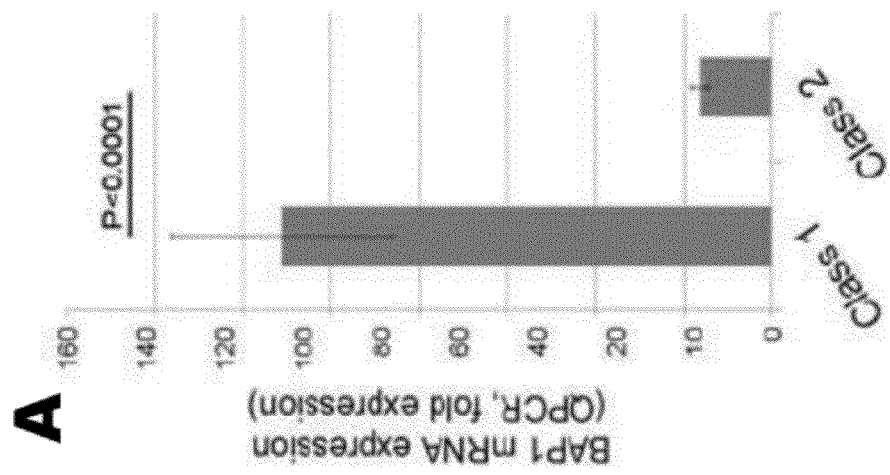
FIG. 3 depicts bar graphs of BAP1 mRNA levels. (A) BAP1 mRNA levels measured by quantitative RT-PCR in 9 non-metastasizing class 1 UMs and 28 metastasizing class 2 UMs. (B) Relationship between BAP1 mRNA levels (measured by quantitative RT-PCR) and type of BAP1 mutation in 9 UMs with nonsense mutations, 10 UMs with missense mutations (including small in-frame deletions, splice acceptor, and stop codon read-through mutations), and 4 class 2 UMs in which no BAP1 mutations were detected.
Figure 3:
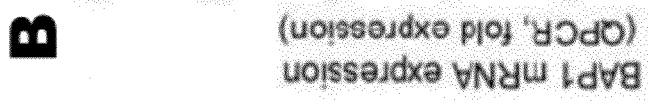

Quantitative RT-PCR showed that BAP1 mRNA levels were significantly lower in class 2 tumors compared to class 1 tumors ($P<0.0001$) (FIG. 3A). Truncating mutations were associated with significantly lower mRNA levels than missense mutations ($P=0.001$) (FIG. 3B), consistent with nonsense mediated mRNA decay in the former group. Class 2 tumors in which BAP1 mutations were not identified expressed very low levels of BAP1 mRNA (FIG. 3B).

To determine whether the low BAP1 mRNA levels in class 2 tumors without detectable BAP1 mutations may be explained by DNA methylation, we performed a preliminary analysis of DNA methylation of BAP1. This did not reveal a convincing difference between class 1 and class 2 tumors. However, analysis of the BAP1 promoter was limited by an unusually complex CpG island that will require further work to resolve. Thus, we cannot rule out a role for methylation in class 2 tumors in which BAP1 mutations were not found. However, with almost 85% of class 2 tumors harboring mutations, we do not expect that methylation will be a major mechanism of BAP1 inactivation. An alternative explanation is that these tumors may contain very large deletions of the BAP1 locus or other mutations not detectable by our sequencing method.

Figure 4:
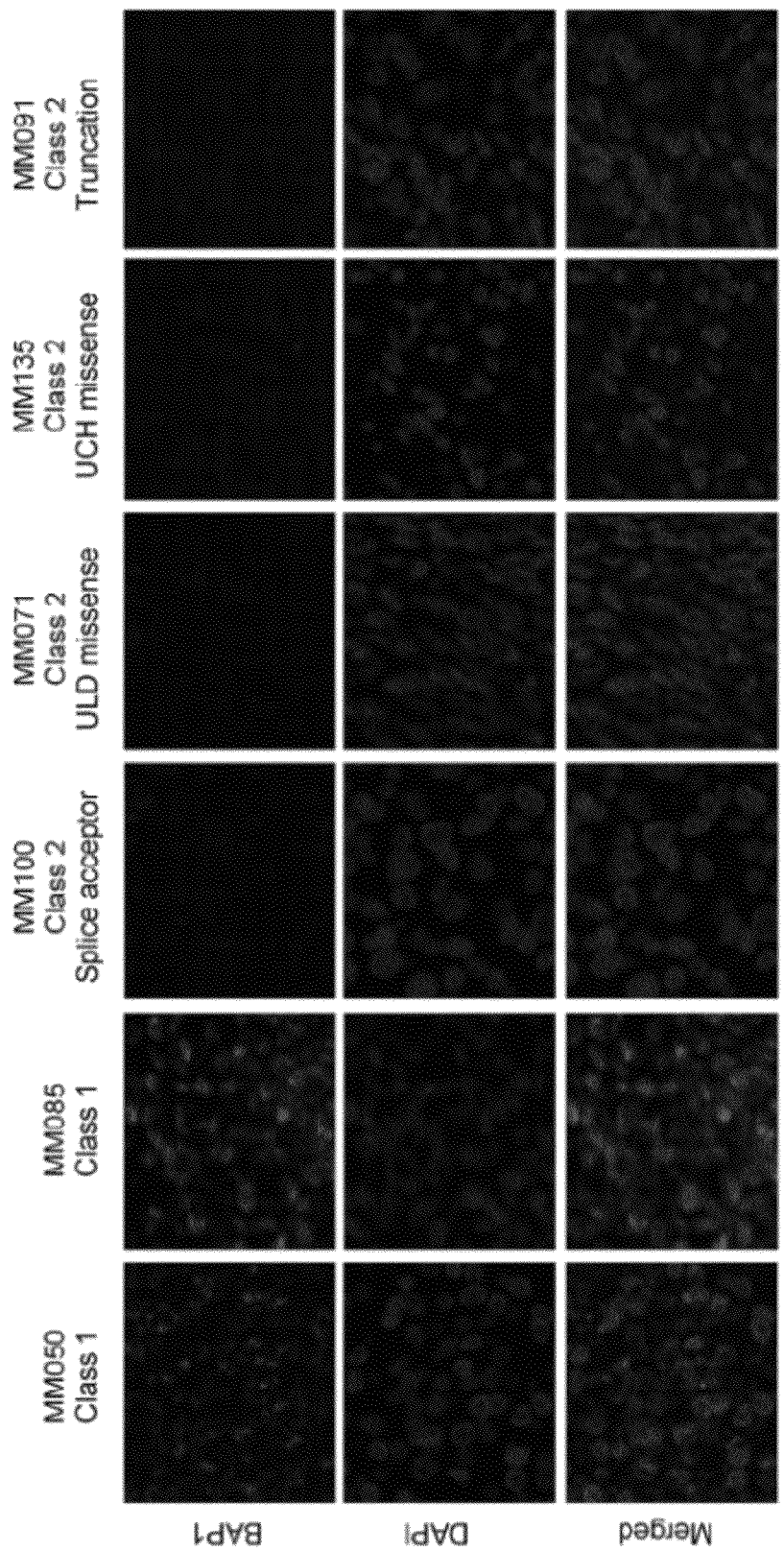
FIG. 4 depicts a series of photographs illustrating that BAP1 mutations disrupt BAP1 protein expression in human uveal melanoma samples. Immunofluorescence analysis of BAP1 protein expression was performed on archival tumor specimens from uveal melanomas of known class and BAP1 mutation status, as indicated. All images were captured at 40× and are represented at the same magnification. Scale bar, 10 microns. No BAP1 expression is seen in the Class 2 metastasizing UM cells (MM100, MM071, MM135, MM091) whereas expression is seen in the class 1 non-metastasizing UM cells (MM050, MM085).

Immunofluorescence revealed abundant nuclear BAP1 protein in two class 1 tumors but virtually none in four BAP1 mutant class 2 tumors (FIG. 4). This was expected for the two tumors with mutations expected to cause premature protein terminations (MM 091 and MM 100), but it was surprising for the two tumors with missense mutations (MM 071 and MM 135) and suggests that these mutations lead to protein instability.

Figure 5:
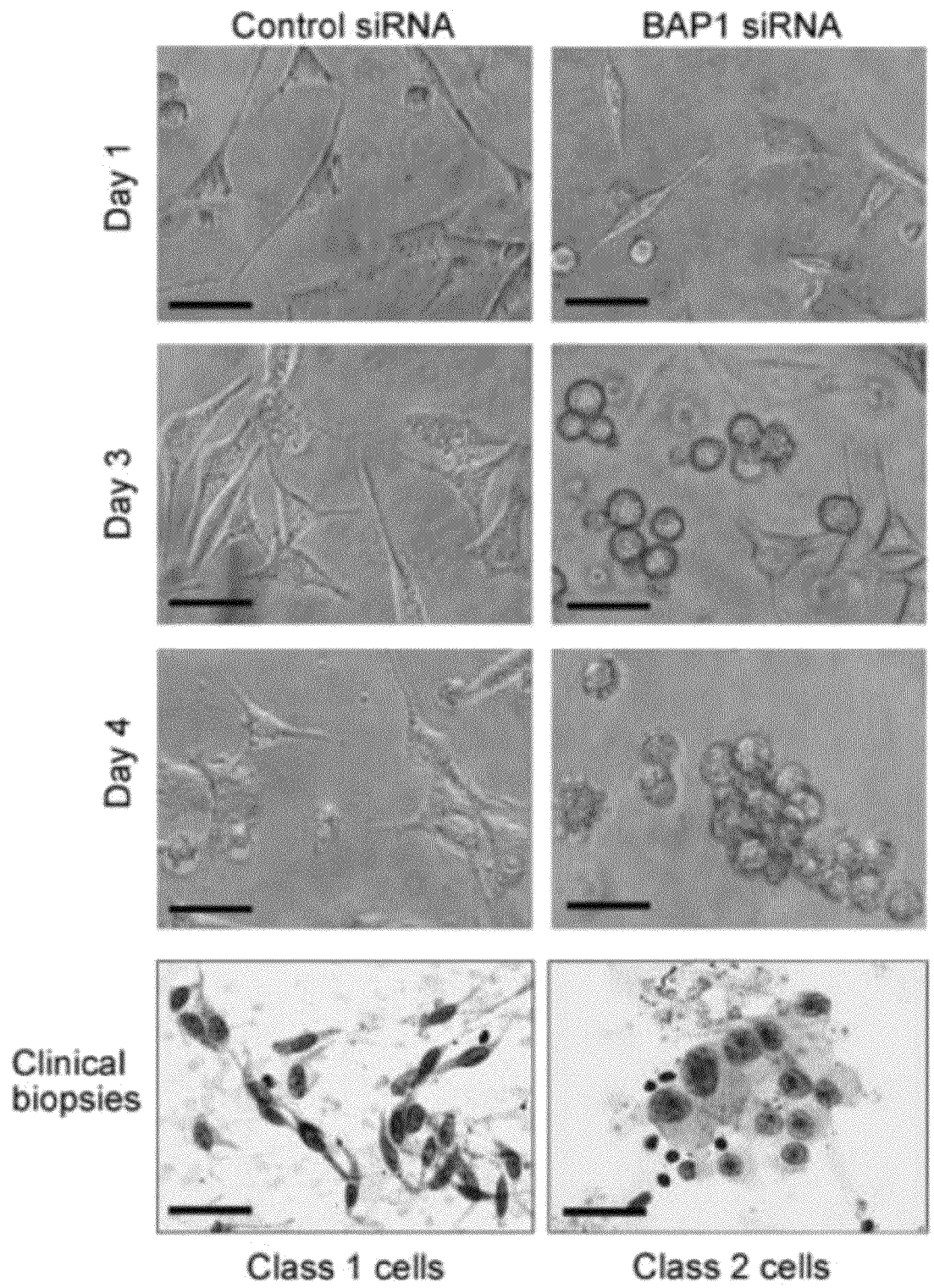
FIG. 5 depicts a series of micrographs illustrating that UM cells depleted of BAP1 acquire properties that are typical of metastasizing class 2 tumor cells. Phase contrast photomicrographs of 92.1 uveal melanoma cells transfected with BAP1 or control siRNA at the indicated days. Bottom panels show representative examples of class 1 and class 2 uveal melanoma cells obtained from patient biopsy samples (Papanicolaou stain). Scale bars, 10 microns.
Figure 6:
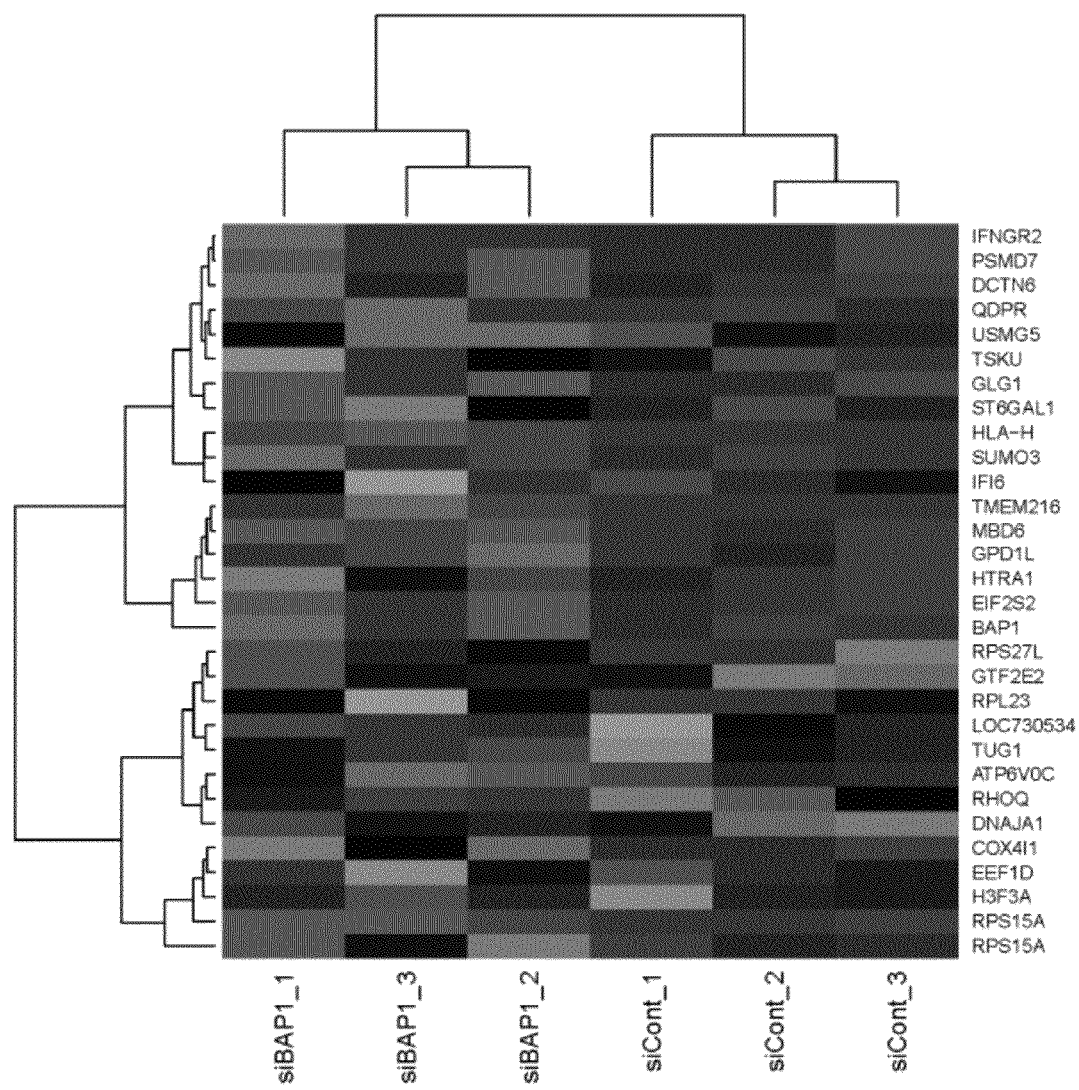
FIG. 6 depicts a gene expression heatmap of the top class 1 versus class 2 discriminating transcripts in 92.1 uveal melanoma cells transfected with control versus BAP1 siRNAs.
Figure 7A:
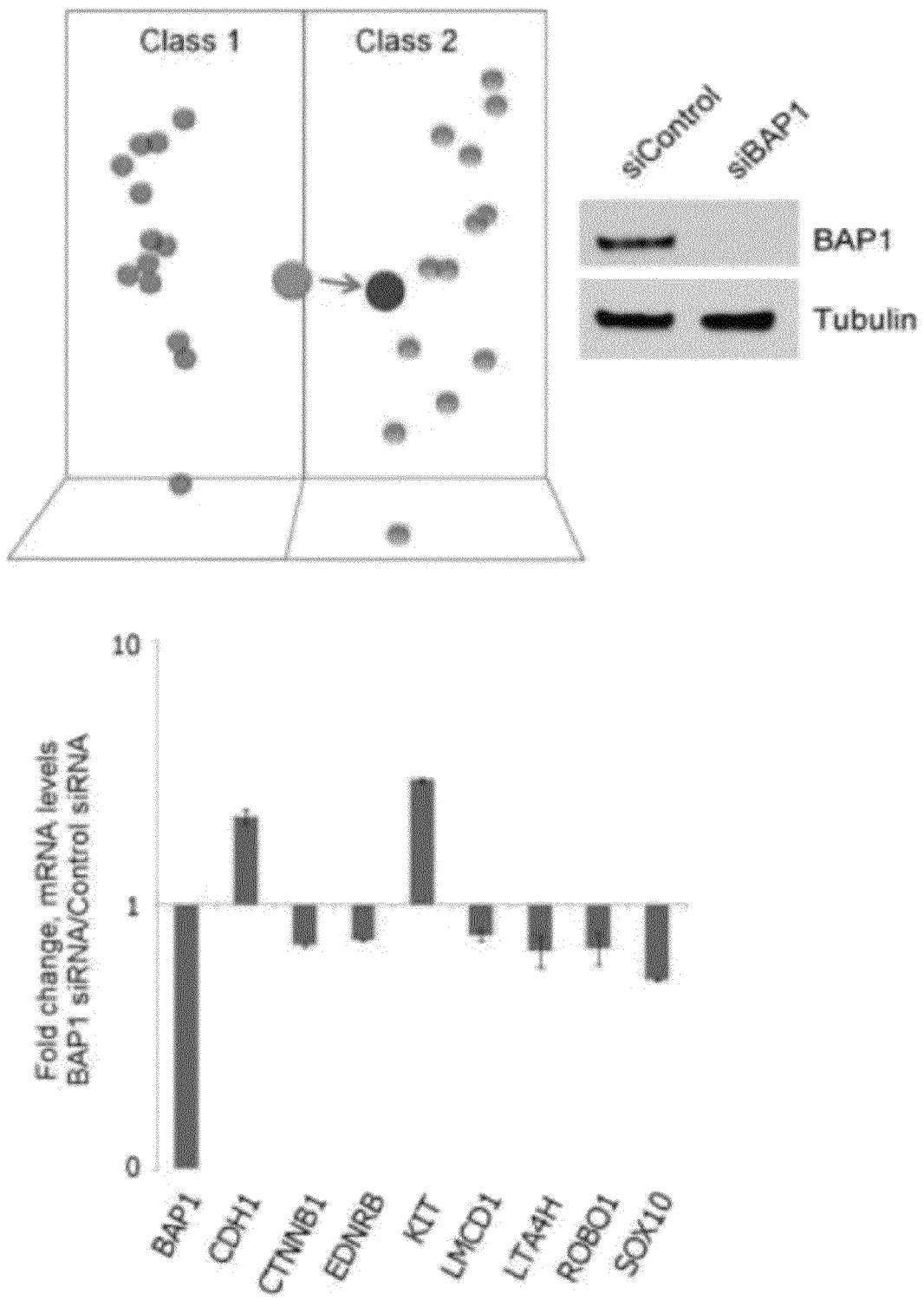
FIG. 7 depicts a diagram, a Western blot, and a bar graph showing the effects of BAP1 depletion by siRNA. 92.1 cells transfected with BAP1 siRNA and evaluated after five days. (A) BAP1 protein levels were efficiently depleted to less than 95% of control levels (see Western blot). Upper panel depicts principal component analysis to show effect of BAP1 knockdown on gene expression signature. The small spheres represent the training set of known class 1 (blue) and class 2 (red) tumors. Large spheres represent the control-transfected (gray) and BAP1 siRNA transfected (red) cells. Lower panel depicts mRNA levels measured by quantitative RT-PCR of a panel of melanocyte lineage genes, presented as fold change in BAP1 siRNA/control siRNA transfected cells. Results are representative of three independent experiments. (B) mRNA levels of mRNAs of a panel of melanocyte lineage genes measured by quantitative RT-PCR, presented as fold change in BAP1 siRNA/control siRNA transfected cells. (C) RNAi mediated depletion of BAP1 in 92.1 and Mel290 UM cell lines using two independent siRNAs that target BAP1. Duplicate experiments of each cell line and siRNA are shown.
Figure 7B:
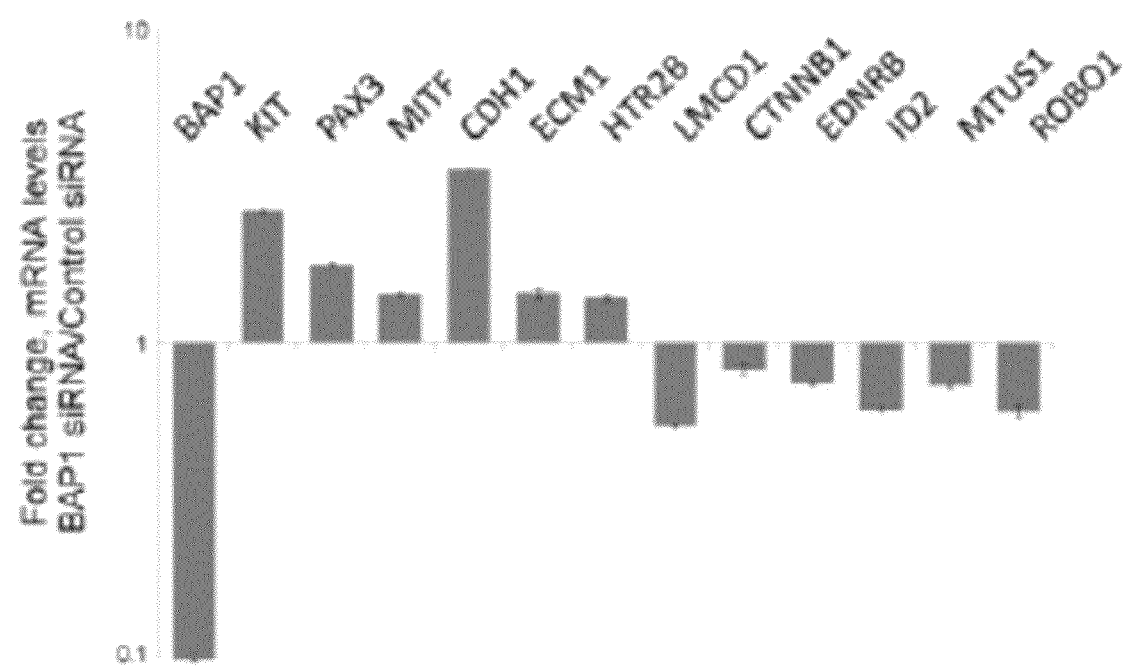
Figure 7C:
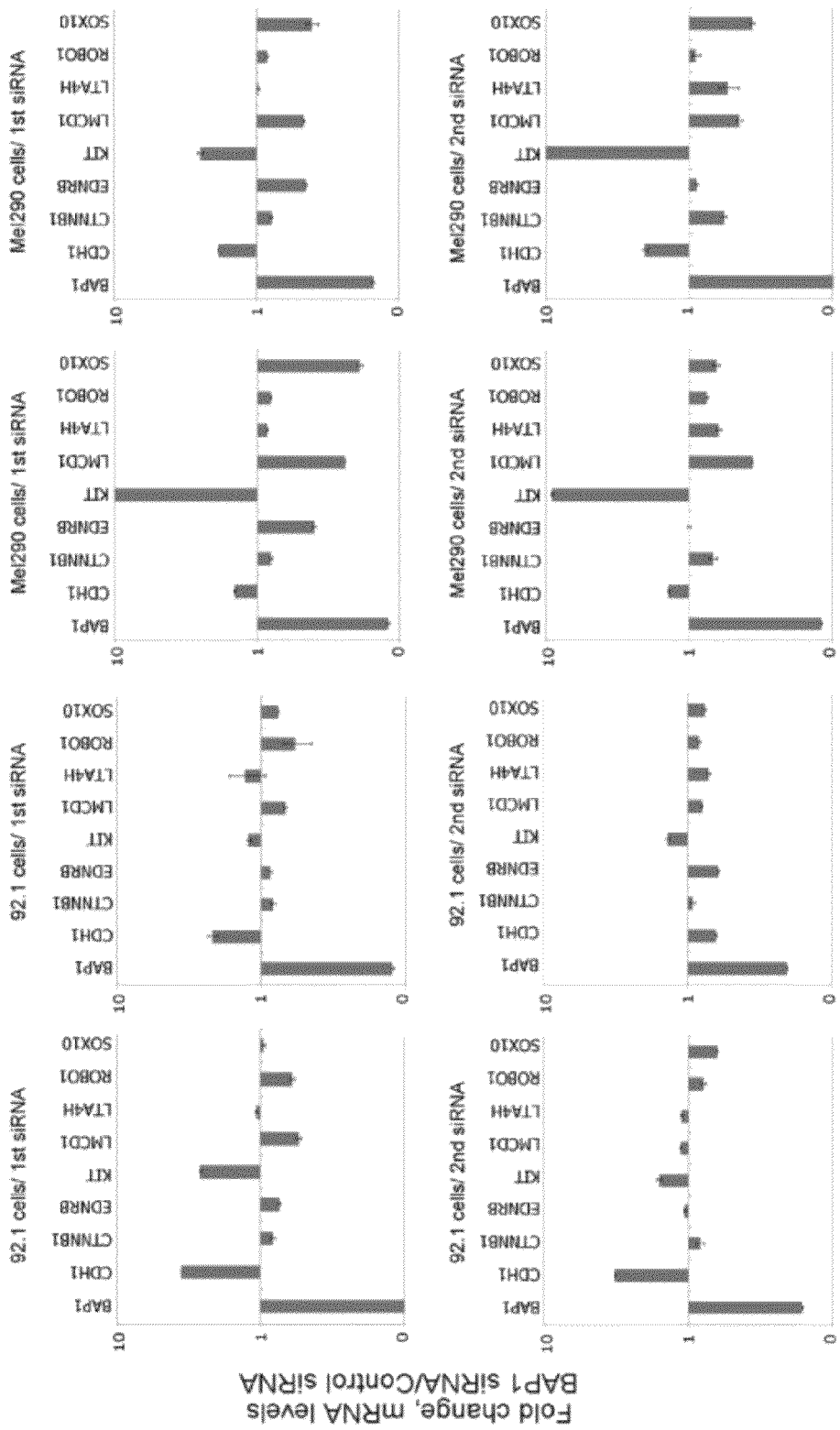

RNAi-mediated knock down of BAP1 in 92.1 UM cells, which did not harbor a detectable BAP1 mutation, recapitulated many characteristics of the de-differentiated class 2 UM phenotype (18). Cells transfected with control siRNA exhibited typical melanocytic morphology, including dendritic projections and cytoplasmic melanosomes (FIG. 5), whereas cells transfected with BAP1 siRNA lost these features, developed a rounded epithelioid morphology and grew as multicellular non-adherent spheroids, strikingly similar to the features of class 2 clinical biopsy samples (FIG. 5). Microarray gene expression profiling of 92.1 UM cells transfected with control versus BAP1 siRNA showed that most of the top genes that discriminate between class 1 and class 2 tumors shifted in the class 2 direction in BAP1 depleted cells compared to control cells (FIG. 6). Similarly, depletion of BAP1 shifted the gene expression profile of the multi-gene clinical prognostic assay towards the class 2 signature (FIG. 7A). BAP1 depletion caused a reduction in mRNA levels of neural crest migration genes (ROBO1), melanocyte differentiation genes (CTNNB1, EDNRB and SOX10) and other genes that are down-regulated in class 2 tumors (LMCD1 and LTA4H) (18). In contrast, BAP1 depletion caused an increase in mRNA levels of CDH1 and the proto-oncogene KIT, which are highly expressed in class 2 tumors (19). Similarly, mRNA transcripts of KIT, MITF and PAX3, whose protein products are associated with proliferation of pre-terminally differentiated melanocytes and have oncogenic effects when overactive in melanoma (20-22), were significantly up-regulated by BAP1 depletion (FIG. 7B). Similar results were seen in other UM cell lines and with an independent BAP1 siRNA (FIG. 7C).

GNAQ mutations occur early in UM and are not sufficient for malignant transformation (4), but they may create a dependency of the tumor cells on constitutive GNAQ activity. In contrast, BAP1 mutations occur later in UM progression and coincide with the onset of metastatic behavior. Thus, simultaneous targeting of both genetic alterations might have synergistic therapeutic effects. One potential strategy to counteract the effects of BAP1 mutation would be to inhibit the RING1 ubiquinating activity that normally opposes the deubiquinating activity BAP1 (16). Our findings strongly implicate mutational inactivation of BAP1 as a key event in the acquisition of metastatic competence in UM, and they dramatically expand the role of BAP1 and other deubiquitinating enzymes as potential therapeutic targets in cancer.

Materials and Methods for Example 1

Patient Materials

Acquisition of patient material (matched tumor and normal samples) has been described elsewhere (25) (Table 4). This study was approved by the Human Studies Committee at Washington University (St. Louis, Mo.), and informed consent was obtained from each subject. Tumor tissue was obtained immediately after eye removal, snap frozen, and prepared for RNA and DNA analysis. UM metastases were collected from liver biopsies at the time of metastatic diagnosis. All samples were histopathologically verified. Genomic DNA from tumors was prepared using the Wizard Genomic DNA Purification kit (Promega, Madison, Wis.). DNA from blood was isolated using the Quick Gene DNA whole blood kit S (Fugifilm, Tokyo, Japan). RNA was isolated using the PicoPure kit (including the optional DNase step). All RNA samples were converted to cDNA using the High Capacity cDNA Reverse Transcription kit from Applied Biosystems (Applied Biosystems Inc., Foster City, Calif.) following the manufacturer's protocol.

TABLE 4

Summary of clinical and pathologic data on uveal melanoma patients in the study

| Tumor Number | Source of tumor analyzed | Age at primary tumor diagnosis | Gender | Tumor diameter of primary tumor | Tumor thickness of primary tumor | Cillary body involvement | Pathologic cell type of primary tumor | Treatment of primary tumor | Mons follow-up | Metastasis |
|---|---|---|---|---|---|---|---|---|---|---|
| MM 010 | Primary | 41 | Male | 17 | 9.9 | No | Mixed | Enucleation | 131.2 | Yes |
| MM 016 | Primary | 24 | Female | 24 | 12.6 | Yes | Spindle | Enucleation | 87.8 | Yes |
| MM 018 | Primary | 55 | Male | 12 | 9.2 | No | Epithelioid | Enucleation | 67.4 | No |
| MM 050 | Primary | 50 | Female | 19 | 8.9 | Yes | Epithelioid | Enucleation | 71.4 | No |
| MM 074 | Primary | 77 | Male | N/A | 22.0 | N/A | Mixed | Enucleation | 24.4 | No |
| MM 086 | Primary | 47 | Male | 14 | 14.0 | No | Spindle | Enucleation | 17.7 | No |
| MM 089 | Primary | 74 | Male | 18 | 8.1 | Yes | Spindle | Enucleation | 8.1 | Yes |
| MM 092 | Primary | 61 | Male | 20 | 13.4 | Yes | Epithelioid | Enucleation | 8.0 | No |
| MM 101 | Primary | 66 | Female | 15 | 6.4 | No | Spindle | Enucleation | 10.8 | No |
| MM 109 | Primary | 56 | Male | 15 | 12.7 | Yes | Spindle | Enucleation | 8.8 | No |
| MM 113 | Primary | 54 | Male | 14 | 11.0 | No | Mixed | Enucleation | 8.0 | No |
| MM 122 | Primary | 52 | Male | N/A | N/A | Yes | Epithelioid | Enucleation | 1.0 | No |
| NB 092 | Primary | 53 | Male | 11 | 4.4 | No | Mixed | Brachytherapy | 25.2 | No |
| NB 096 | Primary | 55 | Female | 15 | 3.8 | No | Spindle | Brachylerapy | 24.1 | No |
| NB 099 | Primary | 76 | Male | N/A | N/A | No | Other | Biopsy | 1.0 | No |
| NB 101 | Primary | 57 | Female | 14 | 2.6 | Yes | Other | Brachytherapy | 23.2 | No |
| NB 102 | Primary | 83 | Female | 13 | 2.4 | No | Epithelioid | Brachytherapy | 27.5 | No |
| NB 104 | Primary | 62 | Male | 13 | 5.5 | No | Epithelioid | Brachytherapy | 24.1 | No |
| NB 107 | Primary | 58 | Male | 15 | 10.0 | Yes | Epithelioid | Brachytherapy | 19.9 | No |
| NB 108 | Primary | 66 | Female | 10 | 2.6 | No | Other | Brachytherapy | 17.8 | No |
| NB 109 | Primary | 76 | Male | 18 | 8.4 | Yes | Spindle | Brachytherapy | 9.1 | No |
| NB 112 | Primary | 53 | Male | 12 | 6.1 | No | Other | Brachytherapy | 21.4 | No |
| NB 113 | Primary | 70 | Male | 14 | 3.2 | Yes | Spindle | Brachytherapy | 13.2 | No |
| NB 116 | Primary | 85 | Female | 17 | 7.1 | Yes | Spindle | Brachytherapy | 13.4 | No |
| NB 119 | Primary | 69 | Female | 16 | 5.9 | Yes | Spindle | Brachytherapy | 21.8 | No |
| NB 126 | Primary | 34 | Female | 17 | 8.1 | No | Spindle | Brachyterhapy | 22.4 | No |
| MM 046 | Primary | 69 | Female | 22 | 9.0 | Yes | Epithelioid | Enucleation | 32.6 | Yes |
| MM 054 | Primary | 80 | Female | 15 | 6.7 | No | Mixed | Enucleation | 34.6 | Yes |
| MM 055 | Primary | 82 | Female | 19 | 8.6 | Yes | Epithelioid | Enucleation | 81.3 | Yes |
| MM 056 | Primary | 63 | Male | 18 | 11.7 | Ye | Epithelioid | Enucleation | 16.3 | No |
| MM 060 | Primary | 67 | Male | 14 | 9.5 | Yes | Epithelioid | Enucleation | 37.0 | Yes |
| MM 066 | Primary | 47 | Male | 22 | 9.2 | Yes | Mixed | Enucleation | 52.5 | No |
| MM 070 | Primary | 62 | Male | 24 | 15.6 | Yes | Epithelioid | Enucleation | 31.5 | Yes |
| MM 071 | Primary | 63 | Female | N/A | 12.5 | N/A | Spindle | Enucleation | 46.3 | No |
| MM 080 | Primary | 37 | Male | N/A | 11.3 | Yes | Epithelioid | Enucleation | 31.5 | Yes |
| MM 081 | Primary | 65 | Male | 18 | 11.3 | Yes | Epithelioid | Enucleation | 28.2 | Yes |
| MM 083 | Primary | 43 | Male | 5 | 3.7 | Yes | Epithelioid | Enucleation | 51.1 | Yes |
| MM 087 | Primary | 53 | Female | 16 | 5.8 | No | Epithelioid | Enucleation | 17.5 | Yes |
| MM 090 | Primary | 72 | Female | 19 | 14.0 | Yes | Mixed | Enucleation | 27.5 | No |
| MM 091 | Primary | 64 | Male | 17 | 10.2 | Yes | Mixed | Enucleation | 26.4 | Yes |
| MM 100 | Primary | 68 | Male | 18 | 12.3 | Yes | Epithelioid | Enucleation | 16.2 | No |

TABLE 4-continued

Summary of clinical and pathologic data on uveal melanoma patients in the study

| Tumor Number | Source of tumor analyzed | Age at primary tumor diagnosis | Gender | Tumor diameter of primary tumor | Tumor thickness of primary tumor | Cillary body involvement | Pathologic cell type of primary tumor | Treatment of primary tumor | Mons follow-up | Metastasis |
|---|---|---|---|---|---|---|---|---|---|---|
| MM 103 | Primary | 63 | Male | 15 | 12.7 | Yes | Mixed | Enucleation | 33.4 | Yes |
| MM 110 | Primary | 48 | Female | 15 | 8.0 | No | Epithelioid | Enucleation | 37.4 | No |
| MM 120 | Primary | 68 | Female | 20 | 10.4 | Yes | Spindle | Enucleation | 26.7 | Yes |
| MM 121 | Primary | 52 | Female | 17 | 5.8 | Yes | Spindle | Enucleation | 32.3 | Yes |
| MM 125 | Primary | 79 | Female | 18 | 3.9 | No | Mixed | Enucleation | 7. | Yes |
| MM 127 | Primary | 78 | Male | N/A | N/A | N/A | Epithelioid | Enucleation | 20.0 | No |
| MM 128 | Primary | 69 | Female | 8 | 2.4 | No | Mixed | Enucleation | 21.1 | Yes |
| MM 133 | Primary | 54 | Female | 20 | 15.0 | No | Epitheliod | Enucleation | 4.5 | No |
| MM 134 | Primary | 57 | Female | 19 | 9.1 | Yes | Mixed | Enucleation | 6.5 | No |
| MM 135 | Primary | 36 | Female | 20 | NA | Yes | Mixed | Enucleation | 7.1 | No |
| NB 185 | Primary | 85 | Male | 15 | 6.9 | Yes | Epithelioid | Brachytherapy | 3.8 | No |
| NB 191 | Primary | 60 | Female | 9 | 2.7 | No | Spindle | Brachytehrapy | 3.4 | No |
| NB 195 | Primary | 74 | Male | 18 | 9.0 | Yes | Mixed | Biopsy | 3.1 | No |
| NB 199 | Primary | 71 | Female | 13 | 8.7 | Yes | Mixed | Brachytherapy | 1.8 | No |
| NB 200 | Primary | 61 | Femlae | 18 | 4.4 | Yes | Spindle | Brachytherapy | 6.9 | No |
| NB 214 | Primary | 86 | Male | 15 | 4.5 | No | Epithelioid | Brachytherapy | 3.4 | No |
| MM 152M | Metastasis | 68 | Male | 19 | 15.3 | N/A | Epitheliod | Unknown | 4.2 | Yes |
| NB 071M | Metastasis | 51 | Male | 18 | 8.6 | Yes | Epitheliod | Brachytherapy | 36.5 | Yes |
| PVLB | Metastasis | 43 | Female | 18 | 9.0 | N/A | Epithelioid | Unknown | 64.4 | Yes |

Cell Culture:

92.1 (generous gift from Dr. Martine Jager) and Mel290 (generous gift of Dr. Bruce Ksander) human UM cells were grown in RPMI-1640 (Lonza, Walkersville, Md.) supplemented with 10% fetal bovine serum (Invitrogen, Carlsbad, Calif.) and antibiotics. Transfections were performed with HiPerFect (Qiagen, Valencia, Calif.) and Silencer® Select BAP1 (s15820 and s15822) or Control #1 siRNA (Ambion, Austin, Tex.). Knockdown of BAP1 protein levels was confirmed by western blot with antibodies that recognize the BAP1 protein (Santa Cruz, Santa Cruz, Calif.) and alpha-tubulin (Sigma-Aldrich, St. Louis, Mo.). Cell morphology data were collected by digital imaging of phase contrasted cells at 200× magnification. After five days, transfected cells were harvested for RNA and protein analyses.

RNA and Protein Analysis:

All RNA samples were converted to cDNA using the High Capacity cDNA Reverse Transcription kit (Applied Biosystems Inc., Foster City, Calif.) and then pre-amplified for 14 cycles with pooled probes and TaqMan Pre-Amp Master Mix following manufacturer's protocol. Expression of mRNA for individual genes was quantified using the 7900HT Real-Time PCR System with either custom-made primers and iQ SYBRGreen SuperMix (Bio-Rad Laboratories Inc, Hercules, Calif.) for CTNNB1, EDNRB, KIT, SOX10 and UBC (endogenous control) or TaqMan® Gene Expression Assays and Gene Expression Master Mix (Applied Biosystems Inc., Foster City, Calif.) for BAP1, CDH1, LTA4H, LMCD1 and ROBO1. The 15-gene prognostic assay for assignment of tumors to class 1 or class 2 was performed as described elsewhere (26). Staining with BAP1 antibody (201C, the generous gift of Dr. Richard Baer) was performed on 4 µm sections obtained from paraffin-embedded tissue blocks. Statistical significance was assessed using Student's t-test with Medcalc software version 10.4.0.0.

Exome Capture and DNA Sequencing:

gDNA libraries were prepared using the Illumina Pair-End Genomic DNA Sample Prep Kit (Cat #PE-102-1001) according to the manufacturer's instructions. Each paired-end library was enriched for exomic sequence using the Roche-Nimblegen SeqCap EZ Exome kit (Cat #5977215001). The captured genomic DNA fragments were sequenced with the Illumina Genome Analyzer II (GAIIx) for 76-cycles (one lane per sample).

Sequence Analysis:

Illumina Solexa 76 cycle paired-end sequencing data was received as compressed raw reads exported from the Illumina software pipeline (≥1.3). Raw reads were parsed into FASTQ format, and the original raw reads were archived. The FASTQ files were aligned to the hg19 version of the human reference sequence using bowtie. The Bowtie software (v0.12.3) was compiled with g++ (v4.3.3) using the additional compilation switches "–O3—mtune=amdfam10" with pthreads enabled. Mapped reads were directed to a SAM format file for downstream analysis, and unmapped reads were exported to a separate file.

Variant bases were extracted with the samtools software (v0.1.7) with the additional samtools.pl VarFilter switch "–D 1000", and only positions with at least 8 reads and a SNP quality score of at least 20 were considered for further analysis. Filtered variants were stored in a relational database table (MySQL v5.0.75). Known SNPs (dbSNP130 on hg19; exact location known, single base changes) and variants found in 8 HapMap samples (27) were filtered from our variant lists using database queries.

Candidate variants in coding sequence of genes mapping to chromosome 3 were identified and manually annotated for amino acid changes. The 30 base pairs around coding variants were used to query genomic sequence (hg19) to determine if the sequence mapped to multiple genomic locations. Regions with multiple identical mappings were removed. This included the removal of sequences mapping to pseudogenes.

HapMap Variants:

FASTQ files for 8 HapMap individual's exomes (NA19240, NA19129, NA18956, NA18555, NA18517, NA18507, NA12878, NA12156) were downloaded from the NCBI Short Read Archive (3) (accession SRP000910). All reads for each individual were aligned to hg19 (see above). Multiple sequencing runs were merged into one SAM formatted file. Variants were extracted with samtools (see above) and stored in a relational database table.

Sequence Validation:

Oligonucleotide primers were designed from intronic sequences to amplify all coding sequence of BAP1 with the PCR (Table 5). Genomic DNA of tumor and blood from the same patient were subjected to PCR amplification with routine approaches. Sanger DNA sequencing was performed with routine methods to validate variants found with NextGen sequencing, and to query all tumor and matched normal samples for all coding sequences of BAP1. Oligonucleotide primer sequences are available upon request.

TABLE 5

Sequencing primers

| Primers | Seq. | Exon | PCR product size | Location (hg19) |
|---|---|---|---|---|
| BAP1-e1-3-F2 | SEQ ID NO. 15: AGGCTGCTGCTTTCTGTGAG | 1 | 566 bp | chr3: 52443441 + 52444006 |
| BAP1-e1-3-R2 | SEQ ID NO. 16: CGTTGTCTGTGTGTGGGAC | 1 | | |
| BAP1-e4-F | SEQ ID NO. 17: ATGCTGATTGTCTTCTCCCC | 4 | 261 bp | chr3: 52442418-52442678 |
| BAP1-e4-R | SEQ ID NO. 18: CTCCATTTCCACTTCCCAAG | 4 | | |
| BAP1-e5-F | SEQ ID NO. 19: CTTGGGGCTTGCAGTGAG | 5 | 255 bp | chr3: 52441894-52442148 |
| BAP1-e5-R | SEQ ID NO. 20: ATGTGGTAGCATTCCCAGTG | 5 | | |
| BAP1E8L | SEQ ID NO. 21: GGCCTTGCAATTTACAAATCA | 8 | 250 bp | chr3: 52440750 + 52440999 |
| BAP1E8R | SEQ ID NO. 22: TGTCTTCCTTCCCACTCCTG | 8 | | |
| BAP1-e9-F | SEQ ID NO. 23: GGATATCTGCCTCAACCTGATG | 9 | 256 bp | chr3: 52440207-52440462 |
| BAP1-e9-R | SEQ ID NO. 24: GAAGGGAGGAGGAATGCAG | 9 | | |
| BAP1-e10-F | SEQ ID NO. 25: TTCCTTTAGGTCCTCAGCCC | 10 | 287 bp | chr3: 52439727-52440013 |
| BAP1-e10-nest This is a nested primer used for sequencing | SEQ ID NO. 26: CTGAGGTCCACAAGAGGTCC | 10 | | |
| BAP1-e10-R | SEQ ID NO. 27: CAGACATTAGCGGGTGGC | 10 | | |
| BAP1E11L | SEQ ID NO. 28: AAGGGTGCTCCCAGCTTAC | 11 | 227 bp | chr3: 52439107 + 52439333 |
| BAP1E11R | SEQ ID NO. 29: CCTGTGTTCTTGCCCTGTCT | 11 | | |
| BAP1-e12-F | SEQ ID NO. 30: GCTGTGAGTGTCTAGGCTCAG | 12 | 270 bp | chr3: 52438402-52438671 |
| BAP1-e12-R | SEQ ID NO. 31: AGACTGAGATATTCAGGATGGG | 12 | | |
| BAP1-e14-F | SEQ ID NO. 32: CCAAGTGACCACAAAGTGTCC | 14 | 275 bp | chr3: 52437098-52437372 |
| BAP1-e14-R | SEQ ID NO. 33: AGCTCAGGCCTTACCCTCTG | 14 | | |
| BAP1-e17-F2 | SEQ ID NO. 34: CTGAGCACTATGGGCTGAT | 17 | 496 bp | chr3: 52436103 + 52436598 |
| BAP1-e17-R2 | SEQ ID NO. 35: TCTTAACTGGAATGCCCTGC | 17 | | |

TABLE 5-continued

Sequencing primers

| Primers | Seq. | Exon | PCR product size | Location (hg19) |
|---|---|---|---|---|
| BAP1-e13A-F2 | SEQ ID NO. 36: CTGCCTTGGATTGGTCTGAT | 13A | 567 bp | chr3: 52437269 + 52437835 |
| BAP1-e13A-R2 | SEQ ID NO. 37: CAACACCATCAACGTCTTGG | 13A | | |
| BAP1-e13B-F2 | SEQ ID NO. 38: TGATGACAGGACCCAGATCA | 13B | 595 bp | chr3: 52437489 + 52438083 |
| BAP1-e13B-R2 | SEQ ID NO. 39: GCTGTCAGAACTTGATGCCA | 13B | | |
| BAP1-e15-16-F | SEQ ID NO. 40: CTAGCTGCCTATTGCTCGTG | 15-16 | 409 bp | chr3: 52436552-52436960 |
| BAP1-e15-16-R | SEQ ID NO. 41: GAGGGGAGCTGAAGGACAC | 15-16 | | |
| BAP1-e6-7-F | SEQ ID NO. 42: TTTGCCTTCCACCCATAGTC | 6-7 | 412 bp | chr3: 52441134-52441545 |
| BAP1-e6-7-R | SEQ ID NO. 43: AGCTCCCTAGGAGGTAGGC | 6-7 | | |

DNA Methylation Analysis:

Following bisulfite treatment and amplification of genomic DNA from region chr3:52,442,270-52,442,651 (hg19) with bisulfite specific primers, methylation of this region was evaluated with Sequenom's MassARRAY Epityper technology in our core facility (hg.wustl.edu/gtcore/methylation.html). Controls for 0% and 100% methylation were also included. Nine class 1 tumors and ten class 2 tumors were analyzed.

Molecular Classification:

Gene expression data from custom TaqMan Low-Density Arrays were used to determine tumor class assignment, as previously described (26). Briefly, molecular class assignments were made by entering the 12 $\Delta C_t$ values of each sample into the machine learning algorithm GIST 2.3 Support Vector Machine (SVM) (bioinformatics.ubc.ca/svm). SVM was trained using a set of 28 well-characterized uveal melanomas of known molecular class and clinical outcome. SVM creates a hyperplane between the training sample groups (here, class 1 and class 2), then places unknown samples on one or the other side of the hyperplane based upon their gene expression profiles. Confidence is measured by discriminant score, which is inversely proportional to the proximity of the sample to the hyperplane.

Loss of heterozygosity for chromosome 3 was determined using 35 SNPs with minor allele frequencies >0.4 at approximate intervals of 6 megabases across the euchromatic regions of chromosome 3 using the MassARRAY system (Sequenom Inc, San Diego, Calif.), as previously described (25).

Microarray Gene Expression Profiling

Expression data, received as flat files exported from the Illumina software, were analyzed in R (v2.10.1) using Bioconductor packages (Biobase v2.6.1). Non-normalized data were imported into the R environment using the beadarray package (v1.14.0). Expression values were quantile normalized and log 2 transformed using limma (v3.2.3). Each of three independent siRNA knockdown experiments as well as each of three siRNA control experiments was treated as biological replicates. Linear models were fitted to the expression values and expression differences calculated using a contrast comparing the difference in knockdown/control experiments. For each gene log 2 fold change, average expression, and moderated t-statistics were calculated for the defined contrast using the "ebayes" function of the limma package. Nominal p-values were corrected for multiple comparisons using the Benjamini and Hochberg false discovery rate method. Heatmaps were generated using the heatmap function of the R base stats package. Quantile normalized data were filtered down to 29 known discriminating genes plus BAP1. Heatmap colors were generated using the maPalette function of the marray Bioconductor package (v1.24.0), specifying green as low, red as high, and black as mid color values with 20 colors in the palette.

Example 2

Indirect Methods for Detecting BAP1 Loss

BAP1 loss leads to biochemical changes in the cell, such as histone H2A ubiquitination, that may be easier to detect and monitor than direct BAP1 activity.

Figure 8:
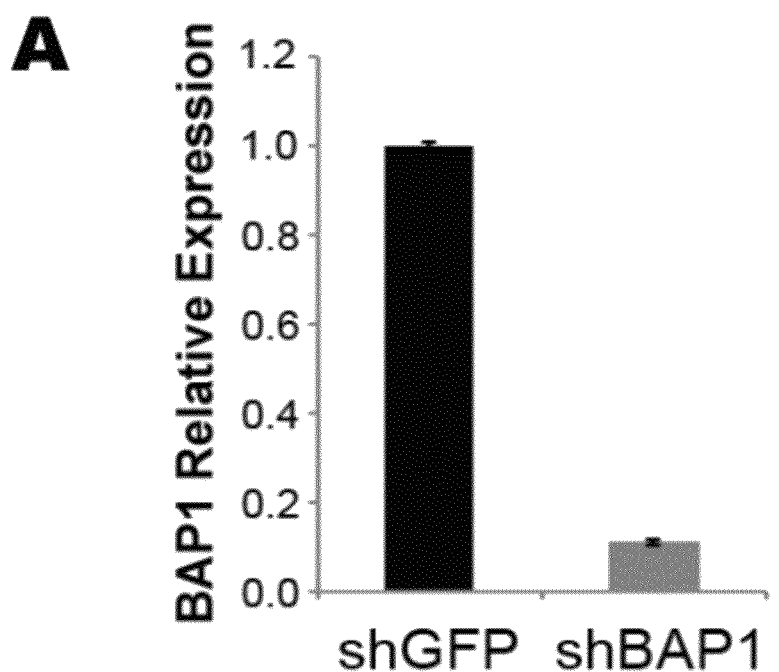
FIG. 8 depicts a bar plot, a Western blot and micrographs for characterizing BAP1 stable knockdown cells.
Figure 8:
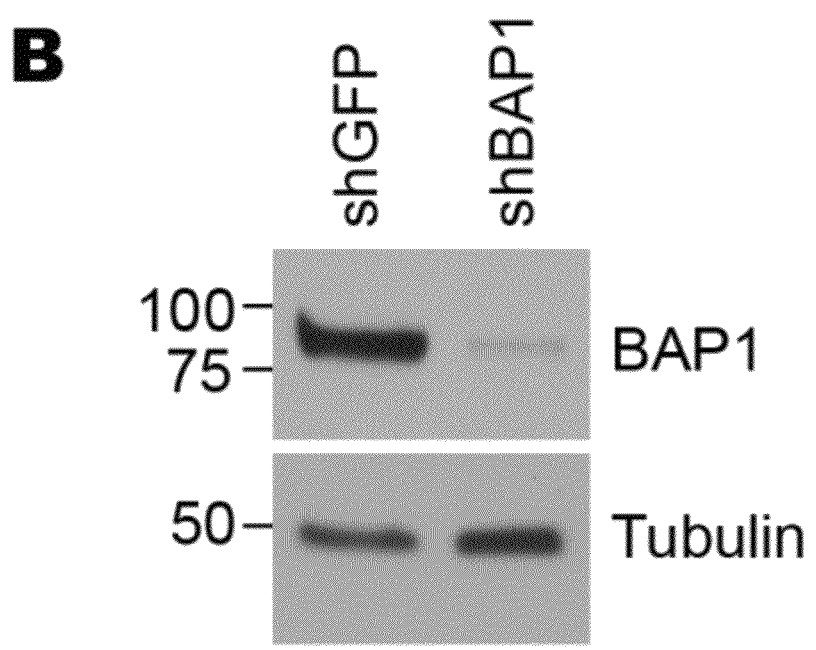
Figure 8:
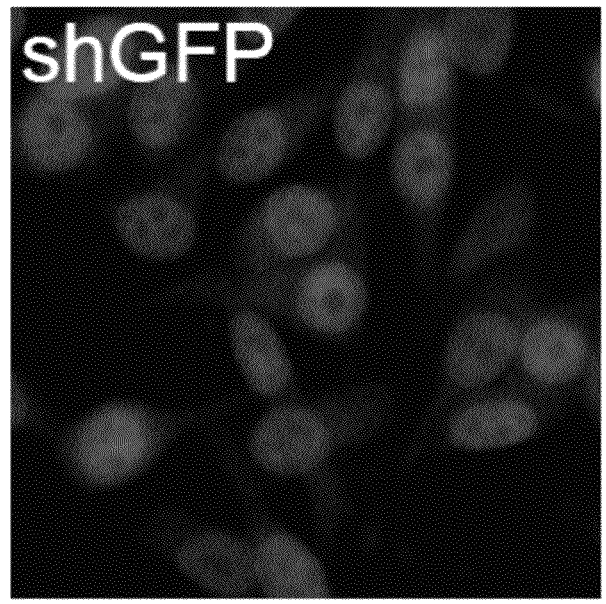
Figure 8:
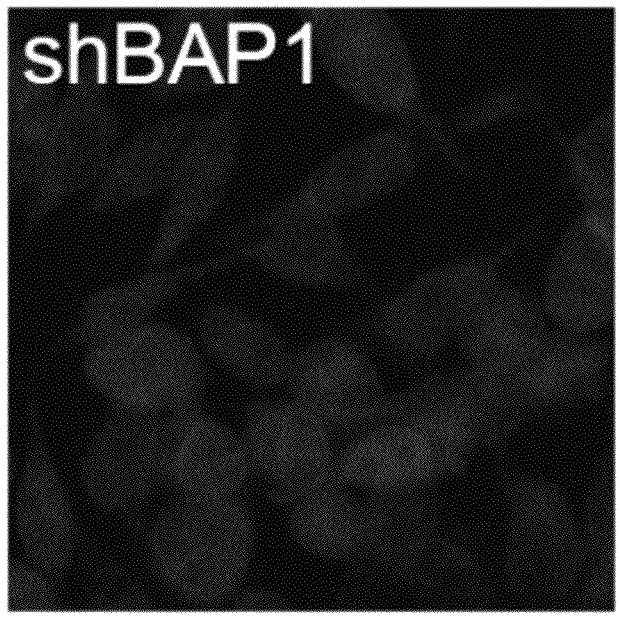
Figure 9:
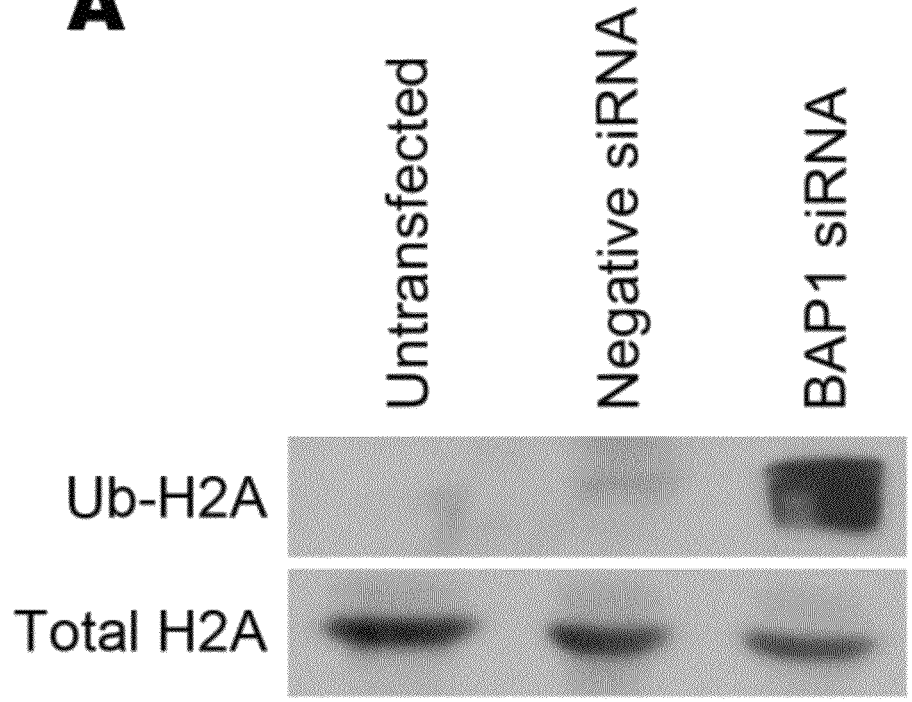
FIG. 9 depicts Western blots and fluorescence immunohistochemical micrographs showing increased ubiquitination of histone H2A.
Figure 9:
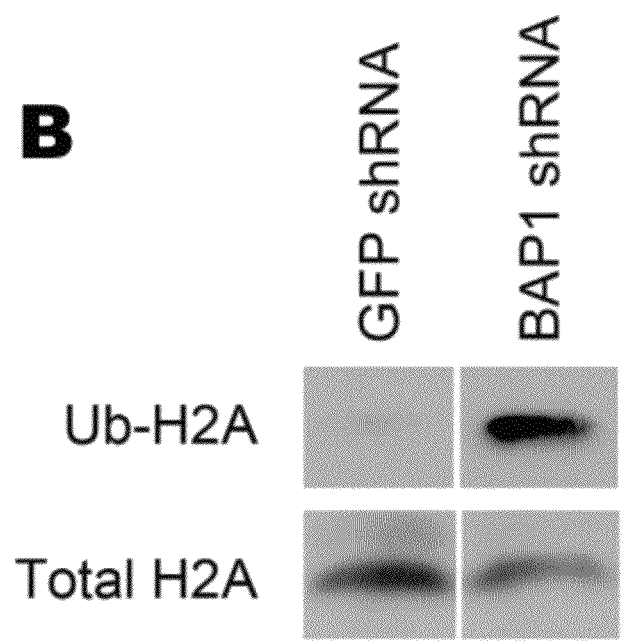
Figure 9:
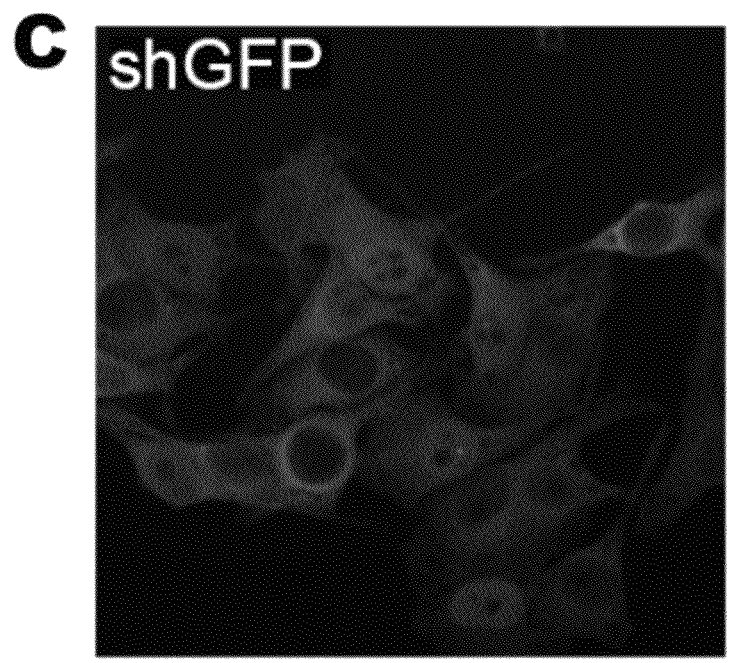
Figure 9:
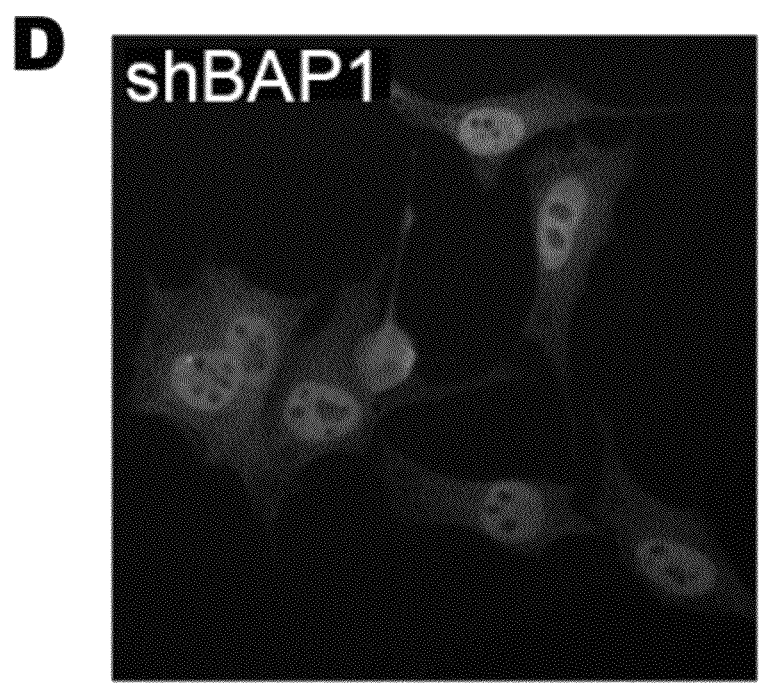

BAP1 stable knockdown cells were produced using lentiviral vectors expressing a short hairpin RNA (shRNA) against BAP1 (FIG. 8). Both transient and stable knockdown of BAP1 lead to increased ubiquitination of histone H2A (FIG. 9). Thus, the measurement of histone H2A ubiquitination levels could be used as a surrogate indicator of BAP1 loss.

Figure 10A:
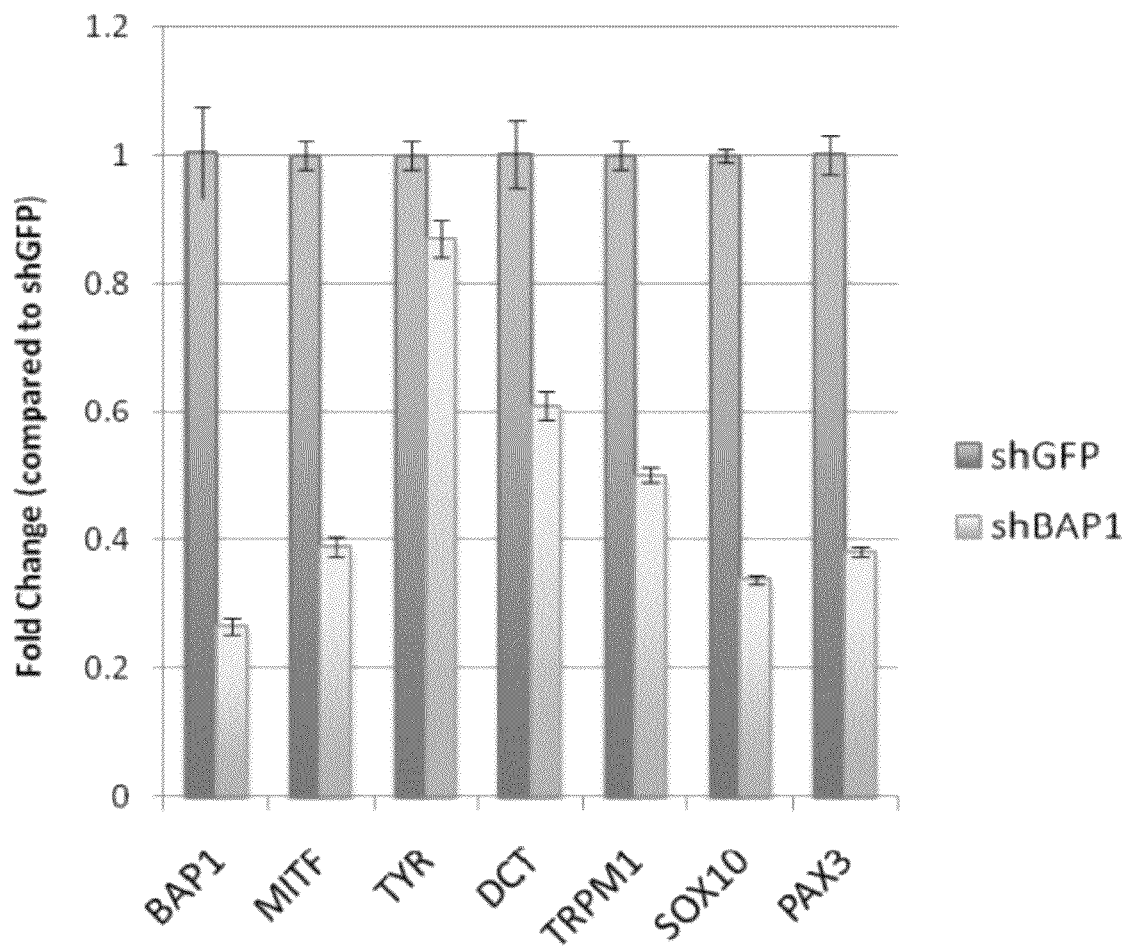
FIG. 10 depicts bar plots showing decreased RNA levels of melanocyte differentiation genes in BAP1 stable knockdown cells.
Figure 10B:
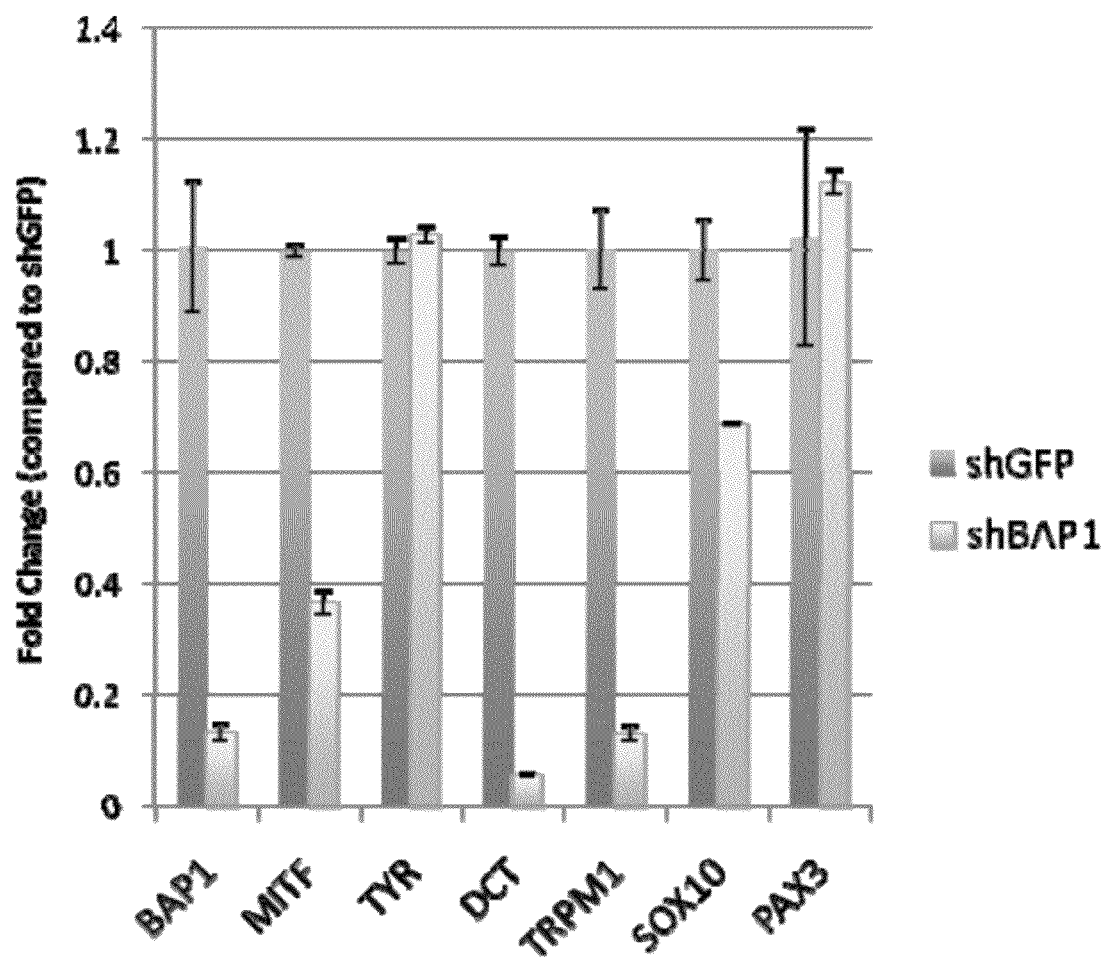
Figure 11:
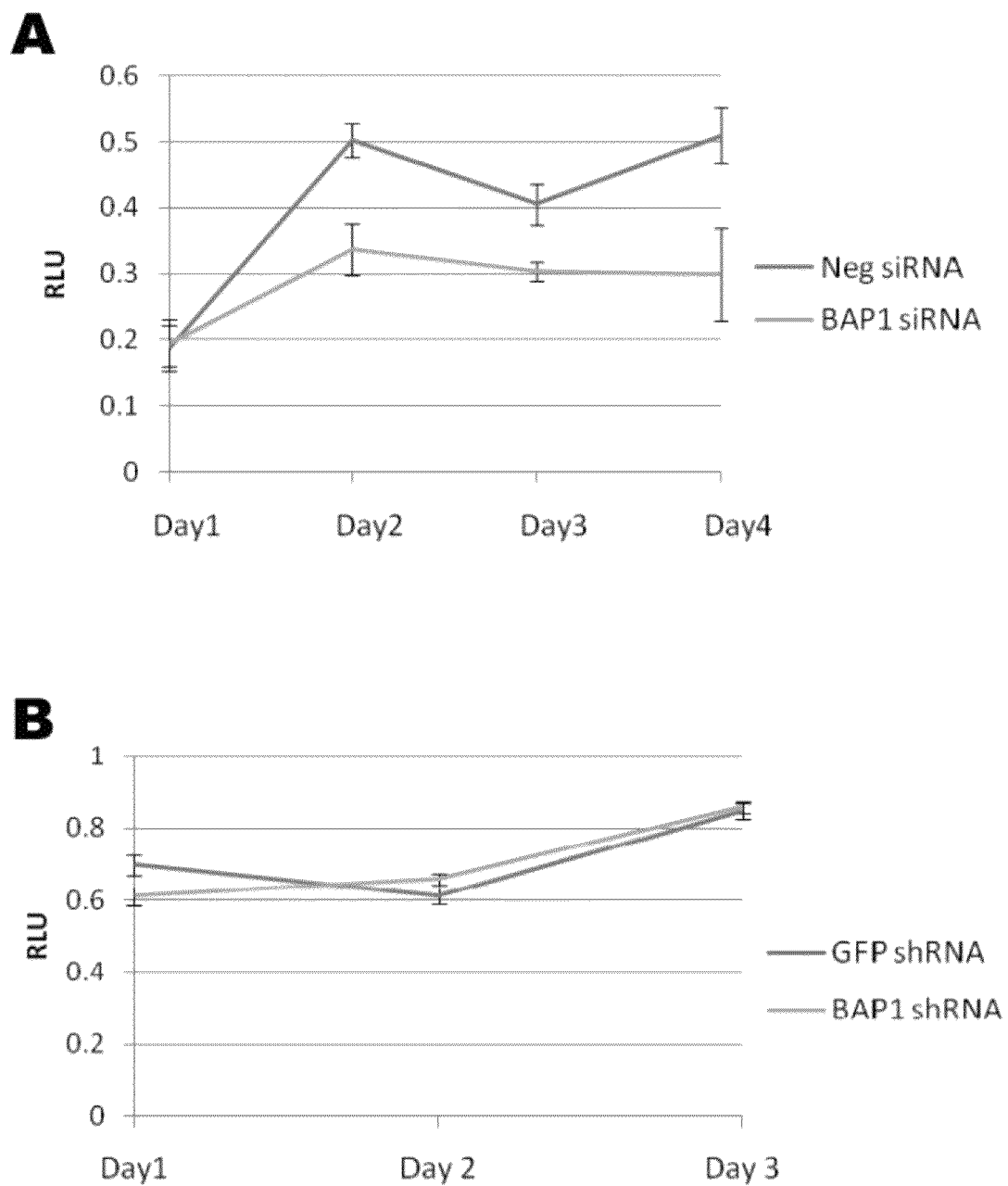
FIG. 11 depicts plots showing that transient knockdown of BAP1 leads to a decrease in cell proliferation.
Figure 11C:
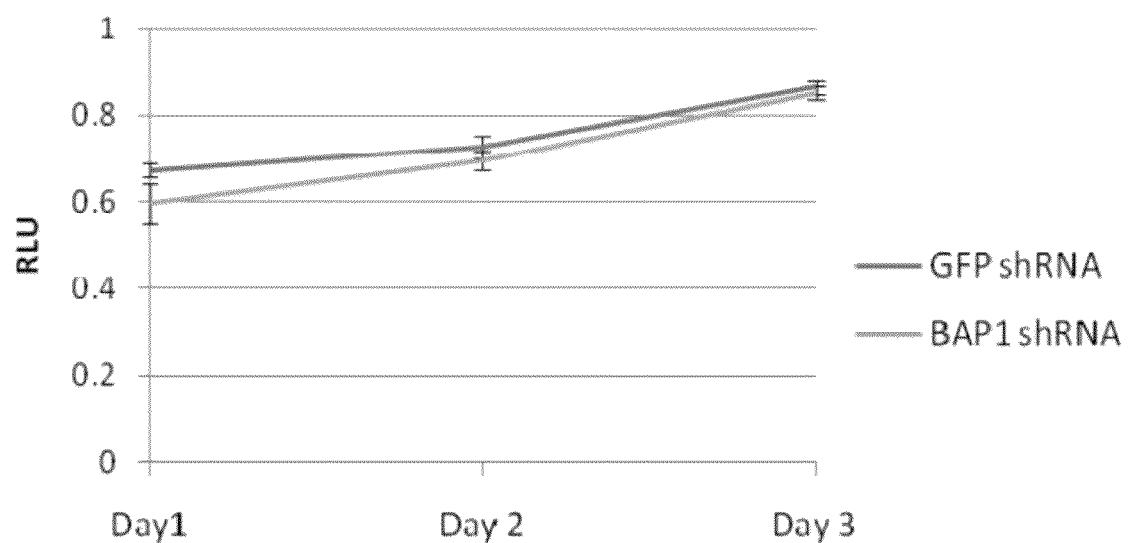
Figure 12A:
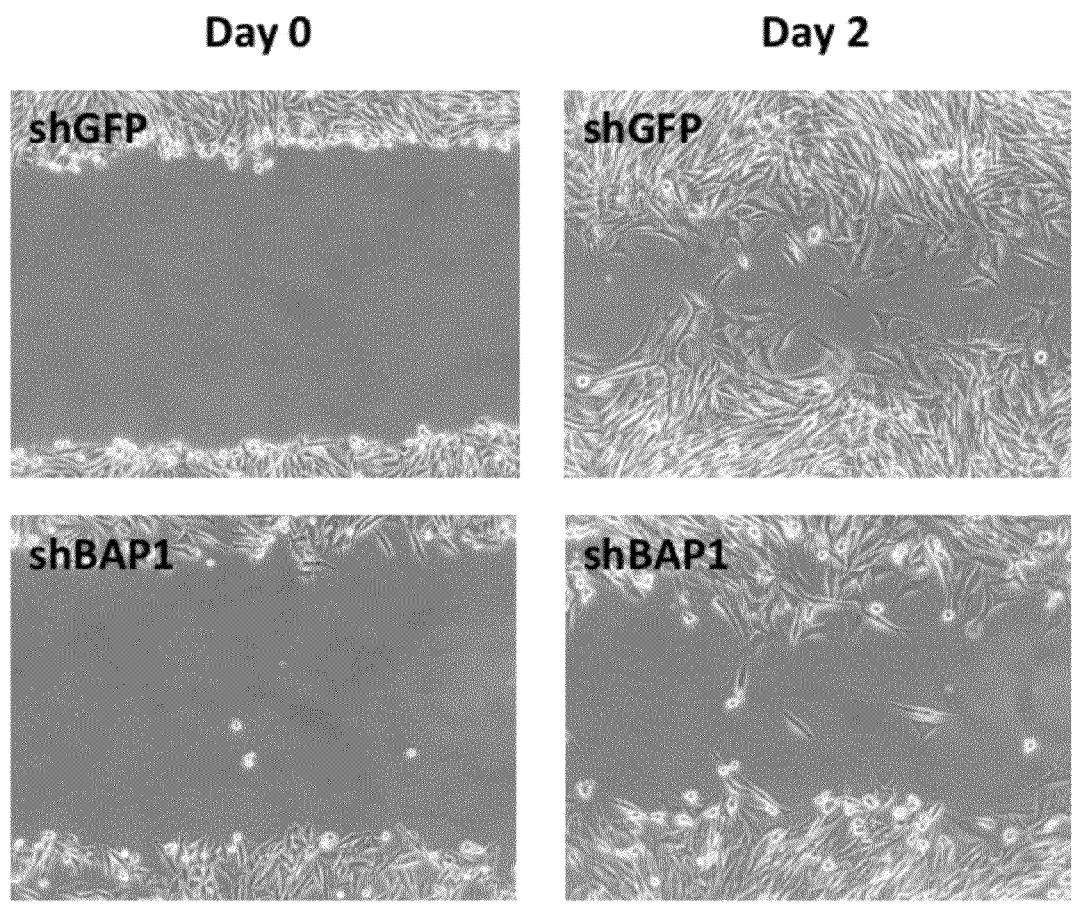
FIG. 12 depicts micrographs and a bar plot showing that loss of BAP1 in culture leads to decreased cell motility.
Figure 12B:
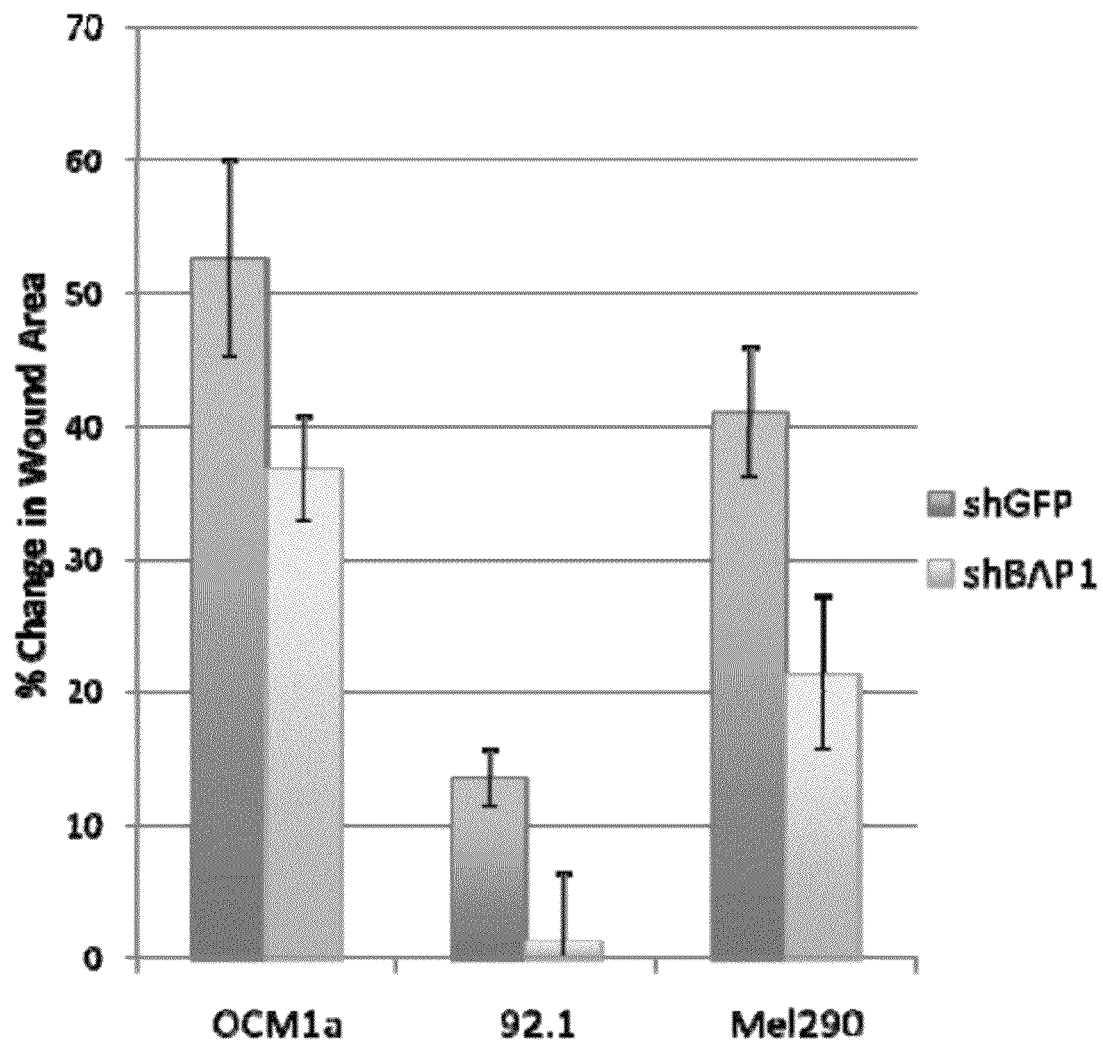
Figure 13:
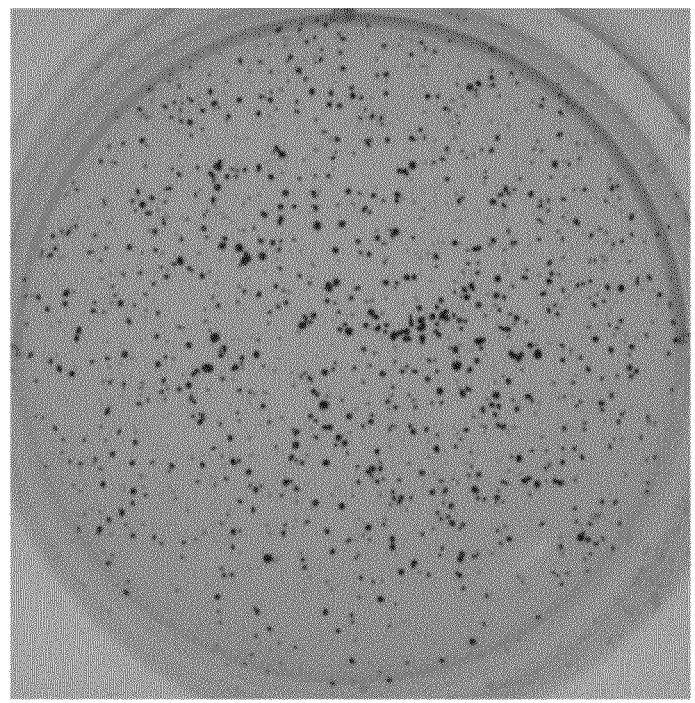
FIG. 13 depicts images of culture plates and a bar plot showing that loss of BAP1 leads to decreased growth in soft agar.
Figure 13:
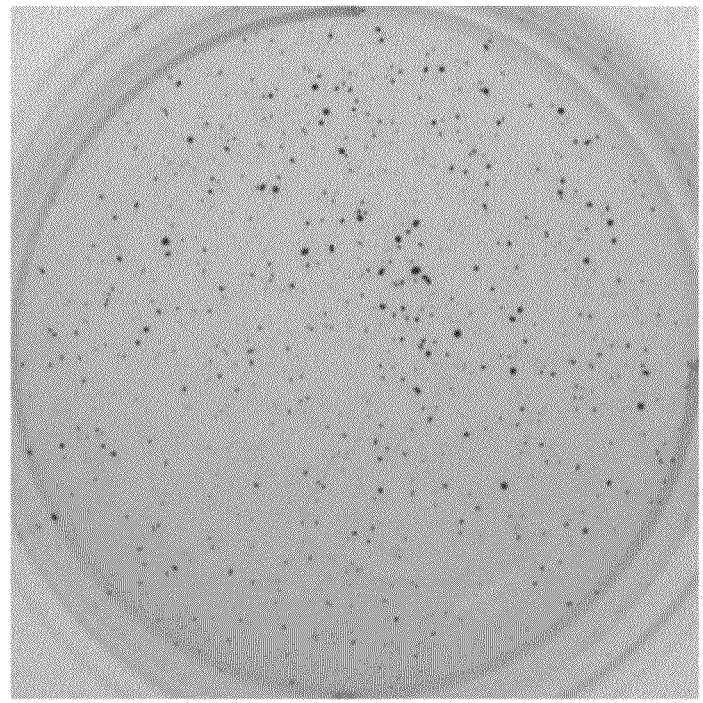
Figure 13C:
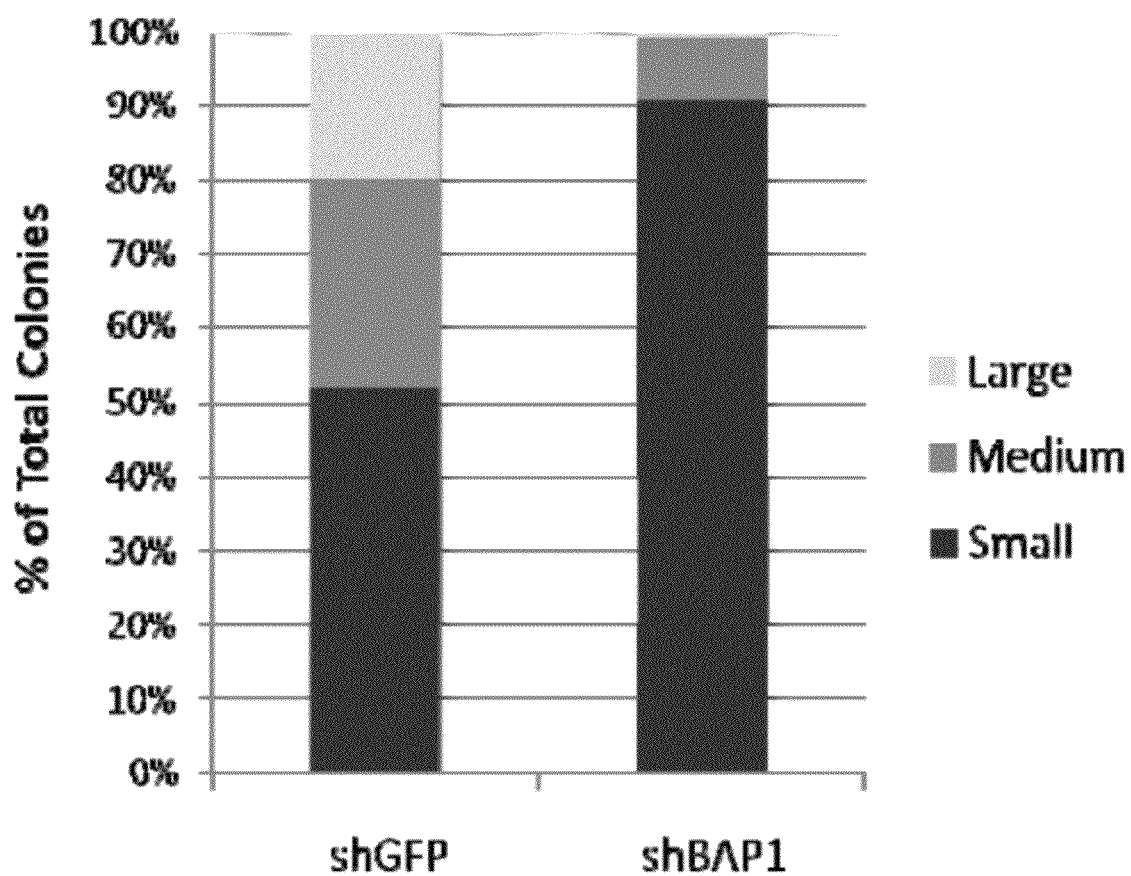
Figure 14:
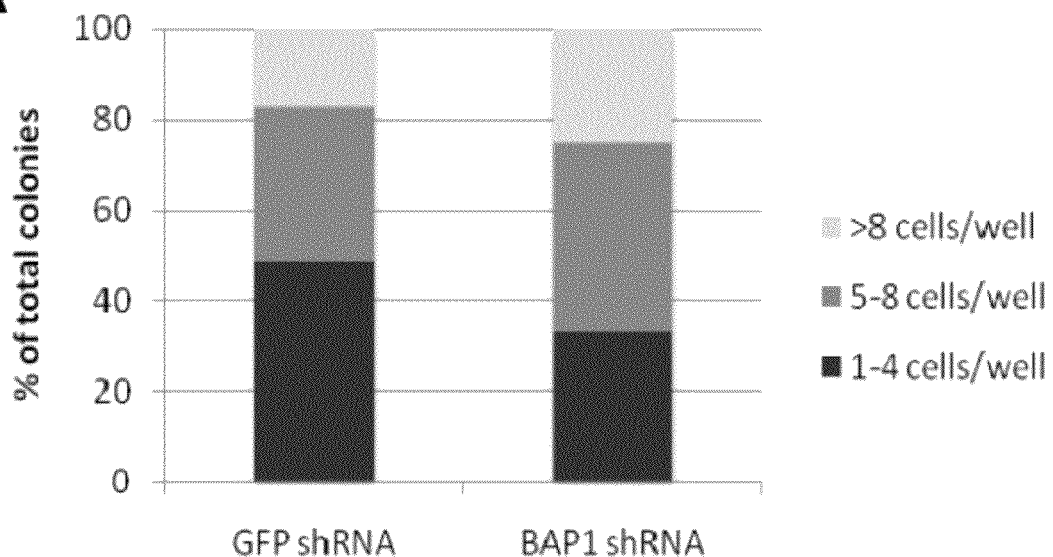
FIG. 14. depicts bar plots showing that loss of BAP1 leads to an increased ability to grow in clonegenic assays.
Figure 14:
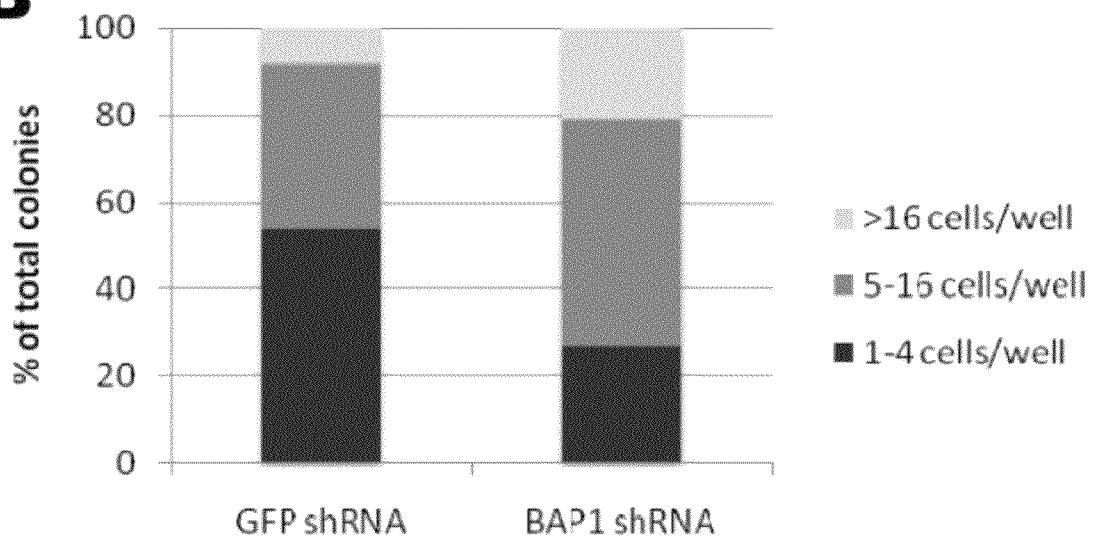
Figure 14:
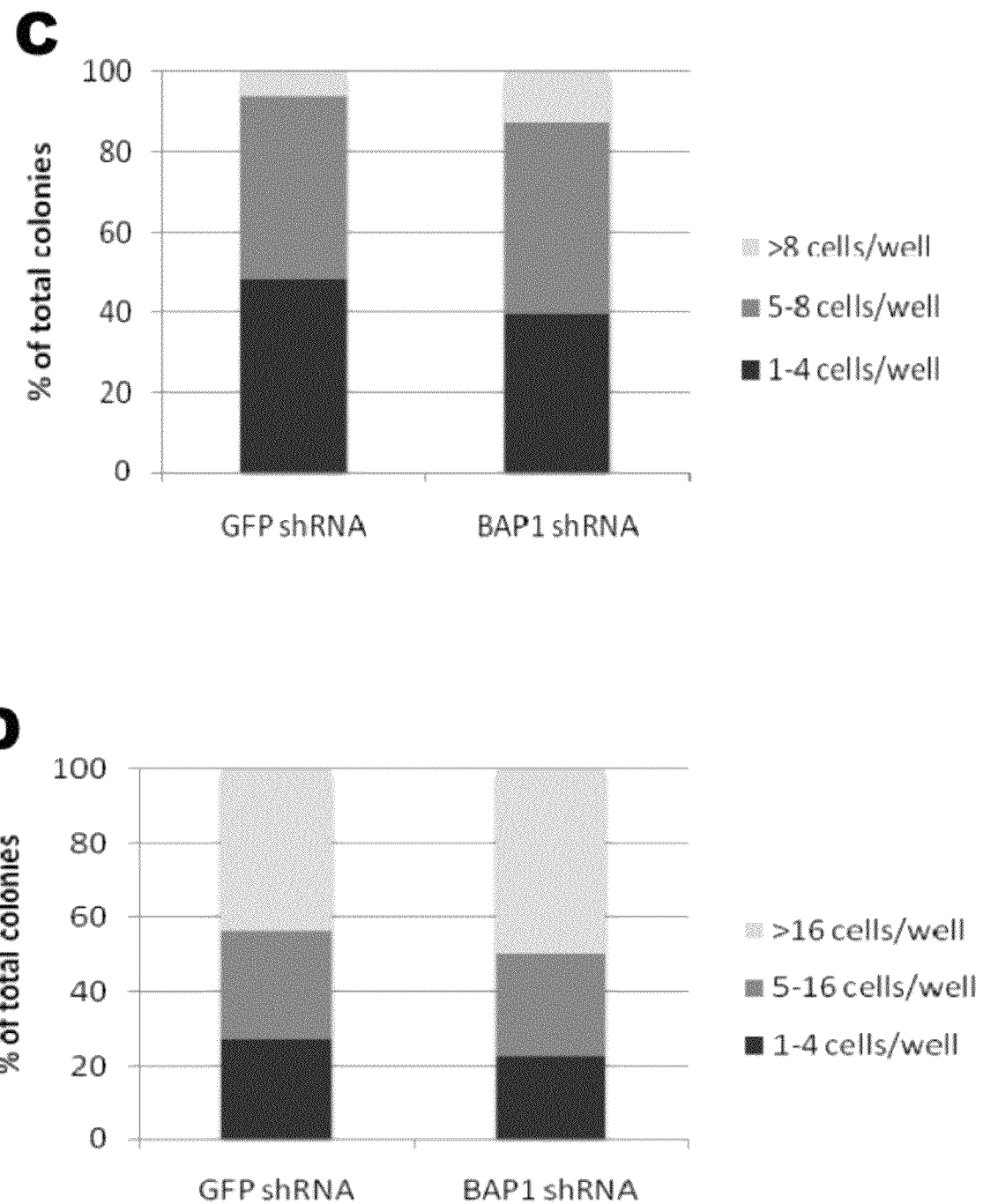
Figure 15:
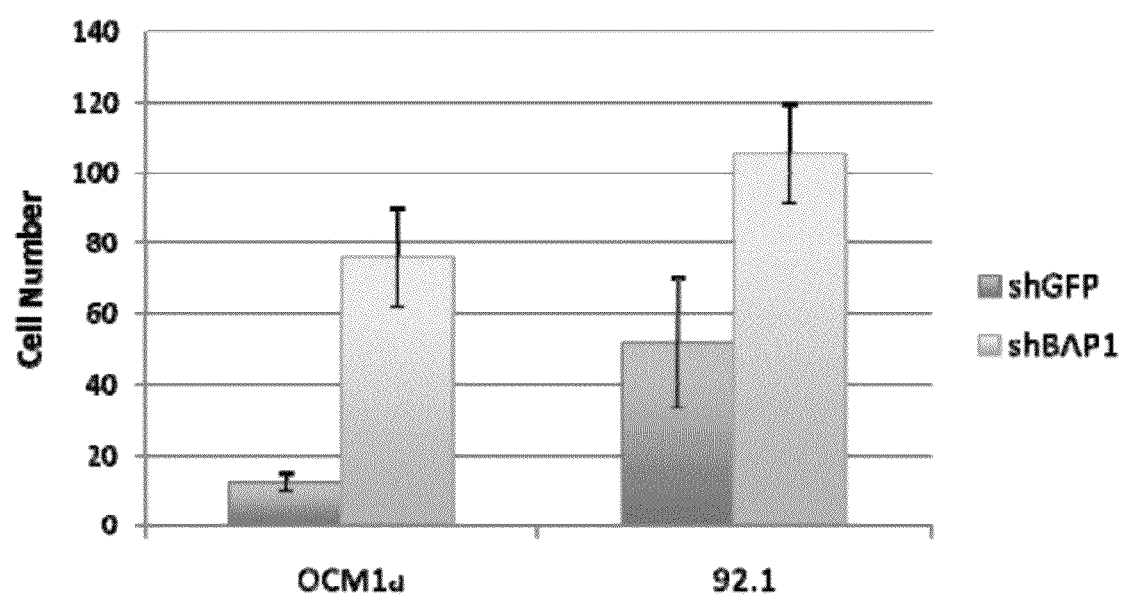
FIG. 15. depicts a bar plot showing that loss of BAP1 leads to increased migration towards a serum attractant.
Figure 16A:
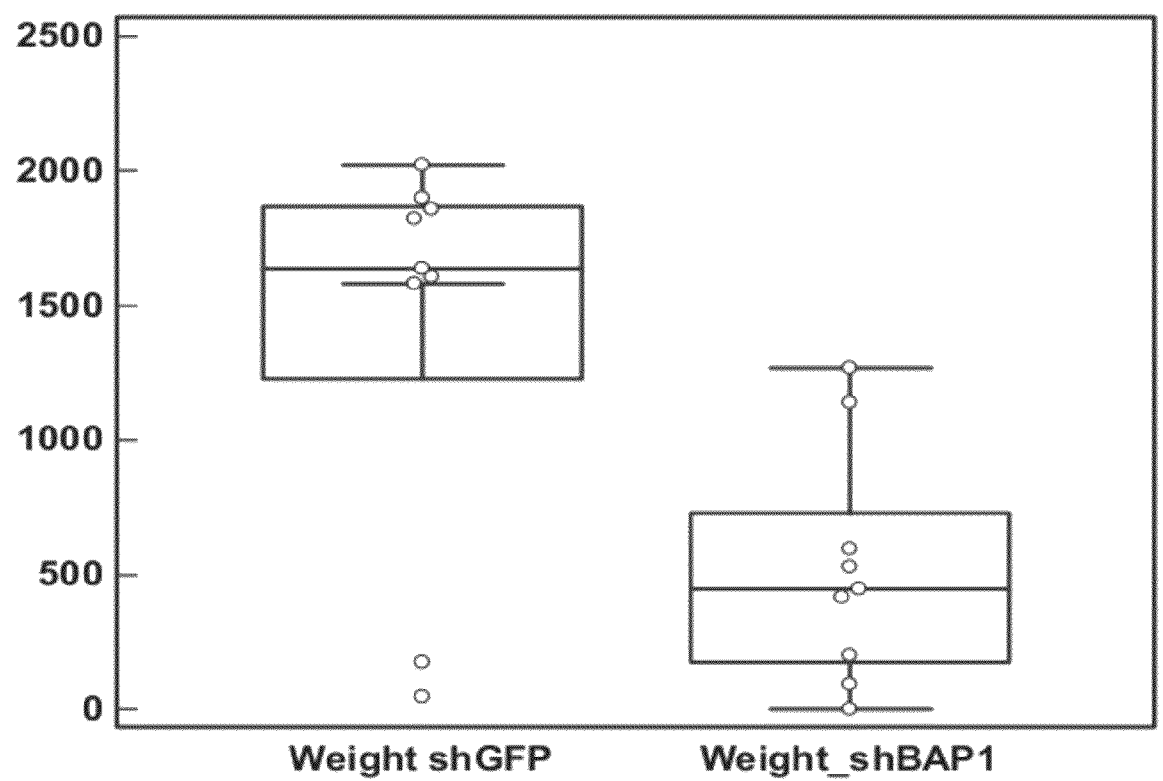
FIG. 16 depicts plots showing that loss of BAP1 in culture leads to decreased tumor growth in the mouse flank.
Figure 16B:
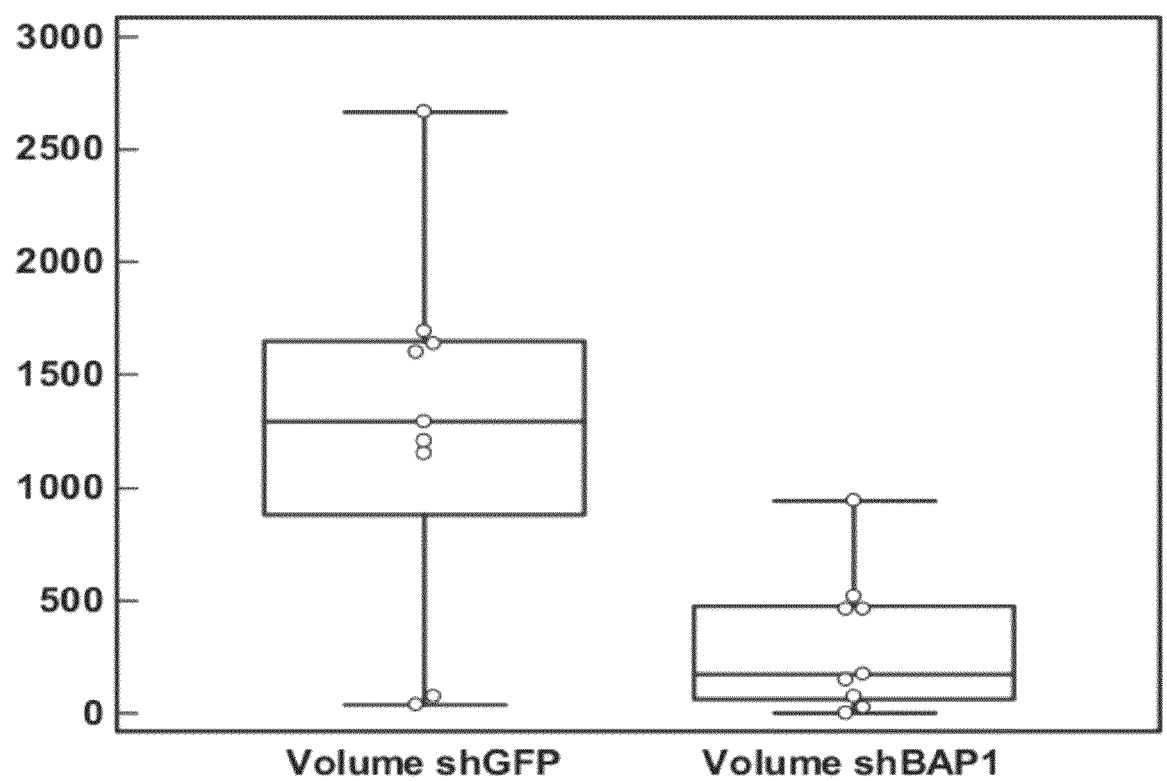
Figure 16C:
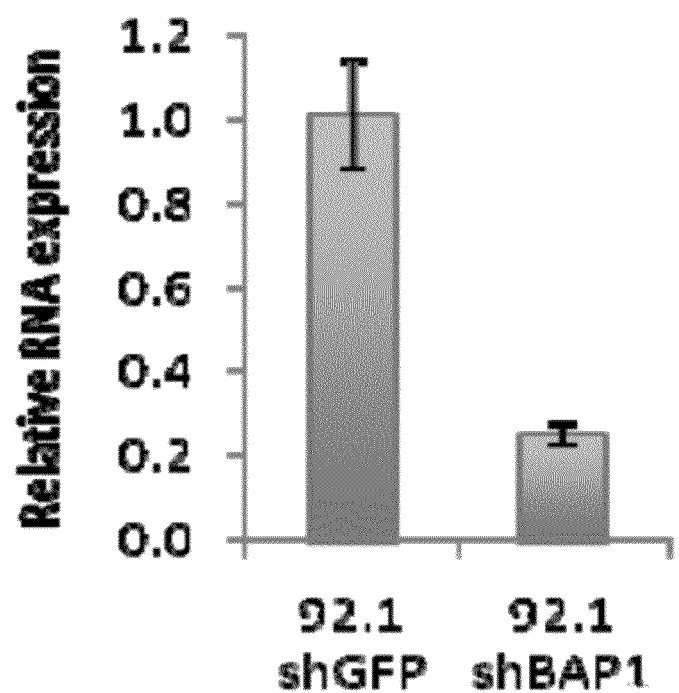
Figure 16D:
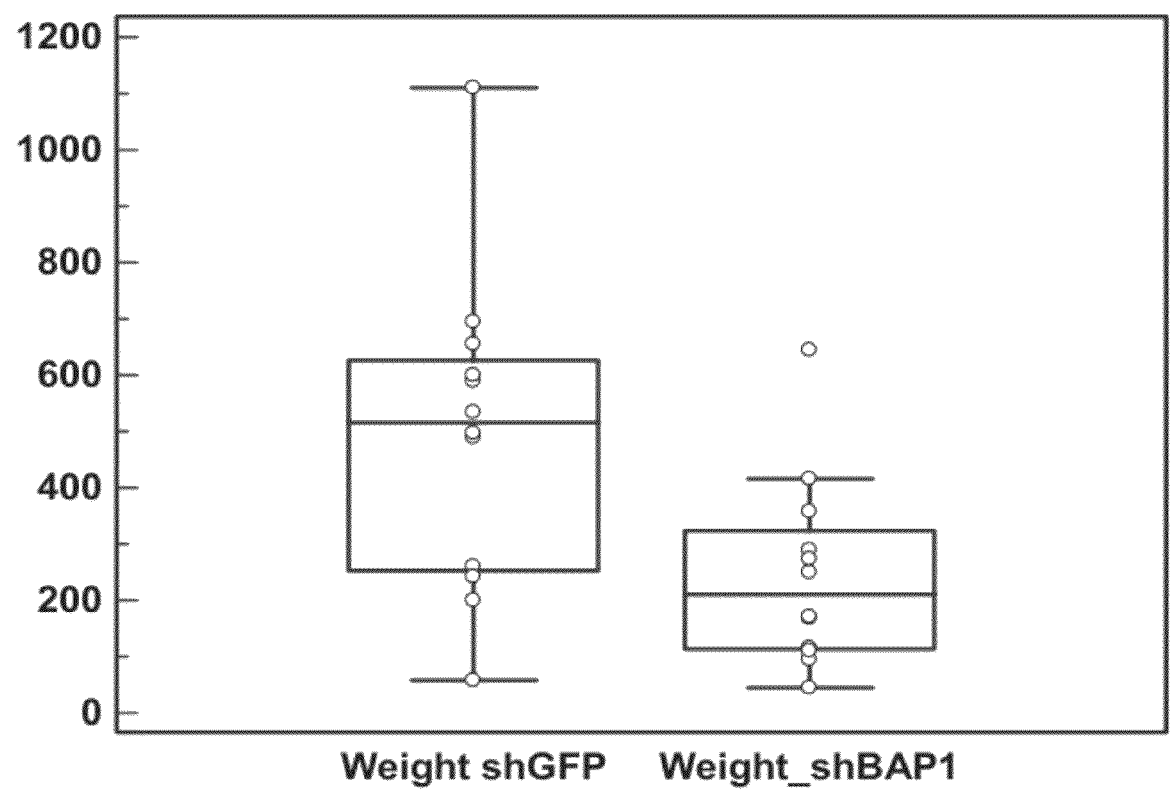
Figure 16E:
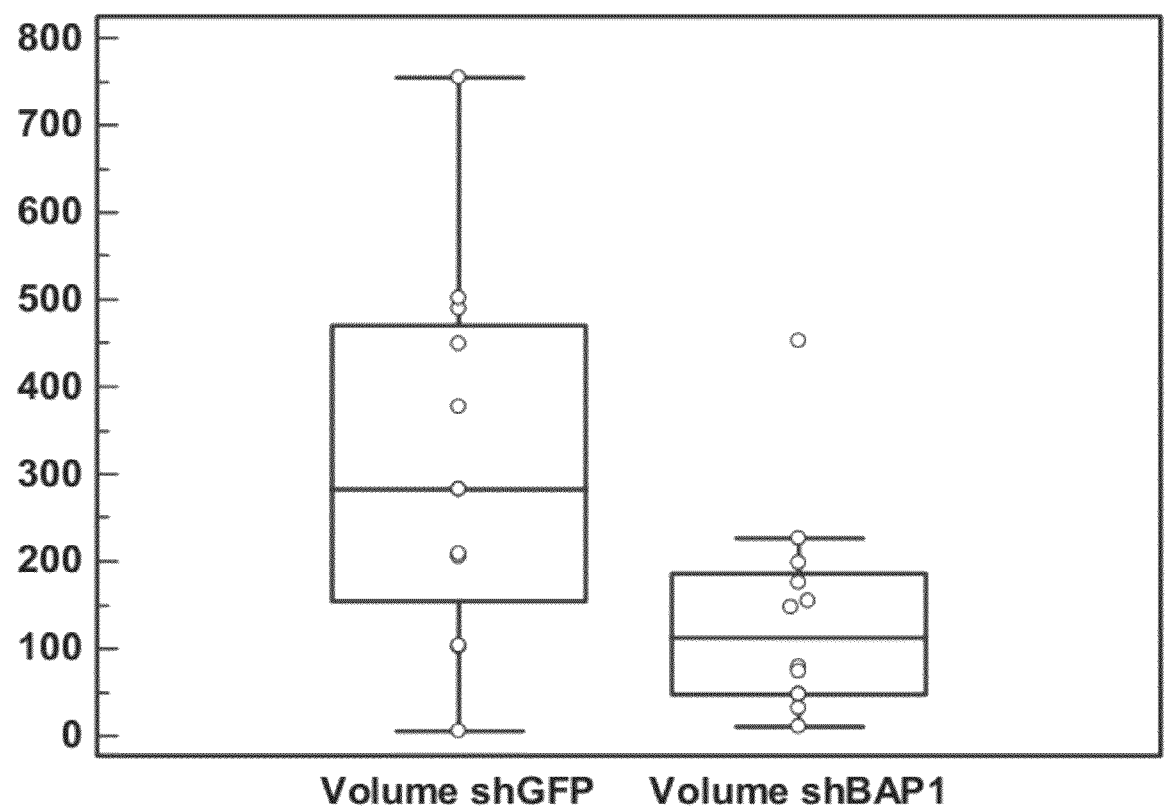
Figure 16F:
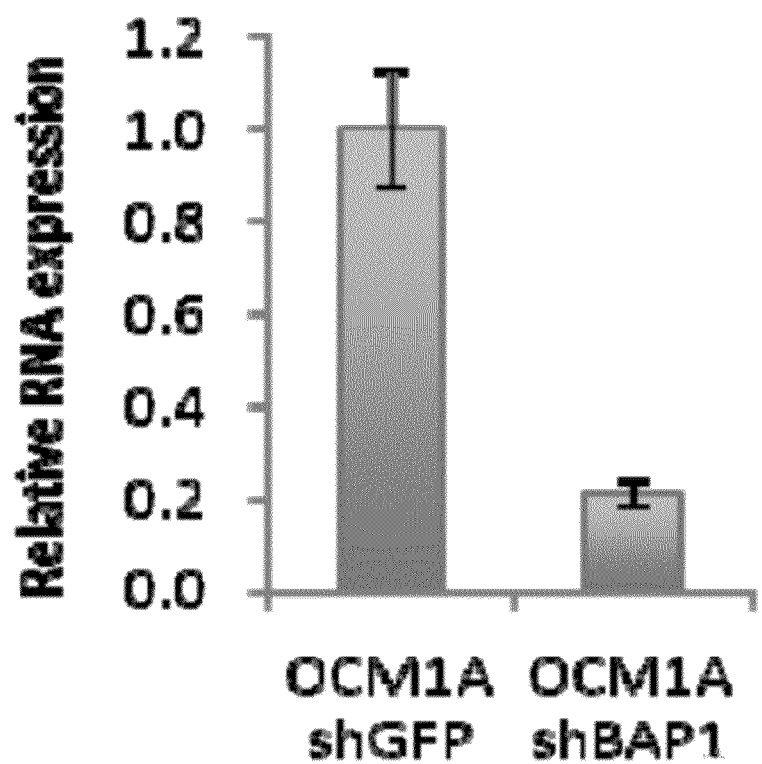
Figure 17A:
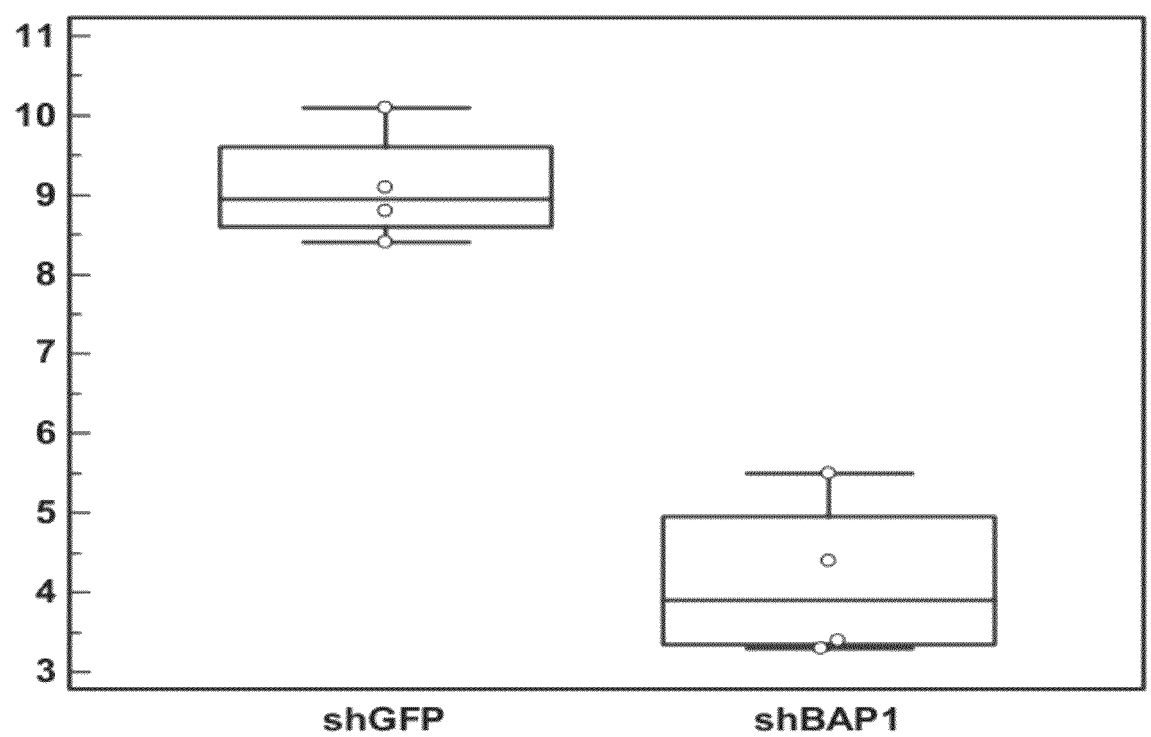
FIG. 17 depicts plots showing that loss of BAP1 in culture leads to decreased tumor growth in the mouse after tail vein injection.
Figure 17B:
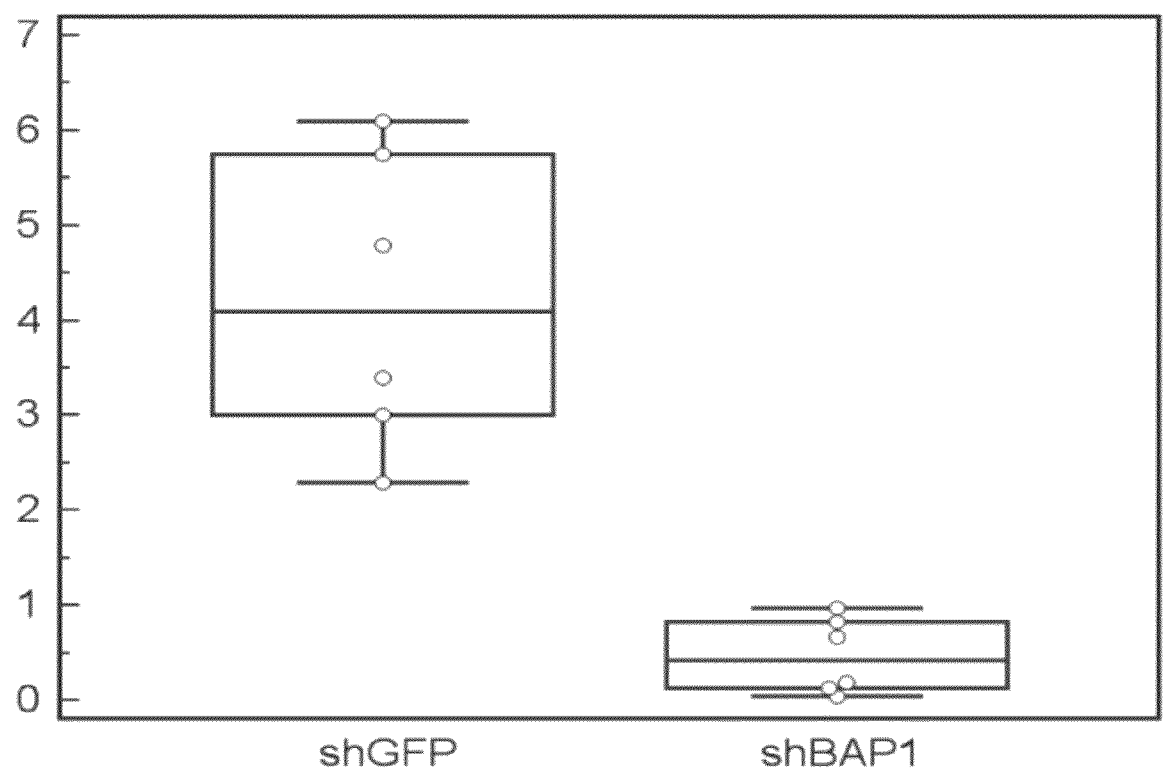
Figure 17C:
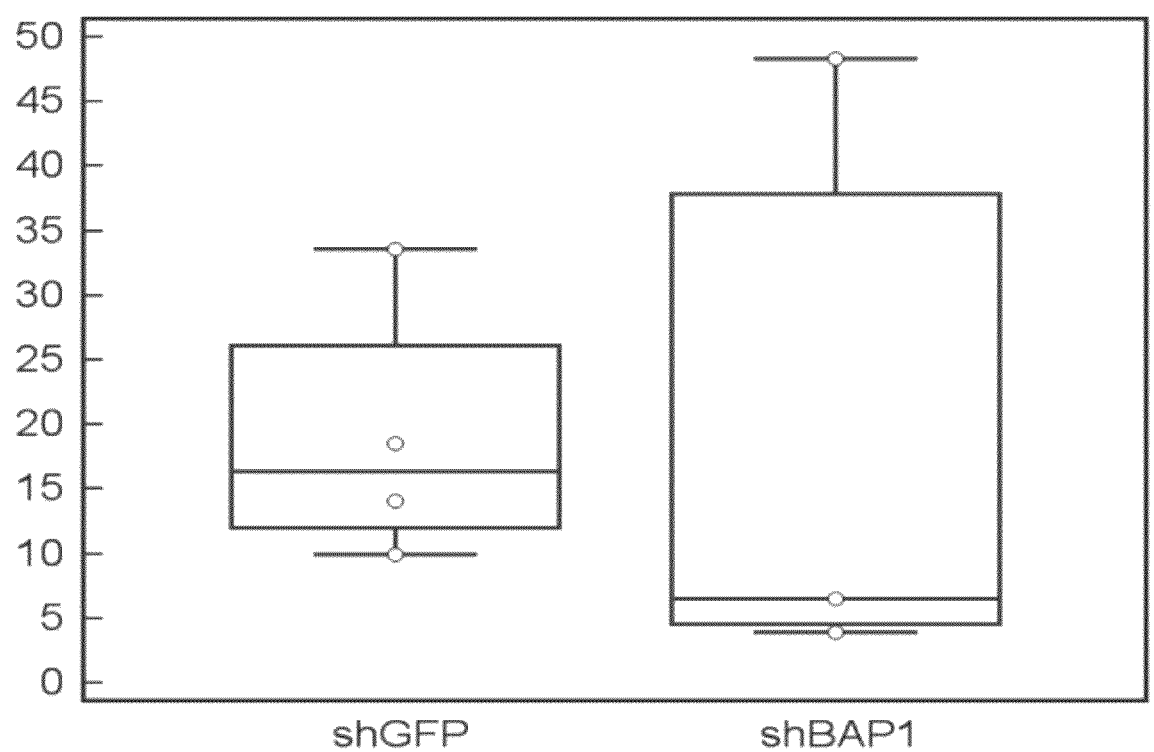
Figure 17D:
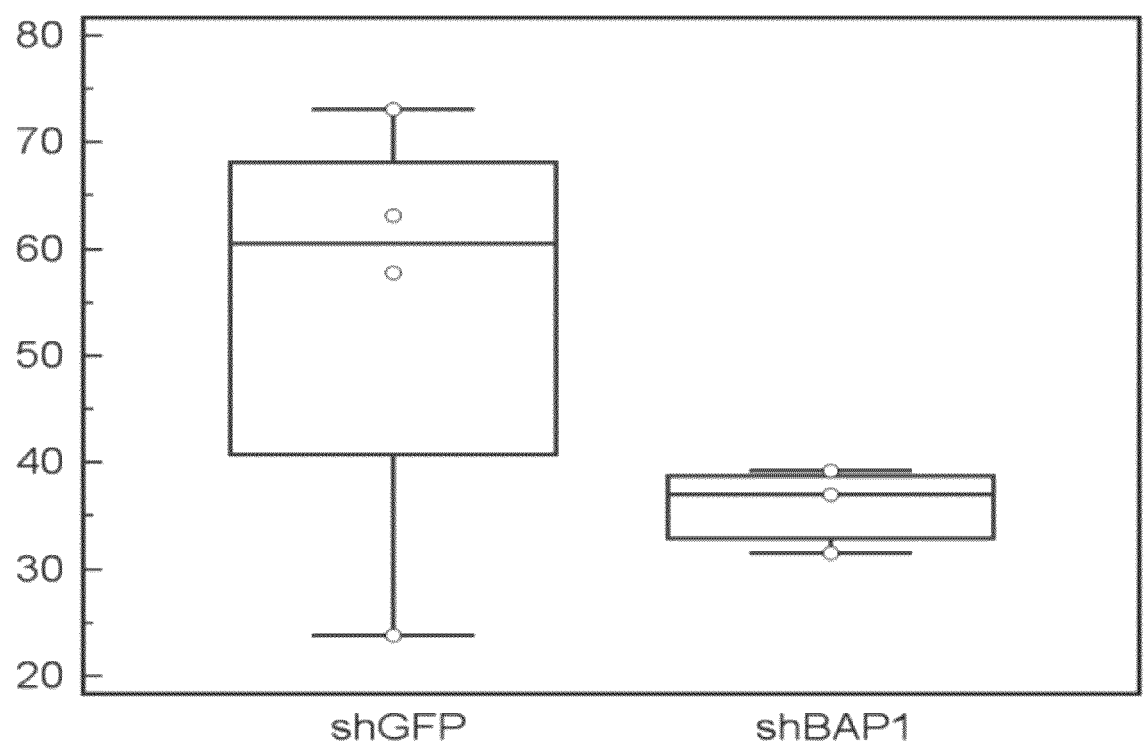

Stable knockdown of BAP1 also leads to a decrease in the RNA levels of melanocyte differentiation genes (FIG. 10). Transient knockdown of BAP1 leads to a decrease in proliferation (FIG. 11) as measured using a BrdU assay. In addition, loss of BAP1 in culture leads to decreased cell motility (FIG. 12) and a decreased growth in soft agar (FIG. 13). On the other hand, loss of BAP1 leads to an increased ability to grow in clonogenic assays (FIG. 14) and increased migration towards a serum attractant (FIG. 15).

Example 3

Loss of BAP1 and Tumor Behavior in Mouse

Uveal melanoma cells stably knocked down for BAP1 using lentiviral expression of shRNA against BAP1 were implanted into mouse flank. Cells deficient for BAP1 grew less rapidly in the mouse flank compared to control cells infected with lentiviral vector expression shRNA against GFP (FIG. 16). After injection into the tail vein of mice, knockdown BAP1 cells exhibited decreased tumor growth (FIG. 17). These findings, coupled with the cell culture experiments above, indicate that the major effect of BAP1 loss in uveal melanoma is not increased proliferation, migration, motility or tumorigenicity upon flank injection.

Example 4

BAP1 Mutations in Cutaneous Melanoma

BAP1 mutations may also be analyzed in cutaneous melanoma tumors as described in the examples and materials and methods above. Cutaneous melanoma tumors analyzed may be atypical moles (Dysplastic Nevus), basal cell carcinomas, blue nevi, cherry hemangiomas, dermatofibromas, halo nevi, keloid and hypertrophic scars, keratoacanthomas, lentigos, metastatic carcinomas of the skin, nevi of ota and ito, melanocytic nevi, seborrheic keratosis, spitz nevi, squamous cell carcinomas, and vitiligos.

Cutaneous melanoma samples and matching normal DNA from peripheral tissue may be analyzed for inactivating mutations in BAP1 using exome capture followed by massively parallel sequencing. Sanger re-sequencing of all BAP1 exons may also be used to further investigate BAP1 mutations. Normal DNA from patients with cutaneous melanoma may be analyzed to determine if BAP1 mutations are somatic or germline in origin. Germline alterations in BAP1 may predispose to cutaneous melanoma.

Mutation status of other genes may also be analyzed in the cutaneous melanoma samples. For example, GNAQ, BRAF, KIT or NRAS mutation status may be determined, and compared to the results obtained for uveal melanoma samples described above.

BAP1 mRNA levels may be analyzed using quantitative RT-PCR. If BAP1 mRNA levels are lower in cutaneous melanoma samples than in normal samples, DNA methylation of the BAP1 locus may be analyzed to determine if the lower mRNA levels may be explained by DNA methylation. BAP1 protein levels in various tumor and normal samples may also be analyzed using immunofluorescence.

BAP1 may be knocked down in cell culture using RNAi. BAP1 mRNA and protein expression levels, cell morphology, and gene expression profiling using microarrays may be used to characterize cell cultures after knock down of BAP1 expression.

Example 5

BAP1 Mutations in the Germline

BAP1 mutations may be detected in germline DNA as a means of detection of affected family members in hereditary syndromes. Germline DNA may be any normal patient DNA such as DNA extracted from peripheral blood lymphocytes or buccal swabs. Standard Sanger sequencing may be used as described in Example 1 above.

For instance, FIG. 18 illustrates a family with stomach cancer, bone cancer, breast cancer, bladder cancer, uveal melanoma, and cutaneous melanoma. The individuals labeled FUM1-01, FUM1-02, FUM1-03, and FUM1-04 were positive for germline BAP1 mutations. These data support the conclusion that germline BAP1 mutations may be used to detect affected family members in hereditary cancers and/or syndromes.

Example 6

BAP1 as a Marker of Circulating Tumors

BAP1 mutations may be detected in peripheral blood as a marker of circulating tumor cells. This may be performed using targeted capture and deep sequencing of BAP1 in blood samples from patients. Targeted capture may be used in combination with NexGen sequencing to provide a very powerful approach for rapidly sequencing genomic regions of interest. The Agilent SureSelect enrichment system is one such method that allows enrichment for genomic regions from a sample of total human genomic DNA. The Agilent system also supports multiplexing of samples in the sequencing reaction, reducing the overall cost of the procedure.

A 1-2 Mb genomic region harboring BAP1 may be captured. This may allow detection of deletions of several exons or the entire gene, as well as the smaller mutations identified in the examples above. Targeted capture with Agilent's SureSelect system starts with querying their eArray web site for a region of interest. This is designed to identify an overlapping set of oligonucleotides (120 mers) over a particular region, but without regions containing repeat (which confound the selection procedure). Agilent synthesizes biotinylated cRNA oligonucleotides and provides them in solution (the probe). 1-3 mg of genomic DNA (the driver) may then be sheared to ~200 bp, end-repaired, A-tailed and ligated to adaptors for Illumina paired-end sequencing. Libraries may be amplified for 6-8 cycles to produce at least 500 ng of product. The product may be hybridized to the oligonucleotide baits to enrich for targeted regions then the resultant hybrids may be captured onto streptavidin-labeled magnetic beads. This may be followed by washing and digestion of the RNA bait. Resultant selection products may be subjected to PCR for 12-14 cycles. At this stage, unique oligonucleotide identifiers may be incorporated into the selected DNAs and their concentrations are determined. These are then adjusted it to a final concentration of 15 pM for sequencing. In this way multiple samples may be loaded onto one flow cell lane on the Sequencer. Currently, 12 samples may be run in a single lane of an Illumina HiSeq2000. Illumina and Nimblegen are also developing similar technologies that could be used for targeted capture. This technology was originally developed by Dr. Michael Lovett (Bashiardes et al. 2005), and instead of oligonucleotides, bacterial artificial chromosomes (BACs) were used as probes. Hence, there are a variety of ways of identifying the genomic target of interest.

Sequences obtained from targeted capture may be analyzed in a similar manner to those obtained from exome-capture and as described elsewhere.

This may potentially be used for (1) non-invasive determination of patients with class 2 high risk uveal melanomas, (2) assessment of circulating tumor burden for uveal, cutaneous or other BAP1 mutant cancer, and (3) to monitor response to therapy.

REFERENCES

1. Landreville S, Agapova O A, Harbour J W. Future Oncol. 2008; 4:629.

2. Onken M D, Worley L A, Tuscan M D, Harbour J W. J Mol Diagn. 2010; 12:461.
3. Finger P T. Arch Pathol Lab Med. 2009; 133:1197.
4. Van Raamsdonk C D, et al. Nature. 2009; 457:599.
5. Onken M D, et al. Invest Ophthalmol Vis Sci. 2008; 49:5230.
6. Bauer J, et al. Br J Cancer. 2009; 101:813.
7. Worley L A, et al. Clin Cancer Res. 2007; 13:1466.
8. Bashiardes S, et al. Nat Methods. 2005; 2:63.
9. Ng S B, et al. Nat Genet. 2010; 42:30.
10. Jensen D E, et al. Oncogene. 1998; 16:1097.
11. Misaghi S, et al. Mol Cell Biol. 2009; 29:2181.
12. Nishikawa H, et al. Cancer Res. 2009; 69:111.
13. Machida Y J, Machida Y, Vashisht A A, Wohlschlegel J A, Dutta A. J Biol Chem. 2009; 284:34179.
14. Tyagi S, Chabes A L, Wysocka J, Herr W. Mol Cell. 2007; 27:107.
15. Gaytan de Ayala Alonso A, et al. Genetics. 2007; 176: 2099.
16. Scheuermann J C, et al. Nature. 2010; 465:243.
17. Wood L D, et al. Science. 2007; 318:1108.
18. Onken M D, et al. Cancer Res. 2006; 66:4602.
19. Onken M D, Worley L A, Ehlers J P, Harbour J W. Cancer Res. 2004; 64:7205.
20. D. Lang et al., Nature 433, 884 (Feb. 24, 2005).
21. L. A. Garraway et al., Nature 436, 117 (Jul. 7, 2005).
22. T. J. Hemesath, E. R. Price, C. Takemoto, T. Badalian, D. E. Fisher, Nature 391, 298 (Jan. 15, 1998).
23. Misaghi S, et al. Journal of Biological Chemistry. 2005; 280:1512.
24. Wang Y, et al. Nucleic Acids Res. 2007; 35:D298.
25. M. D. Onken et al., Clin Cancer Res 13, 2923 (2007).
26. M. D. Onken, L. A. Worley, M. D. Tuscan, J. W. Harbour, J Mol Diagn 12, 461 (2010).
27. S. B. Ng et al., Nature 461, 272 (2009).

What is claimed is:

1. A method for determining the risk of melanoma metastasis in a subject, the method comprising:
   a. collecting a sample comprising a BAP1 nucleic acid from a subject,
   b. sequencing the BAP1 nucleic acid from a cell in the sample,
   c. detecting the presence of a truncating mutation in the BAP1 nucleic acid, wherein the mutation is selected from the group consisting of:
      i) a nonsense mutation selected from the group consisting of Q36X, W196X and Q253X of BAP1;
      ii) an insertion or deletion mutation in exon 2, 4, 5, 6, 7, 8, 9, 11, 12, 13 or 17 of BAP1; and
      iii) a splice acceptor mutation in exon 16 of BAP1; and
   d. identifying the subject as having an increased risk for metastasis when a mutation is detected.

2. The method of claim 1, wherein the melanoma is uveal melanoma.

3. The method of claim 1, wherein the sample is a tumor sample.

4. The method of claim 3, wherein the sample is collected from a primary tumor or from a circulating tumor cell.

5. The method of claim 4, wherein the circulating tumor cell is collected from a bodily fluid.

6. A method for detecting the presence of metastatic melanoma in a subject, the method comprising:
   a. collecting a sample comprising a BAP1 nucleic acid from a subject,
   b. sequencing the BAP1 nucleic acid in the sample or analyzing the level of BAP1 activity in the sample by measuring the level of expression of BAP1 mRNA using quantitative RT-PCR, and
   c. detecting the presence of a truncating mutation in the BAP1 nucleic acid, wherein the mutation is selected from the group consisting of:
      i) a nonsense mutation selected from the group consisting of Q36X, W196X and Q253X of BAP1;
      ii) an insertion or deletion mutation in exon 2, 4, 5, 6, 7, 8, 9, 11, 12, 13 or 17 of BAP1; and
      iii) a splice acceptor mutation in exon 16 of BAP1;
   wherein detection of a mutation indicates the presence of metastatic melanoma, or detecting the level of expression of BAP1 mRNA, wherein detection of a decreased level of expression of BAP1 mRNA compared to a standard indicates the presence of metastatic melanoma in the subject.

7. The method of claim 6, wherein the melanoma is uveal melanoma.

8. The method of claim 6, wherein the sample is collected from a primary tumor or a circulating tumor cell.

9. The method of claim 8, wherein the circulating tumor cell is collected from a bodily fluid.

* * * * *

UNITED STATES PATENT AND TRADEMARK OFFICE
CERTIFICATE OF CORRECTION

PATENT NO. : 9,133,523 B2
APPLICATION NO. : 13/243572
DATED : September 15, 2015
INVENTOR(S) : Anne M. Bowcock et al.

It is certified that error appears in the above-identified patent and that said Letters Patent is hereby corrected as shown below:

In the Specification

Column 1, Lines 14–15 delete:
"R01 CA125970 awarded by the National Cancer Institute, and under P30 EY02687c and AR007279-31A1"
And replace with:
-- CA125970, EY002687, AR007279 --.

Signed and Sealed this
Fifth Day of May, 2020

Andrei Iancu
*Director of the United States Patent and Trademark Office*

SEQUENCE LISTING

```
<160> NUMBER OF SEQ ID NOS: 62

<210> SEQ ID NO 1
<211> LENGTH: 729
<212> TYPE: PRT
<213> ORGANISM: Homo sapiens

<400> SEQUENCE: 1

Met Asn Lys Gly Trp Leu Glu Leu Glu Ser Asp Pro Gly Leu Phe Thr
1               5                   10                  15

Leu Leu Val Glu Asp Phe Gly Val Lys Gly Val Gln Val Glu Glu Ile
            20                  25                  30

Tyr Asp Leu Gln Ser Lys Cys Gln Gly Pro Val Tyr Gly Phe Ile Phe
        35                  40                  45

Leu Phe Lys Trp Ile Glu Glu Arg Arg Ser Arg Arg Lys Val Ser Thr
    50                  55                  60

Leu Val Asp Asp Thr Ser Val Ile Asp Asp Ile Val Asn Asn Met
65                  70                  75                  80

Phe Phe Ala His Gln Leu Ile Pro Asn Ser Cys Ala Thr His Ala Leu
                85                  90                  95

Leu Ser Val Leu Leu Asn Cys Ser Ser Val Asp Leu Gly Pro Thr Leu
            100                 105                 110

Ser Arg Met Lys Asp Phe Thr Lys Gly Phe Ser Pro Glu Ser Lys Gly
        115                 120                 125

Tyr Ala Ile Gly Asn Ala Pro Glu Leu Ala Lys Ala His Asn Ser His
    130                 135                 140

Ala Arg Pro Glu Pro Arg His Leu Pro Glu Lys Gln Asn Gly Leu Ser
145                 150                 155                 160

Ala Val Arg Thr Met Glu Ala Phe His Phe Val Ser Tyr Val Pro Ile
                165                 170                 175

Thr Gly Arg Leu Phe Glu Leu Asp Gly Leu Lys Val Tyr Pro Ile Asp
            180                 185                 190

His Gly Pro Trp Gly Glu Asp Glu Trp Thr Asp Lys Ala Arg Arg
        195                 200                 205

Val Ile Met Glu Arg Ile Gly Leu Ala Thr Ala Gly Glu Pro Tyr His
    210                 215                 220

Asp Ile Arg Phe Asn Leu Met Ala Val Val Pro Asp Arg Arg Ile Lys
225                 230                 235                 240

Tyr Glu Ala Arg Leu His Val Leu Lys Val Asn Arg Gln Thr Val Leu
```

-continued

```
            245                 250                 255
Glu Ala Leu Gln Gln Leu Ile Arg Val Thr Gln Pro Glu Leu Ile Gln
                260                 265                 270
Thr His Lys Ser Gln Glu Ser Gln Leu Pro Glu Glu Ser Lys Ser Ala
            275                 280                 285
Ser Asn Lys Ser Pro Leu Val Leu Glu Ala Asn Arg Ala Pro Ala Ala
        290                 295                 300
Ser Glu Gly Asn His Thr Asp Gly Ala Glu Ala Ala Gly Ser Cys
305                 310                 315                 320
Ala Gln Ala Pro Ser His Ser Pro Asn Lys Pro Lys Leu Val Val
                325                 330                 335
Lys Pro Pro Gly Ser Ser Leu Asn Gly Val His Pro Asn Pro Thr Pro
                340                 345                 350
Ile Val Gln Arg Leu Pro Ala Phe Leu Asp Asn His Asn Tyr Ala Lys
                355                 360                 365
Ser Pro Met Gln Glu Glu Glu Asp Leu Ala Ala Gly Val Gly Arg Ser
        370                 375                 380
Arg Val Pro Val Arg Pro Gln Gln Tyr Ser Asp Asp Glu Asp Asp
385                 390                 395                 400
Tyr Glu Asp Asp Glu Asp Asp Val Gln Asn Thr Asn Ser Ala Leu
                    405                 410                 415
Arg Tyr Lys Gly Lys Gly Thr Gly Lys Pro Gly Ala Leu Ser Gly Ser
                420                 425                 430
Ala Asp Gly Gln Leu Ser Val Leu Gln Pro Asn Thr Ile Asn Val Leu
        435                 440                 445
Ala Glu Lys Leu Lys Glu Ser Gln Lys Asp Leu Ser Ile Pro Leu Ser
    450                 455                 460
Ile Lys Thr Ser Ser Gly Ala Gly Ser Pro Ala Val Ala Val Pro Thr
465                 470                 475                 480
His Ser Gln Pro Ser Pro Thr Pro Ser Asn Glu Ser Thr Asp Thr Ala
                485                 490                 495
Ser Glu Ile Gly Ser Ala Phe Asn Ser Pro Leu Arg Ser Pro Ile Arg
                500                 505                 510
Ser Ala Asn Pro Thr Arg Pro Ser Ser Pro Val Thr Ser His Ile Ser
        515                 520                 525
Lys Val Leu Phe Gly Glu Asp Asp Ser Leu Leu Arg Val Asp Cys Ile
    530                 535                 540
Arg Tyr Asn Arg Ala Val Arg Asp Leu Gly Pro Val Ile Ser Thr Gly
545                 550                 555                 560
Leu Leu His Leu Ala Glu Asp Gly Val Leu Ser Pro Leu Ala Leu Thr
                565                 570                 575
Glu Gly Gly Lys Gly Ser Ser Pro Ser Ile Arg Pro Ile Gln Gly Ser
                580                 585                 590
Gln Gly Ser Ser Ser Pro Val Glu Lys Glu Val Val Glu Ala Thr Asp
        595                 600                 605
Ser Arg Glu Lys Thr Gly Met Val Arg Pro Gly Glu Pro Leu Ser Gly
    610                 615                 620
Glu Lys Tyr Ser Pro Lys Glu Leu Leu Ala Leu Leu Lys Cys Val Glu
625                 630                 635                 640
Ala Glu Ile Ala Asn Tyr Glu Ala Cys Leu Lys Glu Glu Val Glu Lys
                645                 650                 655
Arg Lys Lys Phe Lys Ile Asp Asp Gln Arg Arg Thr His Asn Tyr Asp
                660                 665                 670
```

Glu Phe Ile Cys Thr Phe Ile Ser Met Leu Ala Gln Glu Gly Met Leu
              675                 680                 685

Ala Asn Leu Val Glu Gln Asn Ile Ser Val Arg Arg Arg Gln Gly Val
          690                 695                 700

Ser Ile Gly Arg Leu His Lys Gln Arg Lys Pro Asp Arg Arg Lys Arg
705                 710                 715                 720

Ser Arg Pro Tyr Lys Ala Lys Arg Gln
                725

<210> SEQ ID NO 2
<211> LENGTH: 3599
<212> TYPE: DNA
<213> ORGANISM: Homo sapiens

<400> SEQUENCE: 2

```
gcccgttgtc tgtgtgtggg actgaggggc cccggggggcg gtggggggctc ccggtgggggg    60
cagcggtggg gagggagggc ctggacatgg cgctgagggg ccgccccgcg ggaagatgaa   120
taagggctgg ctggagctgg agagcgaccc aggcctcttc accctgctcg tggaagattt   180
cggtgtcaag gggggtgcaag tggaggagat ctacgacctt cagagcaaat gtcagggccc   240
tgtatatgga tttatcttcc tgttcaaatg gatcgaagag cgccggtccc ggcgaaaggt   300
ctctaccttg gtggatgata cgtccgtgat tgatgatgat attgtgaata acatgttctt   360
tgcccaccag ctgataccca actcttgtgc aactcatgcc ttgctgagcg tgctcctgaa   420
ctgcagcagc gtggacctgg gacccaccct gagtcgcatg aaggacttca ccaagggttt   480
cagccctgag agcaaaggat atgcgattgg caatgccccg gagttggcca aggcccataa   540
tagccatgcc aggcccgagc cacgccacct ccctgagaag cagaatggcc ttagtgcagt   600
gcggaccatg gaggcgttcc actttgtcag ctatgtgcct atcacaggcc ggctctttga   660
gctggatggg ctgaaggtct acccccattga ccatgggccc tgggggggagg acgaggagtg   720
gacagacaag gcccggcggg tcatcatgga gcgtatcggc ctcgccactg caggggagcc   780
ctaccacgac atccgcttca acctgatggc agtggtgccc gaccgcagga tcaagtatga   840
ggccaggctg catgtgctga aggtgaaccg tcagacagta ctagaggctc tgcagcagct   900
gataagagta acacagccag agctgattca gacccacaag tctcaagagt cacagctgcc   960
tgaggagtcc aagtcagcca gcaacaagtc ccgctggtg ctggaagcaa cagggcccc    1020
tgcagcctct gagggcaacc acacagatgg tgcagaggag gcggctggtt catgcgcaca   1080
agccccatcc cacagccctc ccaacaaacc caagctagtg gtgaagcctc aggcagcag   1140
cctcaatggg gttcacccca ccccactcc cattgtccag cggctgccgg cctttctaga   1200
caatcacaat tatgccaagt cccccatgca ggaggaagaa gacctggcgg caggtgtggg   1260
ccgcagccga gttccagtcc gcccaccca gcagtactca gatgatgagg atgactatga   1320
ggatgacgag gaggatgacg tgcagaacac caactctgcc cttaggtata gggggaaggg   1380
aacagggaag ccaggggcat tgagcggttc tgctgatggg caactgtcag tgctgcagcc   1440
caacaccatc aacgtcttgg ctgagaagct caaagagtcc cagaaggacc tctcaattcc   1500
tctgtccatc aagactagca gcgggggctgg gagtccggct gtggcagtgc ccacacactc   1560
gcagccctca cccaccccca gcaatgagag tacagacacg gcctctgaga tcggcagtgc   1620
tttcaactcg ccactgcgct cgcctatccg ctcagccaac ccgacgcggc cctcagccc   1680
tgtcacctcc cacatctcca aggtgctttt tggagaggat gacagcctgc tgcgtgttga   1740
```

```
ctgcatacgc tacaaccgtg ctgtccgtga tctgggtcct gtcatcagca caggcctgct    1800
gcacctggct gaggatgggg tgctgagtcc cctggcgctg acagagggtg ggaagggttc    1860
ctcgccctcc atcagaccaa tccaaggcag ccaggggtcc agcagcccag tggagaagga    1920
ggtcgtggaa gccacggaca gcagagagaa gacggggatg gtgaggcctg cgagcccctt    1980
gagtggggag aaatactcac ccaaggagct gctggcactg ctgaagtgtg tggaggctga    2040
gattgcaaac tatgaggcgt gcctcaagga ggagtagag aagaggaaga agttcaagat    2100
tgatgaccag agaaggaccc acaactacga tgagttcatc tgcaccttta tctccatgct    2160
ggctcaggaa ggcatgctgg ccaacctagt ggagcagaac atctccgtgc ggcggcgcca    2220
aggggtcagc atcggccggc tccacaagca gcggaagcct gaccggcgga aacgctctcg    2280
cccctacaag gccaagcgcc agtgaggact gctggccctg actctgcagc ccactcttgc    2340
cgtgtggccc tcaccagggt ccttccctgc cccacttccc cttttcccag tattactgaa    2400
tagtcccagc tggagagtcc aggccctggg aatgggagga accaggccac attccttcca    2460
tcgtgccctg aggcctgaca cggcagatca gccccatagt gctcaggagg cagcatctgg    2520
agttggggca cagcgaggta ctgcagcttc ctccacagcc ggctgtggag cagcaggacc    2580
tggcccttct gcctgggcag cagaatatat attttaccta tcagagacat ctatttttct    2640
gggctccaac ccaacatgcc accatgttga cataagttcc tacctgacta tgctttctct    2700
cctaggagct gtcctggtgg gcccaggtcc ttgtatcatg ccacggtccc aactacaggg    2760
tcctagctgg gggcctgggt gggccctggg ctctgggccc tgctgctcta gccccagcca    2820
ccagcctgtc cctgttgtaa ggaagccagg tcttctctct tcattcctct taggagagtg    2880
ccaaactcag ggacccagca ctgggctggg ttgggagtag ggtgtcccag tggggttggg    2940
gtgagcaggc tgctgggatc ccatggcctg agcagagcat gtgggaactg ttcagtggcc    3000
tgtgaactgt cttccttgtt ctagccaggc tgttcaagac tgctctccat agcaaggttc    3060
tagggctctt cgccttcagt gttgtggccc tagctatggg cctaaattgg gctctaggtc    3120
tctgtccctg gcgcttgagg ctcagaagag cctctgtcca gcccctcagt attaccatgt    3180
ctccctctca ggggtagcag agacaggggtt gcttatagga agctggcacc actcagctct    3240
tcctgctact ccagtttcct cagcctctgc aaggcactca gggtgggggga cagcaggatc    3300 aagacaaccc gttggagccc ctgtgttcca gaggacctga tgccaagggg taatgggccc    3360
agcagtgcct ctggagccca ggccccaaca cagccccatg gcctctgcca gatggctttg    3420
aaaaaggtga tccaagcagg ccccctttatc tgtacatagt gactgagtgg ggggtgctgg    3480
caagtgtggc agctgcctct gggctgagca cagcttgacc cctctagccc ctgtaaatac    3540
tggatcaatg aatgaataaa actctcctaa gaatctcctg agaaaaaaaa aaaaaaaaa    3599
```

<210> SEQ ID NO 3
<211> LENGTH: 9983
<212> TYPE: DNA
<213> ORGANISM: Homo sapiens

<400> SEQUENCE: 3

```
ccgttcgccg ccccgccccg tccctcctct cccaccatcc gcgcccagcc ccgcccatcc      60
ccgccttttc ccctagcctg ccccgcccct cctctcgccc cacctgcgcc cagcacttcc     120
cggccccgcc ttttcccctc gccgctccg ccccctccct cgcagcaccc gggcctagta     180
ctgcccgtcc cgcccctcct ctcgagcctc agcgctcagc atcgcccgga ccccctcttc     240
ccttcgcccg cctcgtcccg accctcccct tcgcccccgt cccgccccgc ccctcccctt     300
```

```
cgcccccgtc  ccgtcccgcc  ccgcccctcc  ccttcgcccc  cgtccctccc  cttcgccccc   360
gtccctccgc  gcgtgcgcgt  tcgccttcga  gcgcatgccc  gcatctgctg  tccgacaggc   420
ggaagacgag  cccagaggcg  gagcagggcc  gtcgcgcctt  ggtgacgtct  gccgccggcg   480
cgggcgggtg  acgcgactgg  gcccgttgtc  tgtgtgtggg  actgaggggc  ccggggggcg   540 gtggggggctc ccggtggggg  cagcggtggg  gagggagggc  ctggacatgg  cgctgagggg   600
ccgccccgcg  ggaagatgaa  taagggctgg  ctggagctgg  agagcgaccc  aggtgaggag   660
gggaccggga  gggccagggg  ctggggaggc  cggatgggcc  cgggacgcgc  ctgcctgacc   720
atcaccccct  cctcttgtcg  ccccacccag  gcctcttcac  cctgctcgtg  gaagatttcg   780
gtaagagcct  tttctccctg  ccggaccggg  gctgtggcgg  cccacccctg  cgccctcact   840 catcagggc   tgtccttccc  tactgctttc  ctttcctcat  cgcaggtgtc  aagggggtgc   900
aagtggagga  gatctacgac  cttcagagca  aatgtcaggg  gtgagtggct  gtacaccagg   960 gctgccccctt acacccagag  tgctggggaa  ggtcccagag  aacagggccc  cttagggaag   1020
acagtgccag  gaaccctacg  ttgtaaaatc  tcacagaaag  cagcagcctt  gctctctgag   1080
tgcccgctcc  tgatcaaact  gatactttct  tttctcccaa  actttcctta  gcgcttccct   1140
ttttgtagca  gccccctccc  cacccctaag  catcctttgg  ttcagctgct  ttcctggcct   1200
tgcagcggga  agacccccggt cacacaatgt  cttttgtgca  gttgtgtaat  gtattaattt   1260
tagtgtgccc  atgtgtcctt  ggctttaatc  ctgacacaaa  gtcatcctgt  attgattggt   1320
tggggtgaca  aggcccctcc  tgggtgccca  cacttagagt  cttttcccag  tggtcctgca   1380
gaatagatgt  gtaagagagt  agcaacagta  gcaaccgtga  ctgaaccaag  aagtctactt   1440
taatttcctg  gaacaaaaga  gactggtgtg  ggtgttcatt  tgctttcctg  actgcattgg   1500
ggcccacaag  tgagaaggag  tgcctcagtt  cctcatcaga  gttttgttc   ttgtcttact   1560 ttgtgttcct  accctgtccc  atccttggcc  ctcagttcca  gctttctttc  tcttacccag   1620
aactatagac  ttcataagga  gactgggtgg  actcctggag  catcacagtc  agaggcttat   1680
gctttgctct  gcctgtggca  ggcctttggt  gtgtgagggc  acaaggccac  ttcagacaca   1740
gtgttgggaa  gaagccaggg  gagagggggg  atcacagcaa  ggacacctga  gtgatgacgc   1800
agtgcaaagg  attaatggga  gaaagaaggg  aatgctgatt  gtcttctccc  ctttggctga   1860
tctggctctg  ccccttactt  cccccagccc  tgtatatgga  tttatcttcc  tgttcaaatg   1920
gatcgaagag  cgccggtccc  ggcgaaaggt  ctctaccttg  gtggatgata  cgtccgtgat   1980
tgatgatgat  attgtgaata  acatgttctt  gcccaccag   gtctgctgga  ctctgtgctt   2040
tgtttggagg  gtgggatgct  gccatgtttt  tgcttgggaa  gtggaaatgg  aggaagacag   2100
gaggaggaga  taggcagatt  ctaggggtgg  tagctacaga  aatcctctgg  cagaacgaac   2160
tgaactctta  attcattaaa  gggaacagct  ttagagtagg  agggtgtctg  agtccactct   2220
ctgtgtcctc  agatatccag  tgggtatttg  gtaggtgctt  gttaaatgaa  taaacattag   2280
gcaaagatga  aaggagctga  aaggggagt   tgtccagata  tgactgacct  gctctggatc   2340
cccattcttg  atgtatatgg  gcttgggggct tgcagtgagg  ggtgctgtgt  atgggtgact   2400
attcttggtt  tcacagctga  tacccaactc  ttgtgcaact  catgccttgc  tgagcgtgct   2460
cctgaactgc  agcagcgtgg  acctgggacc  cacccctgagt cgcatgaagg  acttcaccaa   2520
gggtttcagc  cctgaggtag  gctgcagtgc  cttcatcctg  gctcacagcc  aactgggcag   2580
atctgaccct  gagggccact  gggaatgcta  ccacatgata  ttgggtacta  ttaggctgtt   2640
```

```
tcttttttcaa atgattgttt atgttacatt tgactcttaa ataaattgtg taaggccatt    2700
gtttttagat gcagttgcgg ggaaaggaca caggcctagg gagggaggag agtttcctta    2760
agtcagacca tgtcagaacc ttctctgtca ggacttttcc tctcaggcca tgttgcttcc    2820
tagtgtccac taattaccat gcaaggccag cacagtccat ctctttgggg ctccagagct    2880
cttttctgcc cccaccagcc ttttaagaaa gttcgtctgt gttccttccg attcctggaa    2940
tgcctccagg ctgctctctg aagctttgcc ttccacccat agtcctacct gaggagaaat    3000
tattctgata cggccttatt ttcttccccg tagagcaaag gatatgcgat tggcaatgcc    3060
ccggagttgg ccaaggccca taatagccat gccaggtgtg tgggagctgt gggagctgat    3120
gtggggtggg agtaggggga gtatcatttt ttgggccctg actctgtttt tccccaggcc    3180
cgagccacgc cacctccctg agaagcagaa tggccttagt gcagtgcgga ccatggaggc    3240
gttccacttt gtcagctatg tgcctatcac aggccggctc tttgagctgg atgggctgaa    3300
ggtctacccc attgaccatg gtaggcacca tgagctggag gcctgttggg tgtctctgcc    3360
tacctcctag ggagctgggg ctcagggccc tctggtatgt ggtacccagt ggcagggdtt    3420
gtcggtaccg acacccggct ctggctgggg tttcacccta caccatattg cccgaccagc    3480
tcctgattcc ctggctcaac tgctcttctc tgtcttcctt cccactcctg gcctgcccaa    3540
actcagggtt tccttctcgc tgattccttg tcttggtctc cactagggcc ctgggggag    3600 gacgaggagt ggacagacaa ggcccggcgg gtcatcatgg agcgtatcgg cctcgccact    3660
gcagggtaag ggccctgtgc ctgccctgtt ctactctctg gagctgtacc tactttggga    3720
gggacagaga gtatccaggt gatttgtaaa ttgcaaggcc atatggtgaa tctggcaaga    3780
tcaggcttag atcatgggtt ctcaacttgt tgtcttattt cctgcctggg ctgcctgtgg    3840
cctgctcctg ggtgggctgg gggaggggca ggcctcagtg gagccttagg cagcccaggt    3900
ctgctggttc acttccagat aggcccctca tacagcttgt tggaaggtac cagctcaggt    3960
gcctggcatg tatggctagt cgctgcctgc ctgttgggt ggggcctata cctacagctg    4020
caggtgtgac tgcagggagc cctgccagga tatctgcctc aacctgatgg cggggccggg    4080
gcgggagctg ctctcacggc tgcggctgtg actgcaggga gccctaccac gacatccgct    4140
tcaacctgat ggcagtggtg cccgaccgca ggatcaagta tgaggccagg ctgcatgtgc    4200
tgaaggtgaa ccgtcagaca gtactagagg ctctgcagca ggtaggtgcc ctttcttcct    4260
ggcctctgcc cagcccaacc ctccctgcat tcctcctccc ttcccccaca gcatttgtct    4320
ctgattcgtg aacatactct cttgtagatc tgggcttcag ctaaccacat cttttctttg    4380
cccccattgt gggaaggtg ggacttggag tggggaggga gaatagcttc taaaaggaag    4440
tttgggtttg ggtgttttat ttccctgtga gtgaatgggt agagccaagg ccattattcc    4500
tttaggtcct cagcccttag ctatttaagg tagaagcccg ggtctaccct ttctcctctg    4560
agccctggat tctgttgtta gctgataaga gtaacacagc cagagctgat tcagacccac    4620
aagtctcaag agtcacagct gcctgaggag tccaagtcag ccagcaacaa gtccccgctg    4680
gtgctggaag caaacagggc ccctgcagcc tctgagggca accacacagg tactgggggg    4740
tttgggacct cttgtggacc tcagagccac ccgctaatgt ctgacatggg aggcctaaac    4800
agggaaagtc tttttctggg gatgtccttg ggcagtgttc ttccccgtc agaaggtaga    4860 gggagagcag tccttcccta aagaaaggca cctgtaaagg gccgctgtta ccacaggccc    4920 ctgggcccctt ctctgtaatg tacactccct ttccttgtttt tctagaggc ggttttttt    4980 tttttttttt tttttttttt tcttcctgct tctttttttcc catctcattc tttgccctgt    5040
```

```
ctcattgcgg gatcatgact tagagcttgc tgactcccat tgcaccagct ggctgggctg    5100
ttcttctctg ggaagtgctg gttcacaggg ccggggagac tgtgagcttt tcttggagat    5160
cctactggag gtcctgcctg tgttcttgcc ctgtctcaga tggtgcagag gaggcggctg    5220
gttcatgcgc acaagcccca tcccacagcc ctcccaacaa acccaagcta gtggtgaagc    5280
ctccaggcag cagcctcaat ggggttcacc ccaaccccac tcccattgtc cagcggctgc    5340
cggcctttct agacaatcac aattatgcca agtcccccat gcaggtaagc tgggagcacc    5400
cttgcaggat tctctacttg attctcttga gaggctgcaa caggcaattt tcccatgtgg    5460
ttccttggtg ttcatccttg gcatggctgg gtcaagctgc ctgggcctgg gttgctaggt    5520
tcctctgcct gatatgaaaa ggcccccaca acagcaggag cttagggagg cagggagagc    5580
tcctttgaat ttaatctagt tacgtggctg tgggattaaa tgtttaggtc acgtccttg    5640 gtacaacttc atgggttggg ttttactggc aaaataaagg catgtgtttc agggcactct    5700
gtttctctta aaacccctcc gtggggttct atccagtgta agtgggtggc agcctcccca    5760
caagccaagg acaggccatg gaacagctgg aggggttccg ctgactcagt ctggaaaacc    5820
atgttggctt tctctctggc tgtgagtgtc taggctcagc ctgggccgag cagcacttgt    5880
ttgtaactgc cctggtcttt gtcccaggag gaagaagacc tggcggcagg tgtgggccgc    5940
agccgagttc cagtccgccc accccagcag tactcagatg atgaggatga ctatgaggat    6000
gacgaggagg atgacgtgca gaacaccaac tctgccctta ggtcagccca gctttctaag    6060
gctaccaggt tctaggtgct tcggatccca tcctgaatat ctcagtctgt gtctgagaat    6120
gccctgcagc agataatgtt gagcacctgc ggagtttggg gccctggggg aggctggcat    6180 gatgggctg accccaggtc cccaggaagt ttttggtggg ctgggggta aggctgagca    6240 cgtaagctta tatcatgtcc tattggaagt ggccttttag ccaggccttg aaggattggt    6300 tgggcaggg atggaggaga tgtggtggt ggggaggcag cttttgctgga acacagggca    6360 ttggcaaaag gccaggagtg ggatggctgg aatagaggaa gtgtcttttg aggacacttg    6420
gctgcagctg tcagaacttg atgccaggct tagcatggct agttcaagtt gcttggacca    6480
agtataagga gttttagggt cagcccctgg aggtcgggat gtatttaagc cattctgggt    6540
actgctgggt atggtcacct ggcccgttcc cttgcttcac atcttctcgg gccccacagg    6600
tataagggga agggaacagg gaagccaggg gcattgagcg gttctgctga tgggcaactg    6660
tcagtgctgc agcccaacac catcaacgtc ttggctgaga agctcaaaga gtcccagaag    6720
gacctctcaa ttcctctgtc catcaagact agcagcgggg ctgggagtcc ggctgtggca    6780
gtgcccacac actcgcagcc ctcacccacc cccagcaatg agagtacaga cacggcctct    6840
gagatcggca gtgctttcaa ctcgccactg cgctcgccta tccgctcagc caacccgacg    6900
cggccctcca gccctgtcac ctcccacatc tccaaggtgc ttttggaga ggatgacagc    6960 ctgctgcgtg ttgactgcat acgctacaac cgtgctgtcc gtgatctggg tcctgtcatc    7020
agcacaggcc tgctgcacct ggctgaggat ggggtgctga gtccctggc gctgacaggt    7080 gggccttgga ctggctcact ggccacttgg tgcacccagg agggaggagg gaagtggcca    7140
agtgaccaca aagtgtcctg cactctgatg attttcttgt gacctctctt cccagagggt    7200
gggaagggtt cctcgccctc catcagacca atccaaggca gccaggggtc cagcagccca    7260
gtggagaagg aggtcgtgga agccacggac agcagagaga agacgggat ggtgaggcct    7320 ggcgagccct tgagtgggga gaaatactca cccaaggtga gcctccgttg tggttttctc    7380
```

-continued

```
ctttaatcct ggcagagggt aaggcctgag ctcctcctgc ccaggtgcca agttcttgat    7440
tggaactttg gtgtgaagat tggtggctgg agccatgtgc cagaagactt tctgggttgg    7500
gtggtggcag gggccttgat aggcatggac tcgctgctca tccttgcctc tagctgccta    7560
ttgctcgtgg ggctttgttg ctggcccgcc ccgatcagag gtgcaatgct gggttttggc    7620
aggagctgct ggcactgctg aagtgtgtgg aggctgagat tgcaaactat gaggcgtgcc    7680
tcaaggagga ggtagagaag aggaagaagt tcaaggtggg tgatttctcc agttgcctga    7740
tctggcctct cccgaggtcc actggtggct gctctggcaa gattggctcc agtgctctca    7800
gtcttcttct ctcctacaga ttgatgacca gagaaggacc cacaactacg atgagttcat    7860
ctgcaccttt atctccatgc tggctcagga aggtgagggg atgcgctgct gtcttaactg    7920
gaatgccctg ctgagggccg tgtccttcag ctcccctccc ctggcctctc ctgaggcttg    7980
agcagacctt ggggcacagg gagggccatg agagcctcag ctcctggcct gaggcagcca    8040
gcacctgctc aagggtctct acctcttcgc aggcatgctg gccaacctag tggagcagaa    8100
catctccgtg cggcggcgcc aagggtcag catcggccgg ctccacaagc agcggaagcc    8160
tgaccggcgg aaacgctctc gccctacaa ggccaagcgc cagtgaggac tgctggccct    8220
gactctgcag cccactcttg ccgtgtgcc ctcaccaggg tccttccctg ccccacttcc    8280
ccttttccca gtattactga atagtcccag ctggagagtc caggccctgg gaatgggagg    8340
aaccaggcca cattccttcc atcgtgccct gaggcctgac acggcagatc agccccatag    8400
tgctcaggag gcagcatctg gagttggggc acagcgaggt actgcagctt cctccacagc    8460
cggctgtgga gcagcaggac ctggcccttc tgcctgggca gcagaatata tattttacct    8520
atcagagaca tctattttc tgggctccaa cccaacatgc caccatgttg acataagttc    8580
ctacctgact atgctttctc tcctaggagc tgtcctggtg ggcccaggtc cttgtatcat    8640
gccacggtcc caactacagg gtcctagctg ggggcctggg tgggccctgg gctctgggcc    8700
ctgctgctct agccccagcc accagccgt ccctgttgta aggaagccag gtcttctctc    8760
ttcattcctc ttaggagagt gccaaactca gggacccagc actgggctgg gttgggagta    8820
gggtgtccca gtggggttgg ggtgagcagg ctgctgggat cccatggcct gagcagagca    8880
tgtgggaact gttcagtggc ctgtgaactg tcttccttgt tctagccagg ctgttcaaga    8940
ctgctctcca tagcaaggtt ctagggctct tcgccttcag tgttgtggcc ctagctatgg    9000
gcctaaattg ggctctaggt ctctgtccct ggcgcttgag gctcagaaga gcctctgtcc    9060
agccctcag tattaccatg tctccctctc aggggtagca gagacaggt tgcttatagg    9120
aagctggcac cactcagctc ttcctgctac tccagtttcc tcagcctctg caaggcactc    9180
agggtggggg acagcaggat caagacaacc cgttggagcc cctgtgttcc agaggacctg    9240
atgccaaggg gtaatgggcc cagcagtgcc tctggagccc aggccccaac acagcccat    9300
ggcctctgcc agatggcttt gaaaaaggtg atccaagcag gccccttat ctgtacatag    9360
tgactgagtg gggggtgctg gcaagtgtgg cagctgcctc tgggctgagc acagcttgac    9420
ccctctagcc cctgtaaata ctggatcaat gaatgaataa aactctccta agaatctcct    9480
gagaaatgaa ccctcctgtg gttgctggcc tgagatatgg aggctgggcc ttactagacc    9540
tcatgggcct agggccctgg gaccagaaag gtaagaagta tatgatcctt gagtgtccag    9600
ctgtcttggg ccagagatcc ttggaatcct aggcctggga tttaggacct gagctgagga    9660
gggacttcag gtggactgta gacagggtgc actttctggg gagagggcca tggctttcac    9720
caaatctgtg gctttgcagc ctggagaggt gctgggactg tgggtcaaag aggcggggct    9780
```

```
gcctctaatc taatctcgcc tggtgtgttc tccctgggag ggcgctgggc atctcttcct    9840
tgttgctttt ggacaggtaa agcaggtcaa agctgccgcc tctgtcccgc tctcctctgc    9900
cgactgcatc gtctgctgag gctgctgcag cccctcacca gcccctggc agtgagtcct     9960 gcagaggggt cctcatgcaa gca                                             9983
```

<210> SEQ ID NO 4
<211> LENGTH: 49
<212> TYPE: DNA
<213> ORGANISM: Homo sapiens

<400> SEQUENCE: 4

```
tccccgtaga gcaaaggata tgcgattggc aatgccccgg agttggcaa                  49
```

<210> SEQ ID NO 5
<211> LENGTH: 11
<212> TYPE: DNA
<213> ORGANISM: Homo sapiens

<400> SEQUENCE: 5

```
ccccatccca c                                                          11
```

<210> SEQ ID NO 6
<211> LENGTH: 23
<212> TYPE: DNA
<213> ORGANISM: Homo sapiens

<400> SEQUENCE: 6

```
tgaccatggt aggcaccatg agc                                             23
```

<210> SEQ ID NO 7
<211> LENGTH: 15
<212> TYPE: DNA
<213> ORGANISM: Homo sapiens

<400> SEQUENCE: 7

```
cgggtcatca tggag                                                      15
```

<210> SEQ ID NO 8
<211> LENGTH: 35
<212> TYPE: DNA
<213> ORGANISM: Homo sapiens

<400> SEQUENCE: 8

```
cccctcctct tgtcgcccca cccaggcctc ttcac                                35
```

<210> SEQ ID NO 9
<211> LENGTH: 12
<212> TYPE: DNA
<213> ORGANISM: Homo sapiens

<400> SEQUENCE: 9

```
gagctgctgg ca                                                         12
```

<210> SEQ ID NO 10
<211> LENGTH: 25
<212> TYPE: DNA
<213> ORGANISM: Homo sapiens

<400> SEQUENCE: 10

```
ggaggcgttc cactttgtca gctat                                           25
```

```
<210> SEQ ID NO 11
<211> LENGTH: 38
<212> TYPE: DNA
<213> ORGANISM: Homo sapiens

<400> SEQUENCE: 11
atcttccacg agcagggtga agaggcctgg gtggggcg                              38

<210> SEQ ID NO 12
<211> LENGTH: 27
<212> TYPE: DNA
<213> ORGANISM: Homo sapiens

<400> SEQUENCE: 12
cagaaccatc tccgtgcggc ggcgcca                                         27

<210> SEQ ID NO 13
<211> LENGTH: 39
<212> TYPE: DNA
<213> ORGANISM: Homo sapiens

<400> SEQUENCE: 13
attcatcttc ccgcggggcg gccnctcagc gccatgtcc                            39

<210> SEQ ID NO 14
<211> LENGTH: 21
<212> TYPE: DNA
<213> ORGANISM: Homo sapiens

<400> SEQUENCE: 14
ggtatcagct gtgaaaccaa g                                               21

<210> SEQ ID NO 15
<211> LENGTH: 20
<212> TYPE: DNA
<213> ORGANISM: Homo sapiens

<400> SEQUENCE: 15
aggctgctgc tttctgtgag                                                 20

<210> SEQ ID NO 16
<211> LENGTH: 19
<212> TYPE: DNA
<213> ORGANISM: Homo sapiens

<400> SEQUENCE: 16
cgttgtctgt gtgtgggac                                                  19

<210> SEQ ID NO 17
<211> LENGTH: 20
<212> TYPE: DNA
<213> ORGANISM: Homo sapiens

<400> SEQUENCE: 17
atgctgattg tcttctcccc                                                 20

<210> SEQ ID NO 18
<211> LENGTH: 20
<212> TYPE: DNA
<213> ORGANISM: Homo sapiens

<400> SEQUENCE: 18
ctccatttcc acttcccaag                                                 20
```

<210> SEQ ID NO 19
<211> LENGTH: 18
<212> TYPE: DNA
<213> ORGANISM: Homo sapiens

<400> SEQUENCE: 19
cttggggctt gcagtgag                                                 18

<210> SEQ ID NO 20
<211> LENGTH: 20
<212> TYPE: DNA
<213> ORGANISM: Homo sapiens

<400> SEQUENCE: 20
atgtggtagc attcccagtg                                               20

<210> SEQ ID NO 21
<211> LENGTH: 21
<212> TYPE: DNA
<213> ORGANISM: Homo sapiens

<400> SEQUENCE: 21
ggccttgcaa tttacaaatc a                                             21

<210> SEQ ID NO 22
<211> LENGTH: 20
<212> TYPE: DNA
<213> ORGANISM: Homo sapiens

<400> SEQUENCE: 22
tgtcttcctt cccactcctg                                               20

<210> SEQ ID NO 23
<211> LENGTH: 22
<212> TYPE: DNA
<213> ORGANISM: Homo sapiens

<400> SEQUENCE: 23
ggatatctgc ctcaacctga tg                                            22

<210> SEQ ID NO 24
<211> LENGTH: 19
<212> TYPE: DNA
<213> ORGANISM: Homo sapiens

<400> SEQUENCE: 24
gaagggagga ggaatgcag                                                19

<210> SEQ ID NO 25
<211> LENGTH: 20
<212> TYPE: DNA
<213> ORGANISM: Homo sapiens

<400> SEQUENCE: 25
ttcctttagg tcctcagccc                                               20

<210> SEQ ID NO 26
<211> LENGTH: 20
<212> TYPE: DNA
<213> ORGANISM: Homo sapiens

<400> SEQUENCE: 26

```
ctgaggtcca caagaggtcc                                              20

<210> SEQ ID NO 27
<211> LENGTH: 18
<212> TYPE: DNA
<213> ORGANISM: Homo sapiens

<400> SEQUENCE: 27
cagacattag cgggtggc                                                18

<210> SEQ ID NO 28
<211> LENGTH: 19
<212> TYPE: DNA
<213> ORGANISM: Homo sapiens

<400> SEQUENCE: 28
aagggtgctc ccagcttac                                               19

<210> SEQ ID NO 29
<211> LENGTH: 20
<212> TYPE: DNA
<213> ORGANISM: Homo sapiens

<400> SEQUENCE: 29
cctgtgttct tgccctgtct                                              20

<210> SEQ ID NO 30
<211> LENGTH: 21
<212> TYPE: DNA
<213> ORGANISM: Homo sapiens

<400> SEQUENCE: 30
gctgtgagtg tctaggctca g                                            21

<210> SEQ ID NO 31
<211> LENGTH: 22
<212> TYPE: DNA
<213> ORGANISM: Homo sapiens

<400> SEQUENCE: 31
agactgagat attcaggatg gg                                           22

<210> SEQ ID NO 32
<211> LENGTH: 21
<212> TYPE: DNA
<213> ORGANISM: Homo sapiens

<400> SEQUENCE: 32
ccaagtgacc acaaagtgtc c                                            21

<210> SEQ ID NO 33
<211> LENGTH: 20
<212> TYPE: DNA
<213> ORGANISM: Homo sapiens

<400> SEQUENCE: 33
agctcaggcc ttaccctctg                                              20

<210> SEQ ID NO 34
<211> LENGTH: 20
<212> TYPE: DNA
<213> ORGANISM: Homo sapiens

<400> SEQUENCE: 34
```

```
ctgagcacta tggggctgat                                              20

<210> SEQ ID NO 35
<211> LENGTH: 20
<212> TYPE: DNA
<213> ORGANISM: Homo sapiens

<400> SEQUENCE: 35
tcttaactgg aatgccctgc                                              20

<210> SEQ ID NO 36
<211> LENGTH: 20
<212> TYPE: DNA
<213> ORGANISM: Homo sapiens

<400> SEQUENCE: 36
ctgccttgga ttggtctgat                                              20

<210> SEQ ID NO 37
<211> LENGTH: 20
<212> TYPE: DNA
<213> ORGANISM: Homo sapiens

<400> SEQUENCE: 37
caacaccatc aacgtcttgg                                              20

<210> SEQ ID NO 38
<211> LENGTH: 20
<212> TYPE: DNA
<213> ORGANISM: Homo sapiens

<400> SEQUENCE: 38
tgatgacagg acccagatca                                              20

<210> SEQ ID NO 39
<211> LENGTH: 20
<212> TYPE: DNA
<213> ORGANISM: Homo sapiens

<400> SEQUENCE: 39
gctgtcagaa cttgatgcca                                              20

<210> SEQ ID NO 40
<211> LENGTH: 20
<212> TYPE: DNA
<213> ORGANISM: Homo sapiens

<400> SEQUENCE: 40
ctagctgcct attgctcgtg                                              20

<210> SEQ ID NO 41
<211> LENGTH: 19
<212> TYPE: DNA
<213> ORGANISM: Homo sapiens

<400> SEQUENCE: 41 gagggagct gaaggacac                                                19

<210> SEQ ID NO 42
<211> LENGTH: 20
<212> TYPE: DNA
<213> ORGANISM: Homo sapiens
```

```
<400> SEQUENCE: 42
tttgccttcc acccatagtc                                          20

<210> SEQ ID NO 43
<211> LENGTH: 19
<212> TYPE: DNA
<213> ORGANISM: Homo sapiens

<400> SEQUENCE: 43
agctccctag gaggtaggc                                           19

<210> SEQ ID NO 44
<211> LENGTH: 12
<212> TYPE: DNA
<213> ORGANISM: Homo sapiens

<400> SEQUENCE: 44
gggctgtggg at                                                  12

<210> SEQ ID NO 45
<211> LENGTH: 12
<212> TYPE: DNA
<213> ORGANISM: Homo sapiens

<400> SEQUENCE: 45
gggctcttgt gc                                                  12

<210> SEQ ID NO 46
<211> LENGTH: 14
<212> TYPE: DNA
<213> ORGANISM: Homo sapiens

<400> SEQUENCE: 46
gggccctggg ggga                                                14

<210> SEQ ID NO 47
<211> LENGTH: 14
<212> TYPE: DNA
<213> ORGANISM: Homo sapiens

<400> SEQUENCE: 47
gggccctgag ggga                                                14

<210> SEQ ID NO 48
<211> LENGTH: 170
<212> TYPE: PRT
<213> ORGANISM: Homo sapiens

<400> SEQUENCE: 48
```

Leu Ile Pro Asn Ser Cys Ala Thr His Ala Leu Leu Ser Val Leu Leu
 1               5                  10                  15

Asn Cys Ser Ser Val Asp Leu Gly Pro Thr Leu Ser Arg Met Lys Asp
             20                  25                  30

Phe Thr Lys Gly Phe Ser Pro Glu Ser Lys Gly Tyr Ala Ile Gly Asn
         35                  40                  45

Ala Pro Glu Leu Ala Lys Ala His Asn Ser His Ala Arg Pro Glu Pro
     50                  55                  60

Arg His Leu Pro Glu Lys Gln Asn Gly Leu Ser Ala Val Arg Thr Met
 65                  70                  75                  80

Glu Ala Phe His Phe Val Ser Tyr Val Pro Ile Thr Gly Arg Leu Phe
                 85                  90                  95

Glu Leu Asp Gly Leu Lys Val Tyr Pro Ile Asp His Gly Gln Glu Ser
            100                 105                 110

Gln Leu Pro Glu Glu Ser Lys Ser Ala Ser Asn Lys Ser Pro Leu Val
        115                 120                 125

Leu Gly Glu Lys Tyr Ser Pro Lys Glu Leu Leu Ala Leu Leu Lys Cys
    130                 135                 140

Val Glu Ala Glu Ile Ala Ile Asp Asp Gln Arg Arg Thr His Asn Tyr
145                 150                 155                 160

Asp Glu Phe Ile Cys Thr Phe Ile Ser Met
                165                 170

<210> SEQ ID NO 49
<211> LENGTH: 170
<212> TYPE: PRT
<213> ORGANISM: Pan troglodytes

<400> SEQUENCE: 49

Leu Ile Pro Asn Ser Cys Ala Thr His Ala Leu Leu Ser Val Leu Leu
1               5                   10                  15

Asn Cys Ser Asn Val Asp Leu Gly Pro Thr Leu Ser Arg Met Lys Asp
            20                  25                  30

Phe Thr Lys Gly Phe Ser Pro Glu Ser Lys Gly Tyr Ala Ile Gly Asn
        35                  40                  45

Ala Pro Glu Leu Ala Lys Ala His Asn Ser His Ala Arg Pro Glu Pro
    50                  55                  60

Arg His Leu Pro Glu Lys Gln Asn Gly Leu Ser Ala Val Arg Thr Met
65                  70                  75                  80

Glu Ala Phe His Phe Val Ser Tyr Val Pro Ile Thr Gly Arg Leu Phe
                85                  90                  95

Glu Leu Asp Gly Leu Lys Val Tyr Pro Ile Asp His Gly Gln Glu Ser
            100                 105                 110

Gln Leu Pro Glu Glu Ser Lys Ser Ala Ser Asn Lys Ser Pro Leu Val
        115                 120                 125

Leu Gly Glu Lys Tyr Ser Pro Lys Glu Leu Leu Ala Leu Leu Lys Cys
    130                 135                 140

Val Glu Ala Glu Ile Ala Ile Asp Asp Gln Arg Arg Thr His Asn Tyr
145                 150                 155                 160

Asp Glu Phe Ile Cys Thr Phe Ile Ser Met
                165                 170

<210> SEQ ID NO 50
<211> LENGTH: 170
<212> TYPE: PRT
<213> ORGANISM: Macaca mulatta

<400> SEQUENCE: 50

Leu Ile Pro Asn Ser Cys Ala Thr His Ala Leu Leu Ser Val Leu Leu
1               5                   10                  15

Asn Cys Ser Asn Val Asp Leu Gly Pro Thr Leu Ser Arg Met Lys Asp
            20                  25                  30

Phe Thr Lys Gly Phe Ser Pro Glu Ser Lys Gly Tyr Ala Ile Gly Asn
        35                  40                  45

Ala Pro Glu Leu Ala Lys Ala His Asn Ser His Ala Arg Pro Glu Pro
    50                  55                  60

Arg His Leu Pro Glu Lys Gln Asn Gly Leu Ser Ala Val Arg Thr Met
65                  70                  75                  80

```
Glu Ala Phe His Phe Val Ser Tyr Val Pro Ile Thr Gly Arg Leu Phe
                85                  90                  95

Glu Leu Asp Gly Leu Lys Val Tyr Pro Ile Asp His Gly Gln Glu Ser
            100                 105                 110

Gln Leu Pro Glu Glu Ser Lys Ser Ala Ser Asn Lys Ser Pro Leu Val
        115                 120                 125

Leu Gly Glu Lys Tyr Ser Pro Lys Glu Leu Leu Ala Leu Leu Lys Cys
    130                 135                 140

Val Glu Ala Glu Ile Ala Ile Asp Asp Gln Arg Arg Thr His Asn Tyr
145                 150                 155                 160

Asp Glu Phe Ile Cys Thr Phe Ile Ser Met
                165                 170

<210> SEQ ID NO 51
<211> LENGTH: 170
<212> TYPE: PRT
<213> ORGANISM: Mus musculus

<400> SEQUENCE: 51

Leu Ile Pro Asn Ser Cys Ala Thr His Ala Leu Leu Ser Val Leu Leu
1               5                   10                  15

Asn Cys Ser Asn Val Asp Leu Gly Pro Thr Leu Ser Arg Met Lys Asp
            20                  25                  30

Phe Thr Lys Gly Phe Ser Pro Glu Ser Lys Gly Tyr Ala Ile Gly Asn
        35                  40                  45

Ala Pro Glu Leu Ala Lys Ala His Asn Ser His Ala Arg Pro Glu Pro
    50                  55                  60

Arg His Leu Pro Glu Lys Gln Asn Gly Leu Ser Ala Val Arg Thr Met
65                  70                  75                  80

Glu Ala Phe His Phe Val Ser Tyr Val Pro Ile Thr Gly Arg Leu Phe
                85                  90                  95

Glu Leu Asp Gly Leu Lys Val Tyr Pro Ile Asp His Gly Gln Glu Ser
            100                 105                 110

Gln Leu Pro Glu Glu Ser Lys Pro Ala Ser Ser Lys Ser Pro Leu Gly
        115                 120                 125

Leu Gly Glu Lys Tyr Ser Pro Lys Glu Leu Leu Ala Leu Leu Lys Cys
    130                 135                 140

Val Glu Ala Glu Ile Ala Ile Asp Asp Gln Arg Arg Thr His Asn Tyr
145                 150                 155                 160

Asp Glu Phe Ile Cys Thr Phe Ile Ser Met
                165                 170

<210> SEQ ID NO 52
<211> LENGTH: 170
<212> TYPE: PRT
<213> ORGANISM: Rattus norvegicus

<400> SEQUENCE: 52

Leu Ile Pro Asn Ser Cys Ala Thr His Ala Leu Leu Ser Val Leu Leu
1               5                   10                  15

Asn Cys Ser Asn Val Asp Leu Gly Pro Thr Leu Ser Arg Met Lys Asp
            20                  25                  30

Phe Thr Lys Gly Phe Ser Pro Glu Ser Lys Gly Tyr Ala Ile Gly Asn
        35                  40                  45

Ala Pro Glu Leu Ala Lys Ala His Asn Ser His Ala Arg Pro Glu Pro
    50                  55                  60
```

```
Arg His Leu Pro Glu Lys Gln Asn Gly Leu Ser Ala Val Arg Thr Met
 65                  70                  75                  80

Glu Ala Phe His Phe Val Ser Tyr Val Pro Ile Thr Gly Arg Leu Phe
                 85                  90                  95

Glu Leu Asp Gly Leu Lys Val Tyr Pro Ile Asp His Gly Gln Glu Ser
            100                 105                 110

Gln Leu Pro Glu Glu Ser Lys Pro Ala Ser Ser Lys Ser Pro Phe Gly
        115                 120                 125

Leu Gly Glu Lys Tyr Ser Pro Lys Glu Leu Leu Ala Leu Leu Lys Cys
    130                 135                 140

Val Glu Ala Glu Ile Ala Ile Asp Asp Gln Arg Arg Thr His Asn Tyr
145                 150                 155                 160

Asp Glu Phe Ile Cys Thr Phe Ile Ser Met
                165                 170

<210> SEQ ID NO 53
<211> LENGTH: 170
<212> TYPE: PRT
<213> ORGANISM: Bos taurus

<400> SEQUENCE: 53

Leu Ile Pro Asn Ser Cys Ala Thr His Ala Leu Leu Ser Val Leu Leu
  1               5                  10                  15

Asn Cys Ser Asn Val Asp Leu Gly Pro Thr Leu Ser Arg Met Lys Asp
                 20                  25                  30

Phe Thr Lys Gly Phe Ser Pro Glu Ser Lys Gly Tyr Ala Ile Gly Asn
             35                  40                  45

Ala Pro Glu Leu Ala Lys Ala His Asn Ser His Ala Arg Pro Glu Pro
         50                  55                  60

Arg His Leu Pro Glu Lys Gln Asn Gly Leu Ser Ala Val Arg Thr Met
 65                  70                  75                  80

Glu Ala Phe His Phe Val Ser Tyr Val Pro Ile Thr Gly Arg Leu Phe
                 85                  90                  95

Glu Leu Asp Gly Leu Lys Val Tyr Pro Ile Asp His Gly Gln Glu Ser
            100                 105                 110

Gln Leu Pro Glu Glu Ser Lys Pro Ala Ser Ser Lys Ser Pro Leu Ala
        115                 120                 125

Leu Gly Glu Lys Tyr Ser Pro Lys Glu Leu Leu Ala Leu Leu Lys Cys
    130                 135                 140

Val Glu Ala Glu Ile Ala Ile Asp Asp Gln Arg Arg Thr His Asn Tyr
145                 150                 155                 160

Asp Glu Phe Ile Cys Thr Phe Ile Ser Met
                165                 170

<210> SEQ ID NO 54
<211> LENGTH: 170
<212> TYPE: PRT
<213> ORGANISM: Didelphis virginiana

<400> SEQUENCE: 54

Leu Ile Pro Asn Ser Cys Ala Thr His Ala Leu Leu Ser Val Leu Leu
  1               5                  10                  15

Asn Cys Ser Asn Val Asp Leu Gly Pro Thr Leu Ser Arg Met Lys Asp
                 20                  25                  30

Phe Thr Lys Gly Phe Ser Pro Glu Ser Lys Gly Tyr Ala Ile Gly Asn
             35                  40                  45
```

```
Ala Pro Glu Leu Ala Lys Ala His Asn Ser His Ala Arg Pro Glu Pro
     50                  55                  60

Arg His Leu Pro Glu Lys Gln Asn Gly Ile Ser Ala Val Arg Thr Met
 65                  70                  75                  80

Glu Ala Phe His Phe Val Ser Tyr Val Pro Ile Lys Gly Arg Leu Phe
                 85                  90                  95

Glu Leu Asp Gly Leu Lys Val Tyr Pro Ile Asp His Gly Gln Glu Ser
                100                 105                 110

Gln Pro Pro Glu Asp Ser Lys Pro Ala Ser Cys Lys Pro Ser Leu Val
            115                 120                 125

Leu Gly Glu Lys Tyr Ser Pro Lys Glu Leu Leu Ala Leu Leu Lys Cys
        130                 135                 140

Val Glu Ala Glu Ile Ala Ile Asp Asp Gln Arg Arg Thr His Asn Tyr
145                 150                 155                 160

Asp Glu Phe Ile Cys Thr Phe Ile Ser Met
                165                 170

<210> SEQ ID NO 55
<211> LENGTH: 167
<212> TYPE: PRT
<213> ORGANISM: Gallus gallus

<400> SEQUENCE: 55

Leu Ile Pro Asn Ser Cys Ala Thr His Ala Leu Leu Ser Val Leu Leu
 1               5                  10                  15

Asn Cys Asn Asn Val Asp Leu Gly Pro Thr Leu Ser Arg Met Lys Asp
                 20                  25                  30

Phe Thr Lys Gly Phe Ser Pro Glu Ser Lys Gly Tyr Ala Ile Gly Asn
             35                  40                  45

Ala Pro Glu Leu Ala Lys Ala Arg Asn Ser His Ala Arg Pro Glu Pro
     50                  55                  60

Arg His Leu Pro Glu Lys Gln Asn Gly Ile Ser Ala Val Arg Thr Met
 65                  70                  75                  80

Glu Ala Phe His Phe Val Ser Tyr Val Pro Ile Lys Gly Arg Leu Phe
                 85                  90                  95

Glu Leu Asp Gly Leu Lys Val Tyr Pro Ile Asp His Gly Gln Glu Ser
                100                 105                 110

Gln Ser Pro Glu Glu Ala Lys Pro Ala Asn Ser Lys Thr Leu Gly Glu
            115                 120                 125

Lys Tyr Ser Pro Lys Glu Leu Leu Ala Leu Leu Lys Cys Val Glu Ala
        130                 135                 140

Glu Ile Ala Ile Asp Asp Gln Arg Arg Thr His Asn Tyr Asp Glu Phe
145                 150                 155                 160

Ile Cys Thr Phe Ile Ser Met
                165

<210> SEQ ID NO 56
<211> LENGTH: 166
<212> TYPE: PRT
<213> ORGANISM: Taeniopygia guttata

<400> SEQUENCE: 56

Leu Ile Pro Asn Ser Cys Ala Thr His Ala Leu Leu Ser Val Leu Leu
 1               5                  10                  15

Asn Cys Asn Asn Val Asp Leu Gly Pro Thr Leu Ser Arg Met Lys Asp
                 20                  25                  30
```

Phe Thr Lys Gly Phe Ser Pro Glu Ser Lys Gly Tyr Ala Ile Gly Asn
            35                  40                  45

Ala Pro Glu Leu Ala Lys Ala His Asn Ser His Ala Arg Pro Glu Pro
 50                  55                  60

Arg His Leu Pro Glu Lys Gln Asn Gly Ile Ser Ala Val Arg Thr Met
 65                  70                  75                  80

Glu Ala Phe His Phe Val Ser Tyr Val Pro Ile Lys Gly Arg Leu Phe
                85                  90                  95

Glu Leu Asp Gly Leu Lys Val Tyr Pro Ile Asp His Gly Gln Glu Ser
                100                 105                 110

Gln Pro Gly Glu Glu Ala Lys Pro Ala Ser Ser Lys Thr Gly Glu Lys
                115                 120                 125

Tyr Ser Pro Lys Glu Leu Leu Ala Leu Leu Lys Cys Val Glu Ala Glu
                130                 135                 140

Ile Ala Ile Asp Asp Gln Arg Arg Thr His Asn Tyr Asp Glu Phe Ile
145                 150                 155                 160

Cys Thr Phe Ile Ser Met
                165

<210> SEQ ID NO 57
<211> LENGTH: 170
<212> TYPE: PRT
<213> ORGANISM: Xenopus Tropicalis

<400> SEQUENCE: 57

Leu Ile Pro Asn Ser Cys Ala Thr His Ala Leu Leu Ser Val Leu Leu
1               5                   10                  15

Asn Cys Ser Gly Val His Leu Gly Pro Thr Leu Ser Arg Ile Lys Glu
                20                  25                  30

Phe Thr Lys Gly Phe Ser Pro Glu Ser Lys Gly Tyr Ala Ile Gly Asn
            35                  40                  45

Ala Pro Glu Leu Ala Lys Ala His Asn Ser His Ala Arg Pro Glu Pro
 50                  55                  60

Arg His Leu Pro Glu Lys Gln Asn Gly Ile Ser Ala Val Arg Thr Met
 65                  70                  75                  80

Glu Ala Phe His Phe Val Ser Tyr Val Pro Ile Lys Gly Arg Leu Phe
                85                  90                  95

Glu Leu Asp Gly Leu Lys Val Tyr Pro Ile Asp His Gly Thr Glu Gly
                100                 105                 110

Gln Ser Thr Glu Glu Thr Lys Ser Ala Ala Leu Lys Ala Pro Val Ser
                115                 120                 125

Gln Gly Glu Lys Phe Ser Pro Lys Glu Leu Leu Ala Leu Leu Lys Cys
                130                 135                 140

Val Glu Ala Glu Ile Ser Ile Asp Asp Gln Arg Arg Thr His Asn Tyr
145                 150                 155                 160

Asp Glu Phe Ile Cys Ala Phe Ile Ser Met
                165                 170

<210> SEQ ID NO 58
<211> LENGTH: 163
<212> TYPE: PRT
<213> ORGANISM: Danio rerio

<400> SEQUENCE: 58

Leu Ile Pro Asn Ser Cys Ala Thr His Ala Leu Leu Ser Val Leu Leu
1               5                   10                  15

```
Asn Cys Ser Gly Val Glu Leu Gly Met Thr Leu Ser Arg Met Lys Ala
            20                  25                  30

Phe Thr Lys Gly Phe Asn Pro Glu Ser Lys Gly Tyr Ala Ile Gly Asn
        35                  40                  45

Ala Pro Glu Leu Ala Lys Ala His Asn Ser His Ala Arg Pro Glu Pro
 50                  55                  60

Arg His Leu Pro Glu Lys Gln Asn Gly Ile Ser Ala Val Arg Thr Met
 65                  70                  75                  80

Glu Ala Phe His Phe Val Ser Tyr Val Pro Ile Lys Asp Arg Leu Phe
                85                  90                  95

Glu Leu Asp Gly Leu Lys Ala Tyr Pro Ile Asp His Gly Gln Asp Ser
            100                 105                 110

Ser Ser Ser Glu Asp Thr Pro Pro Val Leu Gly Glu Lys Tyr Thr Pro
        115                 120                 125

Lys Glu Leu Leu Ala Leu Leu Lys Tyr Val Glu Ala Asp Ile Ala Ile
130                 135                 140

Asp Asp Gln Arg Arg Thr His Asn Tyr Asp Glu Phe Ile Cys Thr Phe
145                 150                 155                 160

Ile Ser Met

<210> SEQ ID NO 59
<211> LENGTH: 154
<212> TYPE: PRT
<213> ORGANISM: Drosophila melanogaster

<400> SEQUENCE: 59

Val Val Pro Asn Ser Cys Ala Thr His Ala Leu Leu Ser Val Leu Leu
1               5                   10                  15

Asn Cys Asn Glu Asn Asn Leu Gln Leu Gly Asp Thr Leu Ser Arg Leu
            20                  25                  30

Lys Thr His Thr Lys Gly Met Ser Pro Glu Asn Lys Gly Leu Ala Ile
        35                  40                  45

Gly Asn Thr Pro Glu Leu Ala Cys Ala His Asn Ser His Ala Met Pro
 50                  55                  60

Gln Ala Arg Arg Arg Leu Glu Arg Thr Gly Ala Gly Val Ser Ser Cys
65                  70                  75                  80

Arg Phe Thr Gly Glu Ala Phe His Phe Val Ser Phe Val Pro Ile Asn
                85                  90                  95

Gly Gln Leu Phe Glu Leu Asp Gly Leu Lys Pro Tyr Pro Met Asn His
            100                 105                 110

Gly Pro Ser Ala Phe Thr Ala Arg Asp Leu Gln Ser Leu Leu Lys Asn
        115                 120                 125

Leu Asp Thr Glu Ile Ala Val Asp Ala Ser Arg Arg Thr His Asn Tyr
130                 135                 140

Asp Lys Phe Ile Cys Thr Phe Leu Ser Met
145                 150

<210> SEQ ID NO 60
<211> LENGTH: 152
<212> TYPE: PRT
<213> ORGANISM: Caenorhabditis elegans

<400> SEQUENCE: 60

Thr Ile Gln Asn Ala Cys Ala Thr Gln Ala Leu Ile Asn Leu Leu Met
1               5                   10                  15
```

```
Asn Val Glu Asp Thr Asp Val Lys Leu Gly Asn Ile Leu Asn Gln Tyr
             20                  25                  30

Lys Glu Phe Ala Ile Asp Leu Asp Pro Asn Thr Arg Gly His Cys Leu
             35                  40                  45

Ser Asn Ser Glu Glu Ile Arg Thr Val His Asn Ser Phe Ser Arg Gln
 50                  55                  60

Thr Leu Phe Glu Leu Asp Ile Lys Gly Gly Glu Ser Glu Asp Asn Tyr
65                  70                  75                  80

His Phe Val Thr Tyr Val Pro Ile Gly Asn Lys Val Tyr Glu Leu Asp
                 85                  90                  95

Gly Leu Arg Glu Leu Pro Leu Val Ala Met Glu Met Tyr Arg Lys
             100                 105                 110

Glu Asn Asn Arg Arg Arg His Asn Tyr Thr Pro Phe Val Ile Leu Glu
             115                 120                 125

Glu Gln Ile Ala Lys Glu Asn Asn Arg Arg Arg His Asn Tyr Thr Pro
             130                 135                 140

Phe Val Ile Glu Leu Met Lys Ile
145                 150

<210> SEQ ID NO 61
<211> LENGTH: 19
<212> TYPE: DNA
<213> ORGANISM: Homo sapiens

<400> SEQUENCE: 61
ttatgggcca gaaaataag                                               19

<210> SEQ ID NO 62
<211> LENGTH: 19
<212> TYPE: DNA
<213> ORGANISM: Homo sapiens

<400> SEQUENCE: 62
ttatgggcct tggccaact                                               19
```